US008399195B2

(12) United States Patent
Mitchell et al.

(10) Patent No.: US 8,399,195 B2
(45) Date of Patent: *Mar. 19, 2013

(54) DETECTING GENETIC ABNORMALITIES

(75) Inventors: Aoy Tomita Mitchell, Elm Grove, WI (US); Michael Mitchell, Elm Grove, WI (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/359,325

(22) Filed: Jan. 26, 2012

(65) Prior Publication Data

US 2012/0190572 A1 Jul. 26, 2012

Related U.S. Application Data

(63) Continuation of application No. 12/581,083, filed on Oct. 16, 2009, now abandoned, which is a continuation-in-part of application No. 11/713,069, filed on Feb. 28, 2007, now Pat. No. 7,799,531.

(60) Provisional application No. 61/106,435, filed on Oct. 17, 2008, provisional application No. 60/777,865, filed on Feb. 28, 2006.

(51) Int. Cl.
*C12Q 1/68* (2006.01)
*C12P 19/34* (2006.01)

(52) U.S. Cl. ....... 435/6.11; 435/6.1; 435/6.12; 435/91.2

(58) Field of Classification Search .................. None
See application file for complete search history.

(56) References Cited

U.S. PATENT DOCUMENTS

| 6,979,541 | B1 | 12/2005 | Pont-Kingdon et al. |
| 7,799,531 | B2 | 9/2010 | Mitchell et al. |
| 2001/0048756 | A1 | 12/2001 | Staub et al. |
| 2003/0082606 | A1 | 5/2003 | Lebo et al. |
| 2003/0211522 | A1 | 11/2003 | Landes et al. |
| 2004/0137452 | A1 | 7/2004 | Levett et al. |
| 2004/0137470 | A1 | 7/2004 | Dhallan |
| 2005/0049793 | A1 | 3/2005 | Paterlini-Brechot |
| 2005/0164241 | A1 | 7/2005 | Hahn et al. |
| 2006/0121452 | A1 | 6/2006 | Dhallan |
| 2006/0160105 | A1 | 7/2006 | Dhallan |
| 2007/0207466 | A1 | 9/2007 | Cantor et al. |
| 2008/0020390 | A1* | 1/2008 | Mitchell et al. ............ 435/6 |
| 2008/0318235 | A1 | 12/2008 | Handyside |

FOREIGN PATENT DOCUMENTS

| WO | WO 00/34652 A1 | 6/2000 |
| WO | WO 02/068685 A2 | 9/2002 |
| WO | WO 03/062441 A1 | 7/2003 |
| WO | WO 2004/078999 A1 | 9/2004 |
| WO | WO 2004/079011 A1 | 9/2004 |
| WO | WO 2005/023091 A2 | 3/2005 |
| WO | WO 2005/035725 A2 | 4/2005 |
| WO | WO 2005/044086 A2 | 5/2005 |
| WO | WO 2006/011738 A1 | 2/2006 |
| WO | WO 2007/057647 A1 | 5/2007 |

OTHER PUBLICATIONS

Reed et al., Bone Marrow Transplantation. 2002. 29:527-529.
Andre, P. et al., Fidelity and Mutational Spectrum of Pfu DNA Polymerase on a Human Mitochondrial DNA Sequence, Genome Res., 1997, vol. 7, pp. 843-852.
Adams, K. et al., Microchimerism An investigative Frontier in Autoimmunity and Transplantation. JAMA. 2004, vol. 291(9), pp. 1127-1131.
Andonova, S., et al., Prenat. Diagn., 2004, vol. 24(3), pp. 202-208.
BBC News, Safer test for unborn babies hope. BBC News Oct. 4, 2005. htt//news.bbc.co.uk/2/h i/health/4307628.stm.
Birch, L., et al., Clin. Chem., 2005, vol. 51 (2), pp. 312-320.
Chim, S.C., et al., Detection of the placental epigenetic signature of the maspin gene in maternal plasma, PNAS 2005, vol. 102(41), pp. 14753-14758.
Cline, J. et al., PCR fidlity of Pfu polymerase and other thermostable DNA polymerases, Nucleic Acids Res. 1996, vol. 24(18), pp. 3546-3551.
Dhallan, R., et al., A non-invasive test for prenatal diagnosis..., The Lancet, 2007, vol. 369, pp. 474-481, www.thelancet.com 2007. DOI:1 0.1 016/S0140-6736(07)60115-9.
Dhallan, R. et al., Methods to Increase the Percentage of Free Fetal DNA Recovered From the Maternal Circulation. JAMA, 2004. 291 (9): p. 1114-1119.
Ding, C. et al., MS Analysis of single nucleotide differences in circulating nucleic acids: Application to noninvasive prenatal diagnosis. PNAS, 2004, 101 (29): p. 10762-10767.
Khrapko, K., et al., Constant denaturant capillary electrophoresis (CDCE): a high resolution approach to mutational analysis. Nucleic Acids Res., 1994, vol. 22(3), p. 364-369.
Lerman, L.S. et al., Computational simulation of DNA melting and its application to denaturing gradient gel electrophoresis. Methods Enzymol., 1987, vol. 155, pp. 482-501.
Li, Y. et al., JAMA., 2005, vol. 293(7), pp. 843-849. Correction: JAMA, 2006, vol. 293(14), pp. 1728.
Li, Y. et al., Size Separation of Circulatory DNA in Maternal Plasma Permits Ready Detection of Fetal DNAPolymorphrsms. Clin. Chem., 2004, vol. 50(6), pp. 1002-1011.
Lim, E.L. et al., Combination of Competitive Quantitative PCT ..., Appl. Environ. Microbiol., 2001, vol. 67(9), pp. 3897-3903.
Li-Sucholeiki, X.C. et al., A sensitive scanning technology for low frequency nuclear point mutations..., Nucleic Acids Res., 2000, vol. 28(9), pp. E44 (8 pages).
Lo, Y.M.D. et al., Am J. Hum. Genet., 1998, vol. 62(4), pp. 768-775.
Lo, Y.M.D. et al., Free Fetal DNA in Maternal Circulation. 2004. JAMA 292(23): p. 2835-2836.
Lo, Y.M.D. et al., Increased Fetal DNA Concentrations in the Plasma of Pregnant Women Carrying Fetuses with Trisomy 21. Clin. Chem., 1999, vol. 45(10), pp. 1747-1751.

(Continued)

Primary Examiner — Carla Myers
(74) Attorney, Agent, or Firm — Convergent Law Group LLP

(57) ABSTRACT

The present invention is directed to compositions and methods for detecting genetic abnormalities. The present invention encompasses methods and compositions for comparing alleles in a sample containing both maternal and fetal nucleic acids in order to identify genetic abnormalities.

12 Claims, 69 Drawing Sheets

OTHER PUBLICATIONS

Malone, F.D. et al., First-trimester sonographic screening for Down syndrome. Obstet. Gynecol., 2003, vol. 102(5 Pt 1), pp. 1066-1079.

Parsons, B. et al., Genotypic selection methods for the direct analysis of point mutations. Mutation Research, 1997. 387: p. 97-121.

Pertl, B., et al., Hum. Genet., 2000. 106: p. 45-49.

Poon, L.M. et al., Differential DNA Methylation between Fetus and Mother as a Strategy for Detecting Fetal DNA in Maternal Plasma. Clin. Chem., 2002. 48(1): p. 35-41.

Samura, O. et al., Diagnosis of Trisomy 21 in Fetal Nucleated Erythrocytes from Maternal Blood by Use of Short Tandem Repeat Sequences. Clin. Chem., 2001.47(9): p. 1622-1626.

Simpson, J.L. et al., Cell-Free Fetal DNA in Maternal Blood: Evolving Clinical Applications. JAMA, 2004. 291 (9): p. 1135-1137.

The International HapMap Consortium, The International HapMap Project. Nature, 2003. 426. p. 789-796.

The International HapMap Consortium, A haplotype map of the human genome. Nature, 2005.437. p. 1299-1320.

Thompson, J.R., et al., Nucleic Acids Res., 2002. 30(9): p. 2083-2088.

Thorisson, G.A., et al., The International HapMap Project Web site. Genome Res., 2005. 15: p. 1592-1593.

Wald, N.J., et al., Antenatal screening for Down's syndrome with the quadruple test. Lancet, 2003. 361 (9360): p. 835-836.

Zheng, W. et al., Origins fo human mitochondrial point mutations as DNA polymerase ymediated errors, Mutat. Res., 2006. 599(1-2): p. 11-20.

International Search Report for International Application No. PCT/US2007/005399 (2007).

Database SNP (Online) Retrieved from NCBI Database Accession No. rs2822654 Abstract (2004).

Antonarakis et al., Analysis ofDNA haplotypes suggests a genetic predisposition to trisomy 21 associated with DNA sequences on chromosome 21, PNAS, 82(10), 3360-3364(1985).

Nagy et aL, Rapid determination of trisomy 21 from amniotic fluid cells using singlenucleotide polymorphic loci, Prenat. Diagn., 25(12). 1138-1141 (2005).

Pont-Kingdon et al., Nucleic Acids Res., 33(10). e89 (2005).

Illanes et al., Prenatal Diagnosis, 2006. 26: 1216-1218.

Li et al., Journal of the Society for Gynecologic Investigation. 2003. 10: 503-508.

Zhong et al., Annals NY Acad Sci. 2006, 945: 250-257.

Human Chromosome 21 cSNP database, University of Geneva. Swiss Institute of Bioinformatics, HC21 S00131 (printed Oct. 14, 2008).

HOWDY Database, Human Organized Whole Genome Database, Marker 5618, NM_003895 (printed Oct. 4, 2008).

Puers, C., et al., Am. J. Hum. Genet. 53:953-958,1993.

* cited by examiner

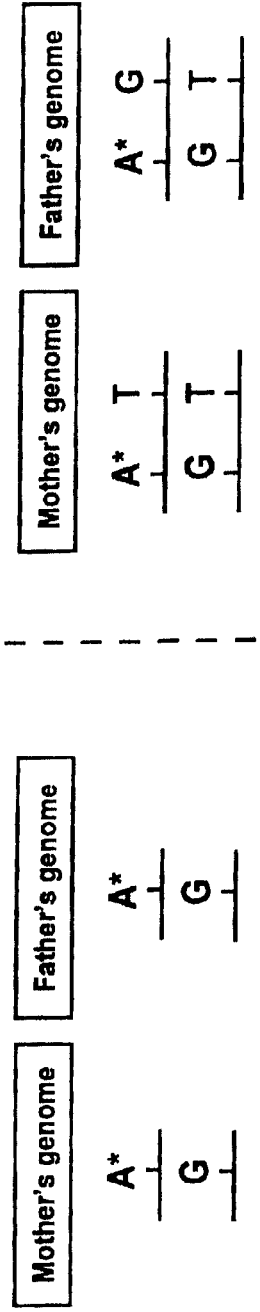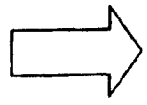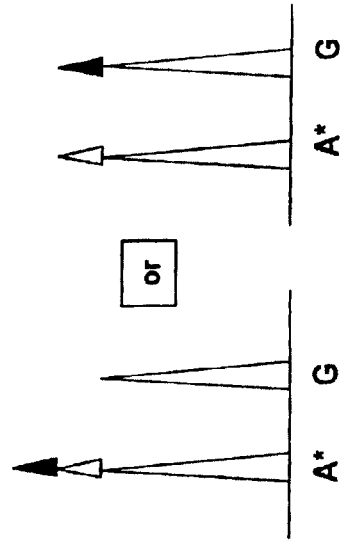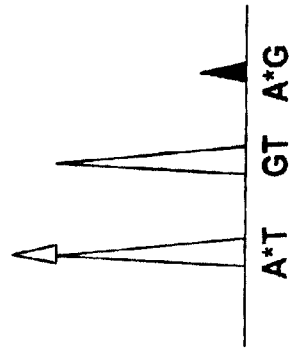
FIG. 4

FIG. 5A

| Tandem SNP #/ Observed haplotypes | dbSNP Name | | Chromosome | Chromosome Position | bp dif |
|---|---|---|---|---|---|
| 1 | rs10482852 | A/C | Chr21 | 14613855 | 86 |
| CC/CT/AC | rs2822567 | C/T | Chr21 | 14613941 | |
| 2 | rs2822654 | A/C | Chr21 | 14687773 | 13 |
| AA/AG/CG/CA | rs1882882 | A/G | Chr21 | 14687786 | |
| 3 | rs2822785 | A/G | Chr21 | 14876399 | 65 |
| AG/GG/AA/GA | rs2822786 | A/G | Chr21 | 14876464 | |
| 4 | rs2822786 | A/G | Chr21 | 14876464 | 67 |
| GC/AC/GT | rs2822787 | C/T | Chr21 | 14876531 | |
| 5 | rs2822816 | A/G | Chr21 | 14948471 | 97 |
| AA/GT/GA | rs2822817 | A/T | Chr21 | 14948568 | |
| 6 | rs2822878 | C/T | Chr21 | 15033311 | 90 |
| CA/CG/TG | rs2822879 | A/G | Chr21 | 15033401 | |
| 7 | rs2223163 | A/G | Chr21 | 15149849 | 72 |
| AT/GT/AC | rs2822963 | C/T | Chr21 | 15149921 | |
| 8 | rs1297213 | A/G | Chr21 | 15253641 | 83 |
| GG/AG/GT/AT | rs1297214 | G/T | Chr21 | 15253724 | |
| 9 | rs2142450 | C/T | Chr21 | 15257273 | 67 |
| CT/CC/TT | rs10482863 | C/T | Chr21 | 15257340 | |
| 10 | rs10482863 | C/T | Chr21 | 15257340 | 46 |
| TC/CC/TT | rs1041403 | C/T | Chr21 | 15257386 | |
| 11 | rs2823333 | C/T | Chr21 | 15825896 | 89 |
| TA/CA/TG | rs2823334 | A/G | Chr21 | 15825985 | |
| 12 | rs2823335 | A/G | Chr21 | 15826379 | 78 |
| GG/AC/GC | rs992557 | C/G | Chr21 | 15826457 | |
| 13 | rs2823348 | A/G | Chr21 | 15833575 | 26 |
| AA/GG/AG | rs2823349 | A/G | Chr21 | 15833601 | |
| 14 | rs2823502 | A/C | Chr21 | 16124651 | 32 |
| AT/AC/CT/CC | rs2823503 | C/T | Chr21 | 16124683 | |
| 15 | rs960391 | C/T | Chr21 | 17034864 | 29 |
| CC/CA/TC/TA | rs13049140 | A/C | Chr21 | 17034893 | |
| 16 | rs2824078 | C/T | Chr21 | 17134418 | 30 |
| CA/TA/TG | rs10482886 | A/G | Chr21 | 17134448 | |
| 17 | rs1999288 | C/T | Chr21 | 17696177 | 92 |
| CT/CC/TC | rs208897 | C/T | Chr21 | 17696269 | |
| 18 | rs2824310 | A/G | Chr21 | 17744045 | 99 |
| GG/GA/AA/AG | rs6517774 | A/G | Chr21 | 17744144 | |
| 19 | rs728015 | A/G | Chr21 | 17968624 | 33 |
| GG/AA/AG/GA | rs728014 | A/G | Chr21 | 17968657 | |
| 20 | rs1047978 | C/G | Chr21 | 18091026 | 63 |
| GG/CG/CC/GC | rs2824495 | C/G | Chr21 | 18091089 | |
| 21 | rs157058 | A/G | Chr21 | 18355312 | 53 |
| GT/GC/AT/AC | rs150141 | C/T | Chr21 | 18355365 | |
| 22 | rs2824733 | A/G | Chr21 | 18610953 | 79 |
| GG/GT/AG/AT | rs2824734 | G/T | Chr21 | 18611032 | |

FIG. 5B

|  | 23 | rs963638 | A/G | Chr21 | 19009158 | 56 |
|---|---|---|---|---|---|---|
| AA/GT/GA/AT | | rs963639 | A/T | Chr21 | 19009214 | |
| | 24 | rs2187166 | A/T | Chr21 | 19081111 | 99 |
| AC/TA/TC/AA | | rs2156203 | A/C | Chr21 | 19081210 | |
| | 25 | rs2825470 | C/T | Chr21 | 19567109 | 60 |
| CT/TC/CC/TT | | rs2825471 | C/T | Chr21 | 19567169 | |
| | 26 | rs2407581 | G/T | Chr21 | 20272611 | 28 |
| TT/GC/GT | | rs2825926 | C/T | Chr21 | 20272639 | |
| | 27 | rs377685 | A/G | Chr21 | 20272988 | 33 |
| GT/AT/GC/AC | | rs420778 | C/T | Chr21 | 20273021 | |
| | 28 | rs2826058 | A/C | Chr21 | 20464969 | 92 |
| AG/CT/CG | | rs2826059 | G/T | Chr21 | 20465061 | |
| | 29 | rs2826072 | C/T | Chr21 | 20487958 | 95 |
| CT/CC/TT | | rs2826073 | C/T | Chr21 | 20488053 | |
| | 30 | rs2032203 | C/T | Chr21 | 20598845 | 98 |
| CC/TC/TT | | rs2826152 | C/T | Chr21 | 20598943 | |
| | 31 | rs1735808 | C/T | Chr21 | 20766284 | 45 |
| CA/TA/CG/TG | | rs1786400 | A/G | Chr21 | 20766329 | |
| | 32 | rs2014509 | C/T | Chr21 | 21113081 | 79 |
| TG/CA/CG/GA | | rs2014519 | A/G | Chr21 | 21113160 | |
| | 33 | rs2155798 | A/G | Chr21 | 21471022 | 75 |
| GA/AA/GG | | rs2155799 | A/G | Chr21 | 21471097 | |
| | 34 | rs1475881 | C/G | Chr21 | 21748820 | 96 |
| GA/GG/CA | | rs7275487 | A/G | Chr21 | 21748916 | |
| | 35 | rs2522558 | C/G | Chr21 | 21916691 | 23 |
| CG/GG/GC/CC | | rs12627388 | C/G | Chr21 | 21916714 | |
| | 36 | rs12627388 | C/G | Chr21 | 21916714 | 48 |
| GC/GT/CC/CT | | rs2522559 | C/T | Chr21 | 21916762 | |
| | 37 | rs1735934 | A/G | Chr21 | 21995555 | 78 |
| AC/GC/GT | | rs2826958 | C/T | Chr21 | 21995633 | |
| | 38 | rs994676 | A/G | Chr21 | 22043945 | 34 |
| AC/GT/AT/GC | | rs2826982 | C/T | Chr21 | 22043979 | |
| | 39 | rs1735976 | A/G | Chr21 | 22054777 | 31 |
| AA/GC/AC | | rs2827016 | A/C | Chr21 | 22054808 | |
| | 40 | rs1013069 | A/G | Chr21 | 22545627 | 67 |
| AA/GA/AG/GG | | rs2827307 | A/G | Chr21 | 22545694 | |
| | 41 | rs244260 | A/G | Chr21 | 23311737 | 88 |
| AT/GT/AC/GC | | rs244261 | C/T | Chr21 | 23311825 | |
| | 42 | rs2051265 | A/C | Chr21 | 23334109 | 47 |
| CG/CC/AG/AC | | rs198061 | C/G | Chr21 | 23334156 | |

FIG. 6A

1) Whole sequence ::: rs432114 - rs365433  CC/CT/GC/GT

AACAAATCTTCATCTTGGAATAGCCTGTGAGAATGCCTAATCATCTACGAATgTTACTTT
GGCACCATCTACTGGACAgATTAAATAACAACCAACTCACTGTGGATTAGACCTACTTCT
ATTTCAG  (SEQ ID NO:1)

```
OLIGO            (SEQ ID NOs:2, 3)
LEFT PRIMER       20     20    55.08   45.00   3.00   2.00
ATAGCCTGTGAGAATGCCTA
RIGHT PRIMER     107     20    55.30   45.00   5.00   0.00
ATCCACAGTGAGTTGGTTGT
SEQUENCE SIZE: 127
INCLUDED REGION SIZE: 127
```

PRODUCT SIZE: 88, PAIR ANY COMPL: 5.00, PAIR 3' COMPL: 1.00

```
    1 AACAAATCTTCATCTTGGAATAGCCTGTGAGAATGCCTAATCATCTACGAATgTTACTTT
                          >>>>>>>>>>>>>>>>>>>>

61 GGCACCATCTACTGGACAgATTAAATAACAACCAACTCACTGTGGATTAGACCTACTTCT
                                             <<<<<<<<<<<<<<<<<<<<

121 ATTTCAG
```

2) Whole sequence ::: rs7277033-rs2110153 CC/CT/TC/TT
PCR did not work

TTCCTGGAAAACAAAAGTATTTCTTTCATAGCCCAGCTAGCAtGATAAATCAGCgAGTCA
 GAATTCTAGCTTTGTTGTAAGGTT (SEQ ID NO:4)

```
OLIGO            (SEQ ID NOs: 5, 6)
LEFT PRIMER        2     20    51.63   30.00   5.00   3.00
TCCTGGAAAACAAAAGTATT
RIGHT PRIMER      84     21    51.36   33.33   4.00   0.00
AACCTTACAACAAAGCTAGAA
SEQUENCE SIZE: 84
INCLUDED REGION SIZE: 84
```

PRODUCT SIZE: 83, PAIR ANY COMPL: 3.00, PAIR 3' COMPL: 2.00

```
    1 TTCCTGGAAAACAAAAGTATTTCTTTCATAGCCCAGCTAGCAtGATAAATCAGCgAGTCA
      >>>>>>>>>>>>>>>>>>>>

61 GAATTCTAGCTTTGTTGTAAGGTT
          <<<<<<<<<<<<<<<<<<<<<
```

3) Whole sequence ::: rs2822654-rs1882882 AA/AG/CA/CG

CACTAAGCCTTGGGGATCCAGCTGCTTaAGCACTAAGACCgTATCTAGCTCCTTTTAGTA
TTTCCACAGCA (SEQ ID NO: 7)

OLIGO            (SEQ ID NOs: 8, 9)

FIG. 6B

```
LEFT PRIMER             2    20   60.46   55.00   6.00   2.00
ACTAAGCCTTGGGGATCCAG
RIGHT PRIMER           71    21   54.78   38.10   3.00   0.00
TGCTGTGGAAATACTAAAAGG
SEQUENCE SIZE: 71
INCLUDED REGION SIZE: 71

PRODUCT SIZE: 70, PAIR ANY COMPL: 4.00, PAIR 3' COMPL: 0.00

1 CACTAAGCCTTGGGGATCCAGCTGCTTaAGGACTAAGACCgTATCTAGCTCCTTTTAGTA
      >>>>>>>>>>>>>>>>>>>>                                <<<<<<<<<<

61 TTTCCACAGCA
      <<<<<<<<<<

4) Whole sequence ::: rs368657-rs376635 AA/AG/GA/GG

TCCTCCAGAGGTAATCCTGTGATCAGCACTAACaCCACATACCAGCCCTTTCATCAGCTT
GTTGGAGAAGCATCTTTACTTCCCgCCAAGCAGTGACCTagataccatctcacaccagtt
agaatcaggatcattaaaaagtcaagaaaaaacag (SEQ ID NO: 10)

OLIGO            (SEQ ID NOs: 11, 12)
LEFT PRIMER             3    20   55.20   50.00   5.00   3.00
CTCCAGAGGTAATCCTGTGA
RIGHT PRIMER          117    21   55.10   47.62   5.00   2.00
tggtgtgagatggtatctAGG
SEQUENCE SIZE: 155
INCLUDED REGION SIZE: 155

PRODUCT SIZE: 115, PAIR ANY COMPL: 3.00, PAIR 3' COMPL: 2.00

1 TCCTCCAGAGGTAATCCTGTGATCAGCACTAACaCCACATACCAGCCCTTTCATCAGCTT
      >>>>>>>>>>>>>>>>>>>>

61 GTTGGAGAAGCATCTTTACTTCCCgCCAAGCAGTGACCTagataccatctcacaccagtt
                                              <<<<<<<<<<<<<<<<<<<<<

121 agaatcaggatcattaaaaagtcaagaaaaaacag

5) Whole sequence ::: rs2822731-rs2822732 AA/AG/GA/GG

TCCAAGTATAATCCATGAATCTTGTTTAAATATAGATCAAaTAAACCACTATACCAAAAA
CATCAAAAGACAACTGGGTAAATTTTTTTAAATGACTAGCTATTTGATGTTAAgGAAGTAA
TGTTACTCTCTTATATACAATTTGAA (SEQ ID NO: 13)

OLIGO            (SEQ ID NOs: 14, 15)
LEFT PRIMER             6    22   50.35   27.27   6.00   3.00
GTATAATCCATGAATCTTGTTT
RIGHT PRIMER          146    22   45.69   22.73   6.00   1.00
TTCAAATTGTATATAAGAGAGT
SEQUENCE SIZE: 146
INCLUDED REGION SIZE: 146

PRODUCT SIZE: 141, PAIR ANY COMPL: 4.00, PAIR 3' COMPL: 2.00
```

FIG. 6C

```
  1 TCCAAGTATAATCCATGAATCTTGTTTAAATATACATCAAaTAAACCACTATACCAAAAA
    >>>>>>>>>>>>>>>>>>>>>>

61 CATCAAAAGACAACTGGGTAAATTTTTTAAATGACTAGCTATTTGATGTTAAgGAAGTAA

121 TGTTACTCTCTTATATACAATTTGAA
    <<<<<<<<<<<<<<<<<<<<<<<<<
```

6) Whole sequence ::: rs6516899-rs455221 CC/CT/TC/TT

ATGGAACCGAAACTTCAAGTAGTTTCATAcGTATCACATTGACAGTTTTCTCTAAGTTTT
CtGGTCTTATGACTCGTTGTTTCATTATTAAAACTGTGCCAGTGTATGCATAGGGCTTAG
AAATTTTTTAAT (SEQ ID NO: 16)

```
OLIGO          (SEQ ID NOs: 17, 18)
LEFT PRIMER          1   18   53.87   38.89   4.00   3.00
ATGGAACCGAAACTTCAA
RIGHT PRIMER        91   22   52.84   27.27   5.00   1.00
TTAATAATGAAACAACGAGTCA
SEQUENCE SIZE: 132
INCLUDED REGION SIZE: 132
```

PRODUCT SIZE: 91, PAIR ANY COMPL: 4.00, PAIR 3' COMPL: 0.00

```
  1 ATGGAACCGAAACTTCAAGTAGTTTCATAcGTATCACATTGACAGTTTTCTCTAAGTTTT
    >>>>>>>>>>>>>>>>>>

61 CtGGTCTTATGACTCGTTGTTTCATTATTAAAACTGTGCCAGTGTATGCATAGGGCTTAG
                                           <<<<<<<<<<<<<<<<<<<<<<

121 AAATTTTTTAAT
```

7) Whole sequence ::: rs7275381-rs12627144 GA/GG/TA/TG acaggatccttcctgaagacaccaccttggggagggtgaagGataaagaatttgatcaga
aatcaagggtggtgagatacatgttaaggatgaataaactggccttttaggattcttgct
aaaAttagacaatgcagaggcaaccacagagtccaag (SEQ ID NO: 19)

```
OLIGO          (SEQ ID NOs: 20, 21)
LEFT PRIMER         10   19   55.53   47.37   4.00   0.00
ttcctgaagacaccacctt
RIGHT PRIMER       157   18   54.94   55.56   3.00   2.00
cttggactctgtggttgc
SEQUENCE SIZE: 157
INCLUDED REGION SIZE: 157
```

PRODUCT SIZE: 148, PAIR ANY COMPL: 5.00, PAIR 3' COMPL: 1.00

```
  1 acaggatccttcctgaagacaccaccttggggagggtgaagGataaagaatttgatcaga
             >>>>>>>>>>>>>>>>>>>

61 aatcaagggtggtgagatacatgttaaggatgaataaactggccttttaggattcttgct
```

FIG. 6D

```
121 aaaAttagacaatgcagaggcaaccacagagtccaag
    <<<<<<<<<<<<<<<<<<<
```

8) Whole sequence ::: rs1999288-rs208897 CC/CT/TC

AATTTCCATTAAATCTTGTTCGTTGCTTTACTGAGGCACTGAAGTTACCAATGTTcCACT
GGTTGACCTGCGGGGCTATCTCTAGGTTATGTTACTCCAGAAAATGAATTGTGTATAAAA
GAGGCCTTGGAGGAAGGCGTTTTATTCaCATCAGTTGTTTTGCACATTGCTTA (SEQ ID NO: 22)

```
OLIGO            (SEQ ID NOs: 23, 24)
LEFT PRIMER          30     20    54.40    50.00    4.00    2.00
ACTGAGGCACTGAAGTTACC
RIGHT PRIMER        173     20    54.96    35.00    4.00    0.00
TAAGCAATGTGCAAAACAAC
SEQUENCE SIZE: 173
INCLUDED REGION SIZE: 173
```

PRODUCT SIZE: 144, PAIR ANY COMPL: 4.00, PAIR 3' COMPL: 0.00

```
  1 AATTTCCATTAAATCTTGTTCGTTGCTTTACTGAGGCACTGAAGTTACCAATGTTcCACT
                                   >>>>>>>>>>>>>>>>>>>>

61 GGTTGACCTGCGGGGCTATCTCTAGGTTATGTTACTCCAGAAAATGAATTGTGTATAAAA

121 GAGGCCTTGGAGGAAGGCGTTTTATTCaCATCAGTTGTTTTGCACATTGCTTA
                                 <<<<<<<<<<<<<<<<<<<<
```

9) Whole sequence ::: rs1475881-rs7275487 CA/CG/GA/GG
PCR did not work

TCGGTTTCAGCAGGAAAGTTATTTTTAATAACTTCCCTGTATTTcTTGGTTTCAGTTATTAATTAACTCA
TTAATGCTAAACTTTGTGATCCTAGGTTAAAAAACATATTCAAGATAGCTTCAGAATGTTTGGTATACAA
gTAGGTCTGGCTAAATATAAGTGTTAGCTTT CTCAAGCATC TAAATGCTGG (SEQ ID NO: 25)

```
OLIGO            (SEQ ID NOs: 26, 27)
LEFT PRIMER          10     20    48.49    25.00    5.00    3.00
GCAGGAAAGTTATTTTTAAT
RIGHT PRIMER        179     21    54.70    38.10    4.00    1.00
TGCTTGAGAAAGCTAACACTT
SEQUENCE SIZE: 191
INCLUDED REGION SIZE: 191
```

PRODUCT SIZE: 170, PAIR ANY COMPL: 5.00, PAIR 3' COMPL: 2.00

```
  1 TCGGTTTCAGCAGGAAAGTTATTTTTAATAACTTCCCTGTATTTcTTGGTTTCAGTTATT
                 >>>>>>>>>>>>>>>>>>>>

61 AATTAACTCATTAATGCTAAACTTTGTGATCCTAGGTTAAAAAACATATTCAAGATAGCT

121 TCAGAATGTTTGGTATACAAgTAGGTCTGGCTAAATATAAGTGTTAGCTTTCTCAAGCAT
                                           <<<<<<<<<<<<<<<<<<<<<

181 CTAAATGCTGG
```

FIG. 6E

ALTERNATIVE:: ( LESS THAN 5 bp APART )

AAGTTATTTTTAATAACTTCCCTGTATTTcTTGGTTTCAGTTATTAATTAACTCATTAAT
GCTAAACTTTGTGATCCTAGGTTAAAAAACATATTCAAGATAGCTTCAGAATGTTTGGTA
TACAAgTAGGTCTGGCTAAATATAAGTGTTAGCTTTCTCAAGCATC (SEQ ID NO: 28)

```
OLIGO           (SEQ ID NOs: 29, 30)
LEFT PRIMER         6    20   47.68   25.00   6.00   0.00
ATTTTTAATAACTTCCCTGT
RIGHT PRIMER      148    20   49.30   40.00   4.00   0.00
CACTTATATTTAGCCAGACC
SEQUENCE SIZE: 166
INCLUDED REGION SIZE: 166
```

PRODUCT SIZE: 143, PAIR ANY COMPL: 4.00, PAIR 3' COMPL: 1.00

```
    1 AAGTTATTTTTAATAACTTCCCTGTATTTcTTGGTTTCAGTTATTAATTAACTCATTAAT
          >>>>>>>>>>>>>>>>>>>>

61 GCTAAACTTTGTGATCCTAGGTTAAAAAACATATTCAAGATAGCTTCAGAATGTTTGGTA

121 TACAAgTAGGTCTGGCTAAATATAAGTGTTAGCTTTCTCAAGCATC
              <<<<<<<<<<<<<<<<<<<<
```

10) Whole sequence ::: rs1735976-rs2827016   AA/AC/GA/GC

ATTCATTGTGTAGAAAGTGCCTGACTCAGTGTTTGGAAATTGTCTGACTTTTCCTCATAT
aTAGTGTGGTTTCATGTTATTGTATATAAGAaCTGACATGAACTCTGTTTACAATAATCT
CCCAGTGCCATAAAGACCATAATAAATAATAT (SEQ ID NO: 31)

```
OLIGO           (SEQ ID NOs: 32, 33)
LEFT PRIMER        27    20   54.11   40.00   4.00   1.00
CAGTGTTTGGAAATTGTCTG
RIGHT PRIMER      129    20   55.17   45.00   3.00   2.00
GGCACTGGGAGATTATTGTA
SEQUENCE SIZE: 152
INCLUDED REGION SIZE: 152
```

PRODUCT SIZE: 103, PAIR ANY COMPL: 5.00, PAIR 3' COMPL: 1.00

```
    1 ATTCATTGTGTAGAAAGTGCCTGACTCAGTGTTTGGAAATTGTCTGACTTTTCCTCATAT
                                 >>>>>>>>>>>>>>>>>>>>

61 aTAGTGTGGTTTCATGTTATTGTATATAAGAaCTGACATGAACTCTGTTTACAATAATCT
                                                         <<<<<<<<<<

121 CCCAGTGCCATAAAGACCATAATAAATAATAT
          <<<<<<<<<<
```

2$^{nd}$ group of primers

11) Whole sequence ::: rs447349-rs2824097   CT/TC/TT ( 156 long )

CACTGGGTCCTGTTCTTAAGTACACATAATACCACaCAGGAGAAAATCAGGCTAATTGTA

FIG. 6F

AATGGGCAACCTACTTAATTGTTTCATTAAAAAGCATACAGATTACATTTACACTAtAGC
TAGTCTTGTTTGTTTTTTTATTTTGCAAAAGTAATTACGGCCC (SEQ ID NO: 34)

```
OLIGO              (SEQ ID NOs: 35, 36)
LEFT PRIMER           8    20    47.79    35.00    6.00    2.00
TCCTGTTGTTAAGTACACAT
RIGHT PRIMER        163    18    53.29    44.44    8.00    2.00
GGGCCGTAATTACTTTTG
SEQUENCE SIZE: 163
INCLUDED REGION SIZE: 163
```

PRODUCT SIZE: 156, PAIR ANY COMPL: 5.00, PAIR 3' COMPL: 1.00

```
     1 CACTGGGTCCTGTTGTTAAGTACACATAATACCACaCAGGAGAAAATCAGGCTAATTGTA
              >>>>>>>>>>>>>>>>>>>>

61 AATGGGCAACCTACTTAATTGTTTCATTAAAAAGCATACAGATTACATTTACACTAtAGC

121 TAGTCTTGTTTGTTTTTTTATTTTGCAAAAGTAATTACGGCCC
                             <<<<<<<<<<<<<<<<<<
```

12) Whole sequence ::: rs418989- rs13047336 AC/AT/CC

CTACTCAGTAGGCACTTTGTGTCTAGAAACTTCTGTGTCAACgGTTTTCCCTCTCTCTGG
AATTCaTCAGGACAGAAGTGATTGGTGTGGTGGAAGAGGGTTGTGSTA (SEQ ID NO: 37)

```
OLIGO              (SEQ ID NOs: 38, 39)
LEFT PRIMER           3    21    54.50    47.62    5.00    3.00
ACTCAGTAGGCACTTTGTGTC
RIGHT PRIMER         97    18    54.95    50.00    2.00    0.00
TCTTCCACCACACCAATC
SEQUENCE SIZE: 108
INCLUDED REGION SIZE: 108
```

PRODUCT SIZE: 95, PAIR ANY COMPL: 5.00, PAIR 3' COMPL: 2.00

```
     1 CTACTCAGTAGGCACTTTGTGTCTAGAAACTTCTGTGTCAACgGTTTTCCCTCTCTCTGG
           >>>>>>>>>>>>>>>>>>>>>

61 AATTCaTCAGGACAGAAGTGATTGGTGTGGTGGAAGAGGGTTGTGSTA
                      <<<<<<<<<<<<<<<<<<
```

13) Whole sequence ::: rs987980- rs987981 AG/GG/GT

TGGCTTTTCAAAGGTAAAATTTACTaAGTGTATTAATATTTTACCAATTTCCAGCCAGGA
GAGTATGAATGTTGCATTATTACATTGCTTTGAAACAAAGCATTAgTCTTAATTCAGAAG
TTTAAATTCACATCTTAACGTTCC (SEQ ID NO: 40)

```
   OLIGO            (SEQ ID NOs: 41, 42)
LEFT PRIMER           1    19    53.67    31.58    6.00    2.00
TGGCTTTTCAAAGGTAAAA
RIGHT PRIMER        144    21    54.59    33.33    6.00    3.00
GCAACGTTAACATCTGAATTT
SEQUENCE SIZE: 144
```

FIG. 6G

INCLUDED REGION SIZE: 144

PRODUCT SIZE: 144, PAIR ANY COMPL: 6.00, PAIR 3' COMPL: 3.00

```
    1 TGCCTTTTCAAAGGTAAAATTTACTaAGTGTATTAATATTTTACCAATTTCCAGCCAGGA
      >>>>>>>>>>>>>>>>>>>>

61 GAGTATGAATGTTGCATTATTACATTGCTTTGAAACAAAGCATTAgTCTTAATTCAGAAG

121 TTTAAATTCAGATGTTAACGTTGC
      <<<<<<<<<<<<<<<<<<<<<
```

14) Whole sequence ::: rs4143392- rs4143391 CA/CG/GA/GG

TAAGTATTGAAGAAAGGAGAATTTAAATTACTTCATATACctgataaaggaaaacatata
CAAGGCAAATAAACATCTTAGATCATGACATATAAAATAATAGATTATTA (SEQ ID NO: 43)

OLIGO          (SEQ ID NOs: 44, 45)
LEFT PRIMER          7    20    49.56    25.00    4.00    4.00
TTGAAGAAAGGAGAATTTAA
RIGHT PRIMER        98    22    45.86    22.73    6.00    3.00
ATTTTATATGTCATGATCTAAG
SEQUENCE SIZE: 110
INCLUDED REGION SIZE: 110

PRODUCT SIZE: 92, PAIR ANY COMPL: 4.00, PAIR 3' COMPL: 1.00

```
    1 TAAGTATTGAAGAAAGGAGAATTTAAATTACTTCATATACctgataaaggaaaacatata
      >>>>>>>>>>>>>>>>>>>>

61 CAAGGCAAATAAACATCTTAGATCATGACATATAAAATAATAGATTATTA
                              <<<<<<<<<<<<<<<<<<<<<<
```

15) Whole sequence ::: rs1691324- rs13050434 CG/TA/TG ( 4 bp apart for right primer)

TGCAGAGATTACAGGTGTGAGCCACCGTGCCCAGCCTCATAACcGTTTCAACTACTTTTT
CACTTGACAAGCAGATGTGAAGTTAACAAAGTCACCCATATTTGAAATAAAGATAGTATA
TTCCTGGGGtAGGCAGAGGCAGTTGAGGATCATGAAATAACTATG (SEQ ID NO: 46)

OLIGO          (SEQ ID NOs: 47, 48)
LEFT PRIMER          4    19    49.78    47.37    4.00    4.00
AGAGATTACAGGTGTGAGC
RIGHT PRIMER       153    19    54.61    47.37    4.00    0.00
ATGATCCTCAACTGCCTCT
SEQUENCE SIZE: 165
INCLUDED REGION SIZE: 165

PRODUCT SIZE: 150, PAIR ANY COMPL: 4.00, PAIR 3' COMPL: 2.00

```
    1 TGCAGAGATTACAGGTGTGAGCCACCGTGCCCAGCCTCATAACcGTTTCAACTACTTTTT
      >>>>>>>>>>>>>>>>>>>

61 CACTTGACAAGCAGATGTGAAGTTAACAAAGTCACCCATATTTGAAATAAAGATAGTATA
```

FIG. 6H

```
121 TTCCTGGGGtAGGCAGAGGCAGTTGAGGATCATGAAATAACTATG
        <<<<<<<<<<<<<<<<<<<
```

16) Whole sequence ::: rs11909758-rs9980111 (159 bp long ) AC/AT /CT

TGCAATGAAACTCAAAAGAGAAAAGTTAACAGGTGCAAaAGGTAGTTTTATTATAAAAGG
AGGGTAGGCAACAAGAATATGTTTAATTTTTCTTCCTTTTCATGAGTAAGGACAAGAGTg
TCATATATGTGaatatttttatttaattttaaGTAGAAATCTGTTTTTAAAATATGGG (SEQ ID NO: 49)

```
OLIGO              (SEQ ID NOs: 50, 51)
LEFT PRIMER         6    20   49.91   30.00   3.00   0.00
TGAAACTCAAAAGAGAAAAG
RIGHT PRIMER      164    20   42.77   20.00   6.00   4.00
ACAGATTTCTACttaaaatt
SEQUENCE SIZE: 178
INCLUDED REGION SIZE: 178
```

PRODUCT SIZE: 159, PAIR ANY COMPL: 6.00, PAIR 3' COMPL: 3.00

```
    1 TGCAATGAAACTCAAAAGAGAAAAGTTAACAGGTGCAAaAGGTAGTTTTATTATAAAAGG
        >>>>>>>>>>>>>>>>>>>>

61 AGGGTAGGCAACAAGAATATCTTTAATTTTTCTTCCTTTTCATGAGTAAGGACAAGAGTg

121 TCATATATCTGaatatttttatttaattttaaGTAGAAATCTCTTTTTAAAATATGGG
                                    <<<<<<<<<<<<<<<<<<<<
```

17) Whole sequence ::: rs854613-rs854614  AA/AG/TG

CCACCATTCATCAAAACTTTGATACTGGACTCAATTGTGAATTTGaCTTGAAATTTGATA
ATGCTTTTGTTTTACTgTTCTGCTCAGCAAAATAGTACATGT (SEQ ID NO: 52)

```
OLIGO              (SEQ ID NOs: 53, 54)
LEFT PRIMER        12    20   49.40   35.00   6.00   1.00
CAAAACTTTGATACTGGACT
RIGHT PRIMER      102    19   46.05   31.58   6.00   1.00
ACATGTACTATTTTGCTGA
SEQUENCE SIZE: 102
INCLUDED REGION SIZE: 102
```

PRODUCT SIZE: 91, PAIR ANY COMPL: 5.00, PAIR 3' COMPL: 1.00

```
    1 CCACCATTCATCAAAACTTTGATACTGGACTCAATTGTGAATTTGaCTTGAAATTTGATA
                  >>>>>>>>>>>>>>>>>>>>

61 ATGCTTTTGTTTTACTgTTCTGCTCAGCAAAATAGTACATGT
                            <<<<<<<<<<<<<<<<<<<
```

3rd group---order primers from 18 - 25

18) Whole sequence ::: rs2826225-rs2826226  AA/GA/GC

GCCTGCATAAAGTGAGGATGGTGTAGTAATTGGGTATCTCCAGTTATAAACACAAaAAGC
ATGATAGAGCTGGGAcTGTGATTGCAGGAAAGCAATAGTCACTCCAAAAGGAGATCCTCA
TGATATGAATACGGAAGAAACAATATTTCCTGCTAATGTAGTAGCC (SEQ ID NO: 55)

FIG. 6I

```
OLIGO                (SEQ ID NOs: 56, 57)
LEFT PRIMER              2   20    58.17   50.00   4.00   0.00
CCTGCATAAAGTGAGGATGG
RIGHT PRIMER           120   21    59.27   47.62   6.00   0.00
TGAGGATCTCCTTTTGGAGTG
SEQUENCE SIZE: 166
INCLUDED REGION SIZE: 166

PRODUCT SIZE: 119, PAIR ANY COMPL: 6.00, PAIR 3' COMPL: 3.00

1 GCCTGCATAAAGTGAGGATGGTGTAGTAATTGGGTATCTCCAGTTATAAACACAAaAAGC
      >>>>>>>>>>>>>>>>>>>>
   61 ATGATAGAGCTGGGAcTGTGATTCCAGGAAAGCAATAGTCACTCCAAAAGGAGATCCTCA
                                              <<<<<<<<<<<<<<<<<<<<<
  121 TGATATGAATACGGAAGAAACAATATTTCCTGCTAATGTAGTAGCC
```

19) Whole sequence ::: rs2826842-rs232414 CA/CG/TA/TG

```
GCAAAGGGGTACTCTATGTAATGAAcATgacctggcagtactgacatctcctgagggact
gttagaagtgcagactcttgtatctttctcaagtctatgaaatctagacttcattttaa
caagatgacccgatatttacatacacattaaagt (SEQ ID NO: 58)

OLIGO                (SEQ ID NOs: 59, 60)
LEFT PRIMER              1   20    52.04   45.00   4.00   2.00
GCAAAGGGGTACTCTATGTA
RIGHT PRIMER           135   20    53.29   35.00   4.00   3.00
tatcgggtcatcttgttaaa
SEQUENCE SIZE: 154
INCLUDED REGION SIZE: 154

PRODUCT SIZE: 135, PAIR ANY COMPL: 3.00, PAIR 3' COMPL: 2.00

1 GCAAAGGGGTACTCTATGTAATGAAcATgacctggcagtactgacatctcctgagggact
      >>>>>>>>>>>>>>>>>>>>
   61 gttagaagtgcagactcttgtatctttctcaagtctatgaaatctagacttcattttaa
                                                             <<<<<
  121 caagatgacccgatatttacatacacattaaagt
      <<<<<<<<<<<<<<<
```

20) Whole sequence ::: rs1980969-rs1980970 AA/AG/TA/TG

```
GTATCTAACAAAGCTCTGTCCAAAATTTTGAATTTCTCGTTAAAaGCATCATGATTATAG
AACAGAGGTTACAATCAATTATTCAGTCACACAATCACTCTCATCAGTCATTAAGGTGCg
TACCTGGTGTTCCAGTTATTCAGTGTGGTATAACAAACTACCTGGAACTTAATG (SEQ ID NO: 61)

OLIGO                (SEQ ID NOs: 62, 63)
LEFT PRIMER              4   22    56.88   36.36   8.00   2.00
TCTAACAAAGCTCTGTCCAAAA
RIGHT PRIMER           148   21    56.12   42.86   3.00   1.00
CCACACTGAATAACTGGAACA
SEQUENCE SIZE: 174
INCLUDED REGION SIZE: 174
```

FIG. 6J

PRODUCT SIZE: 145, PAIR ANY COMPL: 4.00, PAIR 3' COMPL: 1.00

```
  1 GTATCTAACAAAGCTCTGTCCAAAATTTTGAATTTCTCGTTAAAaGCATCATGATTATAG
      >>>>>>>>>>>>>>>>>>>>>>

61 AACAGAGGTTACAATCAATTATTCAGTCACACAATCACTCTCATCAGTCATTAAGGTGCg

121 TACCTGGTGTTCCAGTTATTCAGTGTGGTATAACAAACTACCTGGAACTTAATG
      <<<<<<<<<<<<<<<<<<<<
```

4<sup>th</sup> group

21) Whole sequence ::: rs189900-rs2221492

AGAGTGGTTAAGTGACTTGATCAATTCCTCA GGTGGGGATTCAAGCTCTTAAAGCTGTAG
ACTATGTCGTCCAAACAAAcACTGACATGAATATGACTTCCAATAGGCAAGAAAAGAGGC
CTAGGTCgAGATACTGCAAGACATGCAAGCAATCTAGTAATGGCATAAAACCTGCTATCC
GAATTGGCTAAAATTATGTATT (SEQ ID NO: 64)

```
OLIGO            (SEQ ID NOs: 65, 66)
LEFT PRIMER          32    20    59.13    50.00    4.00    2.00
GGTGGGGATTCAAGCTCTTA
RIGHT PRIMER        180    22    59.38    40.91    5.00    3.00
GGATAGCAGGTTTTATGCCATT
SEQUENCE SIZE: 202
INCLUDED REGION SIZE: 202
```

PRODUCT SIZE: 149, PAIR ANY COMPL: 4.00, PAIR 3' COMPL: 1.00

```
  1 AGAGTGGTTAAGTGACTTGATCAATTCCTCAGGTGGGGATTCAAGCTCTTAAAGCTGTAG
                                   >>>>>>>>>>>>>>>>>>>>

61 ACTATGTCGTCCAAACAAAcACTGACATGAATATGACTTCCAATAGGCAAGAAAAGAGGC

121 CTAGGTCgAGATACTGCAAGACATGCAAGCAATCTAGTAATGGCATAAAACCTGCTATCC
                                         <<<<<<<<<<<<<<<<<<<<<<

181 GAATTGGCTAAAATTATGTATT
```

22) Whole sequence ::: rs2827920-rs2827921

TTCTTTCTCACACAATGGGTTCCATTCCCACTACTACTCCATTCAAATTGAAGTGCCTTC
aATGATTATTAAAAAACTCTCTTTAAAATAGCTCAcGTAACCTTACATCCTTTGACTGAG
GCTCAACTCATGTCAATGCTTCAGTATCAACTTTTC (SEQ ID NO: 67)

```
OLIGO            (SEQ ID NOs: 68, 69)
LEFT PRIMER          14    21    59.93    47.62    7.00    0.00
AATGGGTTCCATTCCCACTAC
RIGHT PRIMER        125    20    58.96    50.00    7.00    1.00
TGAGCCTCAGTCAAAGGATG
SEQUENCE SIZE: 156
INCLUDED REGION SIZE: 156
```

FIG. 6K

PRODUCT SIZE: 112, PAIR ANY COMPL: 4.00, PAIR 3' COMPL: 1.00

```
  1 TTCTTTCTCACACAATGGGTTCCATTCCCACTACTACTCCATTCAAATTGAAGTGCCTTC
    >>>>>>>>>>>>>>>>>>>>>

61 aATGATTATTAAAAAACTCTCTTTAAAATAGCTCAcGTAACCTTACATCCTTTGACTGAG
                                           <<<<<<<<<<<<<<

121 GCTCAACTCATGTCAATGCTTCAGTATCAACTTTTC
    <<<<<
```

23) Whole sequence ::: rs198047-rs2827935

ATTTGTAATAACATTTAGTAAGTATTTATTTGAGGAGTTTGAATTTTGTTCTTGTTTATC
TTGTTCTCTTTCTTcGTAGATTAGTTGGTGTTAACATCAATAGGATAACCCTTTCTTTCA
GCATATGTGAATGAAATaAACCAATTATTGCCACTTTCCAGGTTAACCAGAATATACATA
GATACGAGGACAGTGGACTGTT (SEQ ID NO: 70)

OLIGO           (SEQ ID NOs: 71, 72)
LEFT PRIMER         30    22    56.07    31.82    4.00    1.00
TTGAGGAGTTTGAATTTTGTTC
RIGHT PRIMER       164    20    57.22    40.00    3.00    1.00
AACCTGGAAAGTGGCAATAA
SEQUENCE SIZE: 202
INCLUDED REGION SIZE: 202

PRODUCT SIZE: 135, PAIR ANY COMPL: 3.00, PAIR 3' COMPL: 2.00

```
  1 ATTTGTAATAACATTTAGTAAGTATTTATTTGAGGAGTTTGAATTTTGTTCTTGTTTATC
                                 >>>>>>>>>>>>>>>>>>>>>>

61 TTGTTCTCTTTCTTcGTAGATTAGTTGGTGTTAACATCAATAGGATAACCCTTTCTTTCA

121 GCATATGTGAATGAAATaAACCAATTATTGCCACTTTCCAGGTTAACCAGAATATACATA
                                         <<<<<<<<<<<<<<<<<<<<

181 GATACGAGGACAGTGGACTGTT
```

24) Whole sequence ::: rs9978999-rs9979175 tagggcagagagagcaagcaagctctctaccttctcatataagggcactaatcccaccat
gaaggcgccactgtcatgacCtgattatgtcacaaagaccccggggcaaatattaccact
Gtgaggagtacagttttagcatgtgaattttggaagaacacaaacatttag (SEQ ID NO: 73)

OLIGO           (SEQ ID NOs: 74, 75)
LEFT PRIMER         14    21    58.50    52.38    4.00    0.00
gcaagcaagctctctaccttc
RIGHT PRIMER       160    22    59.98    36.36    4.00    2.00
tgttcttccaaaattcacatgc
SEQUENCE SIZE: 171
INCLUDED REGION SIZE: 171

PRODUCT SIZE: 147, PAIR ANY COMPL: 3.00, PAIR 3' COMPL: 0.00

```
  1 tagggcagagagagcaagcaagctctctaccttctcatataagggcactaatcccaccat
```

FIG. 6L

```
                >>>>>>>>>>>>>>>>>>>>>
    61 gaaggcgccactgtcatgacCtgattatgtcacaaagaccccggggcaaatattaccact 121 Gtgaggagtacagtttttagcatgtgaatttttggaagaacacaaacatttag
                     <<<<<<<<<<<<<<<<<<<<
```

25) Whole sequence ::: rs1034346-rs12481852

ATTCTAATTTTAAATATCATTGATGTAGAACATTCTATTTCACTATTCCTTCATTTTATT
aTTATGGGAAATTATATACAGTTCTCCAGATTTTTAAAGCCTTGCTAACATGTTTTAAGT
CACACAAATATTCTcCTGTGGGAAAATGACAGTAATTTAGTGTGCAACAATTATATAGAA
CTATTTTTCAAACTT (SEQ ID NO: 76)

```
OLIGO              (SEQ ID NOs: 77, 78)
LEFT PRIMER         37    21    50.04   23.81   2.00   0.00
ATTTCACTATTCCTTCATTTT
RIGHT PRIMER       173    22    50.19   27.27   6.00   3.00
TAATTGTTGCACACTAAATTAC
SEQUENCE SIZE: 195
INCLUDED REGION SIZE: 195
```

PRODUCT SIZE: 137, PAIR ANY COMPL: 4.00, PAIR 3' COMPL: 2.00

```
     1 ATTCTAATTTTAAATATCATTGATGTAGAACATTCTATTTCACTATTCCTTCATTTTATT
                                         >>>>>>>>>>>>>>>>>>>>>

61 aTTATGGGAAATTATATACAGTTCTCCAGATTTTTAAAGCCTTGCTAACATGTTTTAAGT

121 CACACAAATATTCTcCTGTGGGAAAATGACAGTAATTTAGTGTGCAACAATTATATAGAA
                         <<<<<<<<<<<<<<<<<<<<<

181 CTATTTTTCAAACTT
```

5th group

26) Whole sequence ::: rs7509629-rs2828358

ACTGTCATGGACTTAAACAATTGTCTTTGAATTGTCTTTTTTCATACTTTTATTTGCATC
TTTcCACTAAAAAGATGgCACAAAGTAATCCTAGTTTACATTTTTTACCATGTAATTCCA
TATTACTTTTTCCTGAAA (SEQ ID NO: 79)

```
OLIGO              (SEQ ID NOs: 80, 81)
LEFT PRIMER          1    20    50.46   35.00   4.00   0.00
ACTGTCATGGACTTAAACAA
RIGHT PRIMER       137    22    53.49   27.27   4.00   0.00
TTCAGGAAAAGTAATATGGAA
SEQUENCE SIZE: 138
INCLUDED REGION SIZE: 138
```

PRODUCT SIZE: 137, PAIR ANY COMPL: 4.00, PAIR 3' COMPL: 0.00

```
     1 ACTGTCATGGACTTAAACAATTGTCTTTGAATTGTCTTTTTTCATACTTTTATTTGCATC
       >>>>>>>>>>>>>>>>>>>>
```

FIG. 6M

```
 61 TTTcCACTAAAAAGATGgCACAAAGTAATCCTAGTTTACATTTTTTACCATGTAATTCCA
                                                           <<<<<

121 TATTACTTTTTCCTGAAA
    <<<<<<<<<<<<<<<<<<
```

6<sup>th</sup> group

27) Whole sequence ::: rs4817013-rs7277036 aaagaaaaaaaagccacagaaatcagtcctagagaaaacCgatctatgagctgcctgaAa
ataattataaaataactatcataaaaatgcccagtgagatataagaaaacacagacaac (SEQ ID
NO: 82)

```
OLIGO              (SEQ ID NOs: 83, 84)
LEFT PRIMER         8      21    56.10    38.10   4.00   2.00
aaaaagccacagaaatcagtc
RIGHT PRIMER      107      22    55.60    36.36   4.00   2.00
ttcttatatctcactgggcatt
SEQUENCE SIZE: 119
INCLUDED REGION SIZE: 119
```

PRODUCT SIZE: 100, PAIR ANY COMPL: 5.00, PAIR 3' COMPL: 1.00

```
  1 aaagaaaaaaaagccacagaaatcagtcctagagaaaacCgatctatgagctgcctgaAa
    >>>>>>>>>>>>>>>>>>>>>

61 ataattataaaataactatcataaaaatgcccagtgagatataagaaaacacagacaac
                                        <<<<<<<<<<<<<<<<<<<<<<
```

28) Whole sequence ::: rs9981121-rs2829696

CAAGGTCAGAGAAGTTATCTTGGATGGTACAACAGAAGAAAGGAGAAGAAaGGATAAGCA
GAAAATCAAAAGGGCATAAAAAAATTACTGGgGAAAATAATTCTTAGTCACTCACCATT
TCTTATGTTTGTGAAAACAGAAA (SEQ ID NO: 85)

```
OLIGO              (SEQ ID NOs: 86, 87)
LEFT PRIMER        22      22    56.24    45.45   2.00   0.00
GGATGGTAGAAGAGAAGAAAGG
RIGHT PRIMER      134      22    55.74    31.82   4.00   1.00
TCACAAACATAAGAAATGGTGA
SEQUENCE SIZE: 143
INCLUDED REGION SIZE: 143
```

PRODUCT SIZE: 113, PAIR ANY COMPL: 3.00, PAIR 3' COMPL: 0.00

```
  1 CAAGGTCAGAGAAGTTATCTTGGATGGTAGAAGAGAAGAAAGGAGAAGAAaGGATAAGCA
                          >>>>>>>>>>>>>>>>>>>>>>

61 GAAAATCAAAAGGGCATAAAAAAATTACTGGgGAAAATAATTCTTAGTCACTCACCATT
                                                    <<<<<<<<

121 TCTTATGTTTGTGAAAACAGAAA
    <<<<<<<<<<<<<<
```

29) Whole sequence ::: rs455921-rs2898102

FIG. 6N gaccacaattcacaaatgcaaagatgcagaaccaacctaagtggccaCtgactaatgaga
ggataaagaagatgtggcatatataTatcagggactactactcagccattacaaggaaca
aaataatgtcttttgc (SEQ ID NO: 88)

```
OLIGO              (SEQ ID NOs: 89, 90)
LEFT PRIMER            17    20   59.85   45.00   4.00   0.00
tgcaaagatgcagaaccaac
RIGHT PRIMER          123    22   59.63   36.36   2.00   1.00
ttttgttccttgtaatggctga
SEQUENCE SIZE: 136
INCLUDED REGION SIZE: 136
```

PRODUCT SIZE: 107, PAIR ANY COMPL: 5.00, PAIR 3' COMPL: 1.00

```
    1 gaccacaattcacaaatgcaaagatgcagaaccaacctaagtggccaCtgactaatgaga
                   >>>>>>>>>>>>>>>>>>>>

61 ggataaagaagatgtggcatatataTatcagggactactactcagccattacaaggaaca
                                              <<<<<<<<<<<<<<<<<

121 aaataatgtcttttgc
          <<<
```

30) Whole sequence ::: rs2898102- rs458848 gaccacaattcacaaatgcaaagatgcagaaccaacctaagtggccactgactaatgaga
ggataaagaagatgtggcatatataCatcagggactactTctcagccattacaaggaaca
aaataatgtcttttgcaacaacttggatagagctggaggc (SEQ ID NO: 91)

```
OLIGO              (SEQ ID NOs: 92, 93)
LEFT PRIMER            17    20   59.85   45.00   4.00   0.00
tgcaaagatgcagaaccaac
RIGHT PRIMER          160    21   59.86   52.38   4.00   3.00
gcctccagctctatccaagtt
SEQUENCE SIZE: 160
INCLUDED REGION SIZE: 160
```

PRODUCT SIZE: 144, PAIR ANY COMPL: 4.00, PAIR 3' COMPL: 3.00

```
    1 gaccacaattcacaaatgcaaagatgcagaaccaacctaagtggccactgactaatgaga
                   >>>>>>>>>>>>>>>>>>>>

61 ggataaagaagatgtggcatatataCatcagggactactTctcagccattacaaggaaca 121 aaataatgtcttttgcaacaacttggatagagctggaggc
                            <<<<<<<<<<<<<<<<<<<<<
```

31) Whole sequence ::: rs961301-rs2830208

AATCCTAGACCTTGGATTGCAAGAGACTCCTTAATATCTTCCCATGTCCACATTTcCTTC
ACATAGTTTGAATGTGGCTTCTATTATATACAGATACAAGATTCAAATCCAACCTCTAtG
ATGACTGGTCTTGTGAATAAGCAGAAGAGGCACTAACAAT (SEQ ID NO: 94)

```
OLIGO              (SEQ ID NOs: 95, 96)
```

FIG. 6O

```
LEFT PRIMER              29    22    57.95    40.91    4.00    2.00
CCTTAATATCTTCCCATGTCCA
RIGHT PRIMER            160    22    57.35    40.91    3.00    0.00
ATTGTTAGTGCCTCTTCTGCTT
SEQUENCE SIZE: 160
INCLUDED REGION SIZE: 160

PRODUCT SIZE: 132, PAIR ANY COMPL: 3.00, PAIR 3' COMPL: 1.00

1 AATCCTAGACCTTGGATTGCAAGAGACTCCTTAATATCTTCCCATGTCCACATTTcCTTC
                                  >>>>>>>>>>>>>>>>>>>>>>

61 ACATAGTTTGAATGTGGCTTCTATTATATACAGATACAAGATTCAAATCCAACCTCTAtG

121 ATGACTGGTCTTGTGAATAAGCAGAAGAGGCACTAACAAT
                          <<<<<<<<<<<<<<<<<<<<<<

32) Whole sequence ::: rs2174536-rs458076

AAGAGAAGTGAGGTCAGCAGCTGCAAGCCACCTCCGTCATTTAGAAAAGCTTCaTGATGT
AGTGTGTCGTTTCGATGTGACACTGTCTCACAGAGTTAAAATGATGTtAAGGAACTGTTC
AATGGAAATTTAGAAATTTCTCTTTTTCTCAATTTTAGTGTA (SEQ ID NO: 97)

OLIGO                 (SEQ ID NOs: 98, 99)
LEFT PRIMER               3    20    57.31    55.00    5.00    5.00
GAGAAGTGAGGTCAGCAGCT
RIGHT PRIMER            136    22    53.92    27.27    6.00    2.00
TTTCTAAATTTCCATTGAACAG
SEQUENCE SIZE: 162
INCLUDED REGION SIZE: 162

PRODUCT SIZE: 134, PAIR ANY COMPL: 4.00, PAIR 3' COMPL: 2.00

1 AAGAGAAGTGAGGTCAGCAGCTGCAAGCCACCTCCGTCATTTAGAAAAGCTTCaTGATGT
         >>>>>>>>>>>>>>>>>>>>

61 AGTGTGTCGTTTCGATGTGACACTGTCTCACAGAGTTAAAATGATGTtAAGGAACTGTTC
                                                          <<<<<<

121 AATGGAAATTTAGAAATTTCTCTTTTTCTCAATTTTAGTGTA
         <<<<<<<<<<<<<<<<

33) Whole sequence ::: rs432557-rs1012766

ATGGCTGAATAGTATTCCCTTGTGTATATATCTaTTTATCCTTTTATTCATTGATGGACA
CTTAGGCTGATTTTCTCTCTTCTCATGGCTGGCTTCTCATCACCCTTTGGTCCTCCTGTA
TCCTCgTGTAATAAAGCTCTTCCCCAATATCTCGATAGAT (SEQ ID NO: 100)

OLIGO                 (SEQ ID NOs: 101, 102)
LEFT PRIMER               3    22    57.77    45.45    9.00    0.00
GGCTGAATAGTATTCCCTTGTG
RIGHT PRIMER            155    20    59.22    50.00    4.00    2.00
TCGAGATATTGGGGAAGAGC
SEQUENCE SIZE: 160
INCLUDED REGION SIZE: 160
```

FIG. 6P

PRODUCT SIZE: 153, PAIR ANY COMPL: 5.00, PAIR 3' COMPL: 1.00

```
  1 ATGGCTGAATAGTATTCCCTTGTGTATATATCTaTTTATCCTTTTATTCATTGATGGACA
    >>>>>>>>>>>>>>>>>>>>>>

61 CTTAGGCTGATTTTCTCTCTTCTCATGGCTGGCTTCTCATCACCCTTTGGTCCTCCTGTA

121 TCCTCgTGTAATAAAGCTCTTCCCCAATATCTCGATAGAT
                       <<<<<<<<<<<<<<<<<<<<
```

34) Whole sequence ::: rs10222076-rs10222075 cattttaacttgatta cctccacaaagactattccagaataaggttatgttctgaggtat
taggggttacAacttcaacatatgaattttgagtggacacaattcaacccatagcaCCTC
CGTGTAAGAGCTGGGAAGGGAAAGTGGCTAAGTTGTGCAAATGTGCACATTGGTTGGAGA
TGATTAACTTCTGGCATGT (SEQ ID NO: 103)

```
OLIGO            (SEQ ID NOs: 104, 105)
LEFT PRIMER            17    22    58.32    45.45    4.00    2.00
cctccacaaagactattccaga
RIGHT PRIMER          146    20    60.76    55.00    4.00    2.00
CACTTTCCCTTCCCAGCTCT
SEQUENCE SIZE: 199
INCLUDED REGION SIZE: 199
```

PRODUCT SIZE: 130, PAIR ANY COMPL: 4.00, PAIR 3' COMPL: 3.00

```
  1 cattttaacttgattacctccacaaagactattccagaataaggttatgttctgaggtat
                   >>>>>>>>>>>>>>>>>>>>>>

61 taggggttacAacttcaacatatgaattttgagtggacacaattcaacccatagcaCCTC

121 CGTGTAAGAGCTGGGAAGGGAAAGTGGCTAAGTTGTGCAAATGTGCACATTGGTTGGAGA
                       <<<<<<<<<<<<<<<<<<<<

181 TGATTAACTTCTGGCATGT
```

35) Whole sequence ::: rs11088023-rs11088024 aggggggaaattggcaatctgattctaaaattcataCggaaaaaaacaatggagttagaat
aactaaaacaagtccgaaaaagaaaaagaaatggaggactaatgctacctgatttcaagt
cttatcTtataaatctacatcaataaaggacaagttg (SEQ ID NO: 106)

```
OLIGO            (SEQ ID NOs: 107, 108)
LEFT PRIMER             6    20    54.34    35.00    7.00    3.00
gaaattggcaatctgattct
RIGHT PRIMER          157    21    51.94    33.33    5.00    0.00
caacttgtcctttattgatgt
SEQUENCE SIZE: 157
INCLUDED REGION SIZE: 157
```

PRODUCT SIZE: 152, PAIR ANY COMPL: 4.00, PAIR 3' COMPL: 0.00

```
  1 aggggggaaattggcaatctgattctaaaattcataCggaaaaaaacaatggagttagaat
```

FIG. 6Q

```
                >>>>>>>>>>>>>>>>>>>>>
   61 aactaaaacaagtccgaaaaagaaaaagaaatggaggactaatgctacctgatttcaagt 121 cttatcTtataaatctacatcaataaaggacaagttg
                <<<<<<<<<<<<<<<<<<<<
```

36) Whole sequence ::: rs1011734-rs1011733

TCTGTGTTTGTCTATGTTGATAAAACATTGAAATGCCAaATAGCTCAAAGGTCATTCACT
TAAGAAATCTAAGTACTGATAACATCTTAGCCCCGATTCTTCATAGGCATTGTTAAGCCT
ATTATAATTTTGGTtCAGAGAGAAGGTAAACTATATTCCAGACAGGCATATAA (SEQ ID NO: 109)

```
OLIGO             (SEQ ID NOs: 110, 111)
LEFT PRIMER        12    22    50.06    22.73    6.00    2.00
CTATGTTGATAAAACATTGAAA
RIGHT PRIMER      167    20    51.09    40.00    4.00    2.00
GCCTGTCTGGAATATAGTTT
SEQUENCE SIZE: 173
INCLUDED REGION SIZE: 173
```

PRODUCT SIZE: 156, PAIR ANY COMPL: 5.00, PAIR 3' COMPL: 3.00

```
    1 TCTGTGTTTGTCTATGTTGATAAAACATTGAAATGCCAaATAGCTCAAAGGTCATTCACT
                 >>>>>>>>>>>>>>>>>>>>>>

61 TAAGAAATCTAAGTACTGATAACATCTTAGCCCCGATTCTTCATAGGCATTGTTAAGCCT

121 ATTATAATTTTGGTtCAGAGAGAAGGTAAACTATATTCCAGACAGGCATATAA
                                      <<<<<<<<<<<<<<<<<<<<
```

37) Whole sequence ::: rs2831244-rs9789838

TGCAGGGCATATAATCTAAGCTGTAAACGTCCTGTcAGAAGACAACATATTCATCTTGCT
AAGGTtTAAGCTATATGACTGGCACTGTGCTCAACTCAGAGTCATTGAATGAACAGTATT
TATTTA (SEQ ID NO: 112)

```
OLIGO             (SEQ ID NOs: 113, 114)
LEFT PRIMER         3    22    55.40    40.91    5.00    3.00
CAGGGCATATAATCTAAGCTGT
RIGHT PRIMER      107    21    55.99    47.62    7.00    2.00
CAATGACTCTGAGTTGAGCAC
SEQUENCE SIZE: 126
INCLUDED REGION SIZE: 126
```

PRODUCT SIZE: 105, PAIR ANY COMPL: 4.00, PAIR 3' COMPL: 2.00

```
    1 TGCAGGGCATATAATCTAAGCTGTAAACGTCCTGTcAGAAGACAACATATTCATCTTGCT
        >>>>>>>>>>>>>>>>>>>>>>

61 AAGGTtTAAGCTATATGACTGGCACTGTGCTCAACTCAGAGTCATTGAATGAACAGTATT
                                     <<<<<<<<<<<<<<<<<<<<<

121 TATTTA
```

FIG. 6R

38) Whole sequence ::: rs8132769-rs2831440

TTCACATTATTCCCTTAAAATAAACTCTCTCCCTCCCCTCTCCCGTCTCAaCCTTGTCCC
TTTCTTTATATAATGGGTAATtCGTTAATGTCAGCAGAATAGTTTTGGGGCCATAATGGC
AAGTATCACGTG (SEQ ID NO: 115)

```
OLIGO              (SEQ ID NOs: 116, 117)
LEFT PRIMER          23    19    56.84    57.89    1.00    0.00
AACTCTCTCCCTCCCCTCT
RIGHT PRIMER        115    20    56.24    40.00    4.00    2.00
TATGGCCCCAAAACTATTCT
SEQUENCE SIZE: 132
INCLUDED REGION SIZE: 132
```

PRODUCT SIZE: 93, PAIR ANY COMPL: 2.00, PAIR 3' COMPL: 0.00

```
   1 TTCACATTATTCCCTTAAAATAAACTCTCTCCCTCCCCTCTCCCGTCTCAaCCTTGTCCC
                          >>>>>>>>>>>>>>>>>>>

61 TTTCTTTATATAATGGGTAATtCGTTAATGTCAGCAGAATAGTTTTGGGGCCATAATGGC
                                          <<<<<<<<<<<<<<<<<<<<

121 AAGTATCACGTG
```

39) Whole sequence ::: rs8134080-rs2831524

TCAGGAAGCAACAAGTACTGGGCAGATTGATACTGTAGCTaGGCTCTAGCTCTATACCTC
TAGAATaaatgttacaaactagcaacttgaaagctaaacctggcccacag (SEQ ID NO: 118)

```
OLIGO              (SEQ ID NOs: 119, 120)
LEFT PRIMER          11    20    55.75    45.00    6.00    2.00
ACAAGTACTGGGCAGATTGA
RIGHT PRIMER        104    20    56.27    45.00    4.00    2.00
gccaggtttagctttcaagt
SEQUENCE SIZE: 110
INCLUDED REGION SIZE: 110
```

PRODUCT SIZE: 94, PAIR ANY COMPL: 4.00, PAIR 3' COMPL: 3.00

```
   1 TCAGGAAGCAACAAGTACTGGGCAGATTGATACTGTAGCTaGGCTCTAGCTCTATACCTC
                >>>>>>>>>>>>>>>>>>>>

61 TAGAATaaatgttacaaactagcaacttgaaagctaaacctggcccacag
                              <<<<<<<<<<<<<<<<<<<<
```

40) Whole sequence ::: rs4817219-rs4817220 tggttcttgagaatttatatcaggagaaacactgtcagtCtgtattgaaaggaacagag
aaaatTcgaaattaaagaagactattaaacctccaaaattctggca (SEQ ID NO: 121)

```
OLIGO              (SEQ ID NOs: 122, 123)
LEFT PRIMER          14    22    51.54    31.82    4.00    3.00
ttttatatcaggagaaacactg
```

FIG. 6S

```
RIGHT PRIMER       104    21    55.03    33.33    8.00    2.00
ccagaattttggaggtttaat
SEQUENCE SIZE: 106
INCLUDED REGION SIZE: 106

PRODUCT SIZE: 91, PAIR ANY COMPL: 4.00, PAIR 3' COMPL: 2.00

1 tggttcttgagaattttatatcaggagaaacactgtcagtCtgtattgaaaggaacagag
      >>>>>>>>>>>>>>>>>>>>>

61 aaaatTcgaaattaaagaagactattaaacctccaaaattctggca
                            <<<<<<<<<<<<<<<<<<<<<
```

41) Whole sequence ::: rs2250911-rs2250997

GCATCAAACTACACACTGTCATTCCTCCTTTATCTCCAAAAGCTTGAAAATTCCTCACTT
GTaTCTCATTCTTTCTCTCTTAGAAAACTGATCACCTCTGATGAATTAgAACGGAATGAC
CAAGCTTTGGGAGAGGCAAAAGAATCTCGGTGTTAAAGACTCAGAGTTTAA (SEQ ID NO: 124)

```
OLIGO         (SEQ ID NOs: 125, 126)
LEFT PRIMER        17    22    58.65    40.91    3.00    0.00
TGTCATTCCTCCTTTATCTCCA
RIGHT PRIMER      144    20    59.42    45.00    4.00    2.00
TTCTTTTGCCTCTCCCAAAG
SEQUENCE SIZE: 171
INCLUDED REGION SIZE: 171

PRODUCT SIZE: 128, PAIR ANY COMPL: 4.00, PAIR 3' COMPL: 0.00

1 GCATCAAACTACACACTGTCATTCCTCCTTTATCTCCAAAAGCTTGAAAATTCCTCACTT
                     >>>>>>>>>>>>>>>>>>>>>>

61 GTaTCTCATTCTTTCTCTCTTAGAAAACTGATCACCTCTGATGAATTAgAACGGAATGAC

121 CAAGCTTTGGGAGAGGCAAAAGAATCTCGGTGTTAAAGACTCAGAGTTTAA
         <<<<<<<<<<<<<<<<<<<<
```

42) Whole sequence ::: rs2831899-rs2831900

TTGAAAATTAAGAAACCCTGGCACAGTGTTGACTGGAGCCaCTTACCTTAATAGAAAATA
AAGCTCACATATATCCATAATGAAAAGCAGAGACCAGCACAACCATAGTCACCTGACAGT
TTtAAAATCCAAGGCCAGGATCTTCTCAACTCAGGCCCACTCA (SEQ ID NO: 127)

```
OLIGO         (SEQ ID NOs: 128, 129)
LEFT PRIMER        15    20    60.63    55.00    6.00    2.00
ACCCTGGCACAGTGTTGACT
RIGHT PRIMER      159    20    59.80    50.00    4.00    2.00
TGGGCCTGAGTTGAGAAGAT
SEQUENCE SIZE: 163
INCLUDED REGION SIZE: 163

PRODUCT SIZE: 145, PAIR ANY COMPL: 5.00, PAIR 3' COMPL: 1.00

1 TTGAAAATTAAGAAACCCTGGCACAGTGTTGACTGGAGCCaCTTACCTTAATAGAAAATA
                     >>>>>>>>>>>>>>>>>>>>
```

FIG. 6T

```
 61 AAGCTCACATATATCCATAATGAAAAGCAGAGACCAGCACAACCATAGTCACCTGACAGT

121 TTtAAAATCCAAGGCCAGGATCTTCTCAACTCAGGCCCACTCA
    <<<<<<<<<<<<<<<<<<<<
```

43) Whole sequence ::: rs2831902-rs2831903

```
CACATAACTAATAAATTTGTAAGTATGTGCAACGGCTCACaCTTGCTTCCAGAATGGCAC
CTAAAAAACAGATTTACCTCTCCCCAAATTCAGATATGGAATTAAATGTAATGTCAGGAA
AAcTGTCTAAGAGTTGGAAATGGGAAAAAAATGTTCTTTTGGT (SEQ ID NO: 212)

OLIGO              (SEQ ID NOs: 213, 130)
LEFT PRIMER           14     21    53.16   33.33   4.00   2.00
AATTTCTAAGTATGTGCAACG
RIGHT PRIMER         149     20    56.27   35.00   2.00   0.00
TTTTTCCCATTTCCAACTCT
SEQUENCE SIZE: 163
INCLUDED REGION SIZE: 163

PRODUCT SIZE: 136, PAIR ANY COMPL: 4.00, PAIR 3' COMPL: 2.00

1 CACATAACTAATAAATTTGTAAGTATGTGCAACGGCTCACaCTTGCTTCCAGAATGGCAC
                   >>>>>>>>>>>>>>>>>>>>

61 CTAAAAAACAGATTTACCTCTCCCCAAATTCAGATATGGAATTAAATGTAATGTCAGGAA

121 AAcTGTCTAAGAGTTGGAAATGGGAAAAAAATGTTCTTTTGGT
                      <<<<<<<<<<<<<<<<<<<<
```

44) Whole sequence ::: rs11088086-rs2251447

```
AAAAAAAAAGATGAGACAGGCAGGTGCGAAAGAAATAAAAGTCAaAACTGATCCAGTTGG
GAAACTCAGAATTGACAGTTAcGTGTCCTTTCATTTATTGATATTTTGAGATTCACAGGG
GT (SEQ ID NO: 131)

OLIGO              (SEQ ID NOs: 132, 133)
LEFT PRIMER            6     20    56.41   45.00   2.00   2.00
AAAAGATGAGACAGGCAGGT
RIGHT PRIMER         122     20    55.99   40.00   5.00   2.00
ACCCTGTGAATCTCAAAAT
SEQUENCE SIZE: 122
INCLUDED REGION SIZE: 122

PRODUCT SIZE: 117, PAIR ANY COMPL: 5.00, PAIR 3' COMPL: 2.00

1 AAAAAAAAAGATGAGACAGGCAGGTGCGAAAGAAATAAAAGTCAaAACTGATCCAGTTGG
          >>>>>>>>>>>>>>>>>>>>

61 GAAACTCAGAATTGACAGTTAcGTGTCCTTTCATTTATTGATATTTTGAGATTCACAGGG
                                         <<<<<<<<<<<<<<<<<<<<

121 GT
      <<
```

45) Whole sequence ::: rs2832040-rs11088088

FIG. 6U

GAGTTAAATAAAGCACTTGCTTCTATTGTTTGTACCTAAACTTAACAGAAcACAGTAAGT
AACAAGTCATTGGGATGCAGAAAAGAAAAAAGAGAGTGAAGGAAGGAGAaAAGGTGAAGG
GAGAATGGAAGAGAGGAAGGGAGGGAGGAA (SEQ ID NO: 134)

```
OLIGO            (SEQ ID NOs: 135, 136)
LEFT PRIMER         13    21   54.81   38.10   4.00   0.00
GCACTTGCTTCTATTGTTTGT
RIGHT PRIMER       141    20   57.37   50.00   2.00   0.00
CCCTTCCTCTCTTCCATTCT
SEQUENCE SIZE: 150
INCLUDED REGION SIZE: 150

PRODUCT SIZE: 129, PAIR ANY COMPL: 2.00, PAIR 3' COMPL: 0.00
```

```
   1 GAGTTAAATAAAGCACTTGCTTCTATTGTTTGTACCTAAACTTAACAGAAcACAGTAAGT
          >>>>>>>>>>>>>>>>>>>>>

61 AACAAGTCATTGGGATGCAGAAAAGAAAAAAGAGAGTGAAGGAAGGAGAaAAGGTGAAGG

121 GAGAATGGAAGAGAGGAAGGGAGGGAGGAA
     <<<<<<<<<<<<<<<<<<<<
```

46) Whole sequence ::: rs2832141-rs2246777 aaacgagccaccagtgggAGCACTGCAGGTATCTGTGTGAGACCcGTACTTCACAACTCC
TGCTTTCCCTCCATAAAGtAGCTTGCATTTTCCACATTGACTTTGCAGTTCTTTGGTATC
TGTATTGGT (SEQ ID NO: 137)

```
OLIGO            (SEQ ID NOs: 138, 139)
LEFT PRIMER         14    18   58.28   61.11   6.00   2.00
gtgggAGCACTGCAGGTA
RIGHT PRIMER       123    21   55.05   38.10   4.00   2.00
ACAGATACCAAAGAACTGCAA
SEQUENCE SIZE: 129
INCLUDED REGION SIZE: 129

PRODUCT SIZE: 110, PAIR ANY COMPL: 5.00, PAIR 3' COMPL: 3.00
```

```
   1 aaacgagccaccagtgggAGCACTGCAGGTATCTGTGTGAGACCcGTACTTCACAACTCC
                      >>>>>>>>>>>>>>>>>>

61 TGCTTTCCCTCCATAAAGtAGCTTGCATTTTCCACATTGACTTTGCAGTTCTTTGGTATC
                                                <<<<<<<<<<<<<<<<<<

121 TGTATTGGT
     <<<
```

47) Whole sequence ::: rs2832959 -rs9980934

TGGACACCTTTCAACTTAGAAATCATAAACAGATTCATTTcCTTAAAGTTAATGaaaaga
attaacagaccctcctcaaaaaagacatatatgcagcctacaatcatatgaaaaaagtt
caacattactgttcagcaaatcaaa (SEQ ID NO: 140)

OLIGO            (SEQ ID NOs: 141, 142)

FIG. 6V

```
LEFT PRIMER          1    20    53.30    40.00    3.00    3.00
TGGACACCTTTCAACTTAGA
RIGHT PRIMER       134    22    50.67    27.27    8.00    3.00
gaacagtaatgttgaactttt
SEQUENCE SIZE: 145
INCLUDED REGION SIZE: 145

PRODUCT SIZE: 134, PAIR ANY COMPL: 7.00, PAIR 3' COMPL: 3.00

1 TGGACACCTTTCAACTTAGAAATCATAAACAGATTCATTTcCTTAAAGTTAATGaaaaga
      >>>>>>>>>>>>>>>>>>>>

61 attaacagaccctcctcaaaaaagacatatatgcagcctacaatcatatgaaaaaaagtt
                                                          <<<<<<<<

121 caacattactgttcagcaaatcaaa
      <<<<<<<<<<<<<<
```

7th group

48) Whole sequence ::: rs2833734-rs2833735

TGGATACATTCCTAGAAATAGATGGAAACTGCTCTTGCAAAAAGCTTAGCACATGTTAAA
aATTTTAGAAACAATTTGCCAAAGTTTATTTAGTCTAGTGATTTtGACAGGTTAAATGGA
CCCTTTGAGATCTTTTTTCCTCAAGTACAAAGGCT (SEQ ID NO: 143)

```
OLIGO            (SEQ ID NOs: 144, 145)
LEFT PRIMER         33    21    58.90    38.10    6.00    2.00
TCTTGCAAAAAGCTTAGCACA
RIGHT PRIMER       137    21    57.77    38.10    6.00    1.00
AAAAAGATCTCAAAGGGTCCA
SEQUENCE SIZE: 155
INCLUDED REGION SIZE: 155

PRODUCT SIZE: 105, PAIR ANY COMPL: 4.00, PAIR 3' COMPL: 0.00

1 TGGATACATTCCTAGAAATAGATGGAAACTGCTCTTGCAAAAAGCTTAGCACATGTTAAA
                                       >>>>>>>>>>>>>>>>>>>>>

61 aATTTTAGAAACAATTTGCCAAAGTTTATTTAGTCTAGTGATTTtGACAGGTTAAATGGA
                                                              <<<<

121 CCCTTTGAGATCTTTTTTCCTCAAGTACAAAGGCT
      <<<<<<<<<<<<<<<<<
```

49) Whole sequence ::: rs933121-rs933122

GCTTTTGCTGAACATCAAGTGGTGAGCCAGGACTCAAaGCCAGATCTTCTTGTTTCCCTG
TTAGGTGTtTGTAGCACAACTGGTATCTGCAGACTATGCTGCTGGAAGGGCTAGCCGTC (SEQ ID NO: 146)

```
OLIGO            (SEQ ID NOs: 147, 148)
LEFT PRIMER          1    20    55.61    40.00    6.00    3.00
GCTTTTGCTGAACATCAAGT
RIGHT PRIMER       109    19    55.56    52.63    3.00    3.00
CCTTCCAGCAGCATAGTCT
SEQUENCE SIZE: 119
```

FIG. 6W

INCLUDED REGION SIZE: 119

PRODUCT SIZE: 109, PAIR ANY COMPL: 5.00, PAIR 3' COMPL: 1.00

```
  1 GCTTTTGCTGAACATCAAGTGGTGAGCCAGGACTCAAaGCCAGATCTTCTTGTTTCCCTG
    >>>>>>>>>>>>>>>>>>>>

61 TTAGGTGTtTGTAGCACAACTGGTATCTGCAGACTATGCTGCTGGAAGGGCTAGCCGTC
                              <<<<<<<<<<<<<<<<<<<
```

50) Whole sequence ::: rs2834140-rs12626953

ACTGTCCTAGAAAATCCAGGATGTGCAGTGATCAtGTATGAATGCATGGACCTGCACACA
CAGGAGTGAACAAAAGACCCACCCCTGCCAGGTCACCACTCATATCTCACCCCAGCCCAC
GCTAGCTCACaCTCCTCCCCACACACCACTGACCTCATCAT (SEQ ID NO: 149)

```
OLIGO           (SEQ ID NOs: 150, 151)
LEFT PRIMER         12    18    53.64    44.44    7.00    1.00
AAATCCAGGATGTGCAGT
RIGHT PRIMER       161    19    53.29    47.37    4.00    0.00
ATGATGAGGTCAGTGGTGT
SEQUENCE SIZE: 161
INCLUDED REGION SIZE: 161
```

PRODUCT SIZE: 150, PAIR ANY COMPL: 3.00, PAIR 3' COMPL: 0.00

```
  1 ACTGTCCTAGAAAATCCAGGATGTGCAGTGATCAtGTATGAATGCATGGACCTGCACACA
    >>>>>>>>>>>>>>>>>>>

61 CAGGAGTGAACAAAAGACCCACCCCTGCCAGGTCACCACTCATATCTCACCCCAGCCCAC

121 GCTAGCTCACaCTCCTCCCCACACACCACTGACCTCATCAT
                            <<<<<<<<<<<<<<<<<<<
```

51) Whole sequence ::: rs2834485-rs3453

CACATCACAGATCATAGTAAATGGCTTTAATTTTTTAaCGAAATCTCACTACTGCAAATG
CATTGTTGTCCTAGCTAATGAATGCAtAGAGTATTGCCTGCAAAATAATAATTGAGATTC
TATT (SEQ ID NO: 152)

```
OLIGO           (SEQ ID NOs: 153, 154)
LEFT PRIMER          3    22    52.35    36.36    4.00    0.00
CATCACAGATCATAGTAAATGG
RIGHT PRIMER       113    21    53.50    23.81    6.00    4.00
AATTATTATTTTGCAGGCAAT
SEQUENCE SIZE: 124
INCLUDED REGION SIZE: 124
```

PRODUCT SIZE: 111, PAIR ANY COMPL: 5.00, PAIR 3' COMPL: 2.00

```
  1 CACATCACAGATCATAGTAAATGGCTTTAATTTTTTAaCGAAATCTCACTACTGCAAATG
    >>>>>>>>>>>>>>>>>>>>>>

61 CATTGTTGTCCTAGCTAATGAATGCAtAGAGTATTGCCTGCAAAATAATAATTGAGATTC
                                             <<<<<<<<<<<<<<<<<<<<<
```

FIG. 6X

121 TATT

8th group

52) Whole sequence ::: rs9974986-rs2834703

TTATCCTCCACATCCTCATGAGGCAAACACCTTTCCTACCTTACCGCTCCcCAGTGGCCT
CCCTGTTGCCTTCTTATTCAAGACTAAGACtCTCTAGAATGTTCTTTATCCTGAGTCCAG
CTGATTGTCTATACTAATATCAGTACGGGGT (SEQ ID NO: 155)

```
OLIGO            (SEQ ID NOs: 156, 157)
LEFT PRIMER         17    20    60.50    50.00    4.00    2.00
CATGAGGCAAACACCTTTCC
RIGHT PRIMER       121    22    58.46    45.45    3.00    0.00
GCTGGACTCAGGATAAAGAACA
SEQUENCE SIZE: 151
INCLUDED REGION SIZE: 151
```

PRODUCT SIZE: 105, PAIR ANY COMPL: 4.00, PAIR 3' COMPL: 1.00

```
  1 TTATCCTCCACATCCTCATGAGGCAAACACCTTTCCTACCTTACCGCTCCcCAGTGGCCT
                     >>>>>>>>>>>>>>>>>>>>

61 CCCTGTTGCCTTCTTATTCAAGACTAAGACtCTCTAGAATGTTCTTTATCCTGAGTCCAG
                                    <<<<<<<<<<<<<<<<<<<<<<

121 CTGATTGTCTATACTAATATCAGTACGGGGT
    <
```

53) Whole sequence ::: rs12482353-rs2205032

ATCACCTGGTTTGGTGCATCCTCGCAGAAAGAGAGCCATACAGTGAAGTGGAAACACACCCAAAAGCTCT
GCAATATTCCTAGAAGTTCTCGAATCTCCTCCTTAAcAGAGCTGCAGAAGGGAAACACAGACAGGAAGCA
CCTGTTTGACTCAgACAGCAGCCCTAATGCAGTGCCACTCAGGAGCATTCCCTCATTTGAAGACCCCCCA
ATTACATGAAATTATCAACCCC (SEQ ID NO: 346)

```
OLIGO            (SEQ ID NOs: 347, 348)
LEFT PRIMER         56    20    59.74    45.00    4.00    2.00
ACACCCAAAAGCTCTGCAAT
RIGHT PRIMER       199    20    60.59    50.00    4.00    2.00
CAAATGAGGGAATGCTCCTG
SEQUENCE SIZE: 232
INCLUDED REGION SIZE: 232
```

PRODUCT SIZE: 144, PAIR ANY COMPL: 3.00, PAIR 3' COMPL: 0.00

```
  1 ATCACCTGGTTTGGTGCATCCTCGCAGAAAGAGAGCCATACAGTGAAGTGGAAACACACC
                                                           >>>>>

61 CAAAAGCTCTGCAATATTCCTAGAAGTTCTCGAATCTCCTCCTTAAcAGAGCTGCAGAAG
    >>>>>>>>>>>>>>>

121 GGAAACACAGACAGGAAGCACCTGTTTGACTCAgACAGCAGCCCTAATGCAGTGCCACTC
                                                              <

181 AGGAGCATTCCCTCATTTGAAGACCCCCCAATTACATGAAATTATCAACCCC
```

54) Whole sequence ::: rs2776266-rs2835001 agggtgcagcactttattatggaagcctgagctgactaatacaGGTGTCTcTATATCTCA
CTGAGGGAAAGTGACAGGAAAGTAAGAACCATTTaTGTCCAACACTCCAGAGGAGTCAAC
CAGATTCTGGGGGAAAAGAAGGTAC (SEQ ID NO: 158)

```
OLIGO            (SEQ ID NOs: 159, 160)
LEFT PRIMER          20    20    58.75    50.00    4.00    1.00
tggaagcctgagctgactaa
RIGHT PRIMER        142    20    59.87    50.00    4.00    3.00
CCTTCTTTTCCCCCAGAATC
SEQUENCE SIZE: 145
INCLUDED REGION SIZE: 145
```

PRODUCT SIZE: 123, PAIR ANY COMPL: 4.00, PAIR 3' COMPL: 0.00

```
    1 agggtgcagcactttattatggaagcctgagctgactaatacaGGTGTCTcTATATCTCA
                            >>>>>>>>>>>>>>>>>>>>

61 CTGAGGGAAAGTGACAGGAAAGTAAGAACCATTTaTGTCCAAGAGTCCAGAGGAGTCAAC

121 CAGATTCTGGGGGAAAAGAAGGTAC
         <<<<<<<<<<<<<<<<<<<<
```

55) Whole sequence ::: rs1984014-rs1984015

TGAGAAT TTAGGAGAACAGAAGATCAGAGGGCTGCACaGGCTAAACTAGACAATGAGCCC
ATGCAAGTAAGTTAAGAGGAGAAGCGGGTAAGTATGCACCTGCTTTGTCTAGGtGACCAG
CAAGCATTTAGCAATAGTCTTTT TCAAAACAACAG (SEQ ID NO: 161)

```
OLIGO            (SEQ ID NOs: 162, 163)
LEFT PRIMER           8    22    53.09    40.91    4.00    1.00
TTAGGAGAACAGAAGATCAGAG
RIGHT PRIMER        142    22    53.52    31.82    4.00    2.00
AAAGACTATTGCTAAATGCTTG
SEQUENCE SIZE: 154
INCLUDED REGION SIZE: 154
```

PRODUCT SIZE: 135, PAIR ANY COMPL: 4.00, PAIR 3' COMPL: 2.00

```
    1 TGAGAATTTAGGAGAACAGAAGATCAGAGGGCTGCACaGGCTAAACTAGACAATGAGCCC
             >>>>>>>>>>>>>>>>>>>>>>

61 ATGCAAGTAAGTTAAGAGGAGAAGCGGGTAAGTATGCACCTGCTTTGTCTAGGLGACCAG

121 CAAGCATTTAGCAATAGTCTTTTCAAAACAACAG
         <<<<<<<<<<<<<<<<<<<<<<
```

56) Whole sequence ::: rs1014593-rs9305569

GGAACTGCAGGAGATCCCTGCTGCCTTCCAGTTCATGGGATGATGGCCTCCACTTCTGCCCCTGTTTGCT
TCTCCTTTCAaATCTTACATGAAGGTATACAGTTTGAAGAAGCCAGTTTGACTCCAATATCTGTGCAATG
GAATACTGCTCATTAAAAAGgAATTAAACTATTGATACACACAACATGGGTGAAGATCAAACTGTCTCCT

FIG. 6Z

TCCCTTTGATTCAAGGGAATCTGAGAAATG (SEQ ID NO: 349)

```
OLIGO              (SEQ ID NOs: 350, 351)
LEFT PRIMER           51      19    59.86    52.63    2.00    0.00
ACTTCTGCCCCTGTTTGCT
RIGHT PRIMER         198      21    58.84    42.86    4.00    3.00
TGATCTTCACCCATGTTGTGT
```

*FIG. 6AA*

SEQUENCE SIZE: 239
INCLUDED REGION SIZE: 239

PRODUCT SIZE: 148, PAIR ANY COMPL: 2.00, PAIR 3' COMPL: 0.00

```
    1 GAACTGCAGGAGATCCCTGCTGCCTTCCAGTTCATGGGATGATGGCCTCCACTTCTGCCC
                                                     >>>>>>>>>>

61 CTGTTTGCTTCTCCTTTCAaATCTTACATGAAGGTATACAGTTTGAAGAAGCCAGTTTGA
      >>>>>>>>>

121 CTCCAATATCTGTGCAATGGAATACTGCTCATTAAAAAGgAATTAAACTATTGATACACA
                                                                <<<

181 CAACATGGGTGAAGATCAAACTGTCTCCTTCCCTTTGATTCAAGGGAATCTGAGAAATG
      <<<<<<<<<<<<<<<<<
```

57) Whole sequence ::: rs7281674-rs2835316

AAACAGGCAAAATAAGCGTAGGGCTGTGTGTCCAACAGTTaATCATAAAGCCATCACCAG
GAGACgTCACTGGGCGCCTTCTGGAGTCTATCCGTCCTAACTTTGC (SEQ ID NO: 164)

OLIGO          (SEQ ID NOs: 165, 166)
LEFT PRIMER         13    20    59.93    55.00    4.00    0.00
TAAGCGTAGGGCTGTGTCTG
RIGHT PRIMER        97    21    60.08    57.14    3.00    1.00
GGACGGATAGACTCCAGAAGG
SEQUENCE SIZE: 106
INCLUDED REGION SIZE: 106

PRODUCT SIZE: 85, PAIR ANY COMPL: 3.00, PAIR 3' COMPL: 0.00

```
    1 AAACAGGCAAAATAAGCGTAGGGCTGTGTGTGCAACAGTTaATCATAAAGCCATCACCAG
                   >>>>>>>>>>>>>>>>>>>>

61 GAGACgTCACTGGGCGCCTTCTGGAGTCTATCCGTCCTAACTTTGC
                         <<<<<<<<<<<<<<<<<<<<<
```

58) Whole sequence ::: rs13047304-rs13047322 gaatgaccttggcactttttatcaaacatcaactggccacaCacaggtgagtctacttctg
gacacttaTcctgttccattcatctgtatatctctatccttacac (SEQ ID NO: 167)

OLIGO          (SEQ ID NOs: 168, 169)
LEFT PRIMER          1    23    60.36    39.13    3.00    2.00
gaatgaccttggcactttttatca
RIGHT PRIMER       101    27    57.86    33.33    4.00    0.00
aaggatagagatatacagatgaatgga
SEQUENCE SIZE: 105
INCLUDED REGION SIZE: 105

PRODUCT SIZE: 101, PAIR ANY COMPL: 4.00, PAIR 3' COMPL: 1.00

```
    1 gaatgaccttggcactttttatcaaacatcaactggccacaCacaggtgagtctacttctg
      >>>>>>>>>>>>>>>>>>>>>>>
```

FIG. 6AB

```
 61 gacacttaTcctgttccattcatctgtatatctctatccttacac
    <<<<<<<<<<<<<<<<<<<<<<<<<
```

59) Whole sequence ::: rs2835545-rs4816551

CTGCTGGAATAGGCTGCTTGGCCATGTTCTTGGAAGCTACCACCATATCAaGGTAATTTC
CCACACAACATTCCAGCCCCTGCTTTCCtCTCTGGCCTTATCTAGGGCCATTCCCCAACT
CAGGTGAAT (SEQ ID NO: 170)

```
OLIGO            (SEQ ID NOs: 171, 172)
LEFT PRIMER         20    20    60.21    50.00   4.00   2.00
GGCCATGTTCTTGGAAGCTA
RIGHT PRIMER       128    20    60.89    50.00   5.00   0.00
TTCACCTGAGTTGGGGAATG
SEQUENCE SIZE: 129
INCLUDED REGION SIZE: 129
```

PRODUCT SIZE: 109, PAIR ANY COMPL: 3.00, PAIR 3' COMPL: 0.00

```
    1 CTGCTGGAATAGGCTGCTTGGCCATGTTCTTGGAAGCTACCACCATATCAaGGTAATTTC
                           >>>>>>>>>>>>>>>>>>>>

61 CCACACAACATTCCAGCCCCTGCTTTCCtCTCTGGCCTTATCTAGGGCCATTCCCCAACT
                                                       <<<<<<<<<<

121 CAGGTGAAT
      <<<<<<<<
```

60) Whole sequence ::: rs2835735-rs2835736

ACCTTTGTTCCATGCACCGCGCAAATACCTGGGAACCCTTaTTGCCCAACTCAAGAGCCA
GAGTCCTCTGTCATCATTTTGCCTCTCTCCTAAGTGAgAGGACTGAGTGCAGACTTGGTG
TTTGTGGGTGAGGCATGT (SEQ ID NO: 173)

```
OLIGO            (SEQ ID NOs: 174, 175)
LEFT PRIMER         11    18    62.22    55.56   5.00   0.00
CATGCACCGCGCAAATAC
RIGHT PRIMER       136    19    59.38    52.63   2.00   0.00
ATGCCTCACCCACAAACAC
SEQUENCE SIZE: 138
INCLUDED REGION SIZE: 138
```

PRODUCT SIZE: 126, PAIR ANY COMPL: 3.00, PAIR 3' COMPL: 0.00

```
    1 ACCTTTGTTCCATGCACCGCGCAAATACCTGGGAACCCTTaTTGCCCAACTCAAGAGCCA
                >>>>>>>>>>>>>>>>>>

61 GAGTCCTCTGTCATCATTTTGCCTCTCTCCTAAGTGAgAGGACTGAGTGCAGACTTGGTG
                                                                <<<

121 TTTGTGGGTGAGGCATGT
      <<<<<<<<<<<<<<<<<<
```

61) Whole sequence ::: rs13047608-rs2835826

CTCCTGAGTCCAAGCCCTTCTCACTCACCTCTTTCTTGAACTAATTTCTTcCTGTTTTTT
TCCAGTCCTCCCTTCTGTTCATGTCTCTCCTCTGCACACTTCCATTTTgTGGTTCAGAAA

FIG. 6AC

ATGTCACCGTCCCAG TCACACTTGCCTTATGGCTGTTGT (SEQ ID NO: 176)

```
OLIGO           (SEQ ID NOs: 177, 178)
LEFT PRIMER         9    20    60.39   55.00   4.00   0.00
TCCAAGCCCTTCTCACTCAC
RIGHT PRIMER      135    20    59.97   50.00   3.00   1.00
CTGGGACGGTGACATTTTCT
SEQUENCE SIZE: 159
INCLUDED REGION SIZE: 159

PRODUCT SIZE: 127, PAIR ANY COMPL: 4.00, PAIR 3' COMPL: 0.00

1 CTCCTGAGTCCAAGCCCTTCTCACTCACCTCTTTCTTGAACTAATTTCTTcCTGTTTTTT
                >>>>>>>>>>>>>>>>>>>>

61 TCCAGTCCTCCCTTCTGTTCATGTCTCTCCTCTGCACACTTCCATTTTgTGGTTCAGAAA
                                                             <<<<<

121 ATGTCACCGTCCCAGTCACACTTGCCTTATGGCTGTTGT
      <<<<<<<<<<<<<<<
```

62) Whole sequence ::: rs857998-rs17284497

TGGAGAAAGTTGTTGCAAACTGCCCAGAGACCCTGGGAGTCACTCCAGTTTTCTGAAACCCAGATATTTC
AGtGCCTCAGGAGAGACAAGTCCTGACCTTCTCTCCTCCAGCTCTCCCAGgAGATAGGCAAGCCCCTAAC
TCCCTAACTAAGCCCTTCAGACCTGAAATCCATTGAGTGGCTTCTTT (SEQ ID NO: 352)

```
OLIGO           (SEQ ID NOs: 353, 354)
LEFT PRIMER        15    18    59.35   61.11   4.00   0.00
GCAAACTGCCCAGAGACC
RIGHT PRIMER      147    20    60.57   55.00   2.00   2.00
TTAGGCAGTTAGGGGCTTGC
SEQUENCE SIZE: 189
INCLUDED REGION SIZE: 189

PRODUCT SIZE: 133, PAIR ANY COMPL: 5.00, PAIR 3' COMPL: 2.00

1 TGGAGAAAGTTGTTGCAAACTGCCCAGAGACCCTGGGAGTCACTCCAGTTTTCTGAAACC
                   >>>>>>>>>>>>>>>>>>

61 CAGATATTTCAGtGCCTCAGGAGAGACAAGTCCTGACCTTCTCTCCTCCAGCTCTCCCAG 121 gAGATAGGCAAGCCCCTAACTCCCTAACTAAGCCCTTCACACCTGAAATCCATTGAGTGG
          <<<<<<<<<<<<<<<<<<<<

181 CTTCTTTAC
```

9th group

63) Whole sequence ::: rs2836550-rs2212596

CCCAGGAAGAGTGGAAAGATTAACCTTTGTCAGCCAAACCaGTGACACTTGATTACTTGA
CAGAACTAATCCTTCTGTCCTGATGACAGAAcTTCAACTACACAGGTACATGCAAGCTAA
TATCTGTTGTAA (SEQ ID NO: 179)

FIG. 6AD

```
OLIGO              (SEQ ID NOs: 180, 181)
LEFT PRIMER         1    21    59.56    47.62    3.00    2.00
CCCAGGAAGAGTGGAAAGATT
RIGHT PRIMER      120    21    56.03    42.86    6.00    1.00
TTAGCTTGCATGTACCTGTGT
SEQUENCE SIZE: 132
INCLUDED REGION SIZE: 132

PRODUCT SIZE: 120, PAIR ANY COMPL: 5.00, PAIR 3' COMPL: 3.00

1 CCCAGGAAGAGTGGAAAGATTAACCTTTGTGAGCCAAACCaGTGACACTTGATTACTTGA
      >>>>>>>>>>>>>>>>>>>>>

61 CAGAACTAATCCTTCTGTCCTGATGACAGAAcTTCAACTACACAGGTACATGCAAGCTAA
                                              <<<<<<<<<<<<<<<<<<<<<

121 TATCTGTTGTAA
```

64) Whole sequence ::: rs2836660-rs2836661

```
GCCTGGCAAGCTAGATGGGGTGAATTTTCACCTGCCACAGcCGCAAGTCAAAGCCACCGG
CTTCTCTCTTCTCCCTCCCATTGCTCCTGACAGCCAGGGTTAATATTTTGCCTCATGTAA
ACAGGGAGGCAtCCACCCGAGAATCTCCCCTCAGCCCACATAAGC (SEQ ID NO: 182)

OLIGO              (SEQ ID NOs: 183, 184)
LEFT PRIMER         9    20    55.41    40.00    4.00    2.00
AGCTAGATGGGGTGAATTTT
RIGHT PRIMER      158    18    61.14    61.11    3.00    3.00
TGGGCTGAGGGGAGATTC
SEQUENCE SIZE: 165
INCLUDED REGION SIZE: 165

PRODUCT SIZE: 150, PAIR ANY COMPL: 4.00, PAIR 3' COMPL: 3.00

1 GCCTGGCAAGCTAGATGGGGTGAATTTTCACCTGCCACAGcCGCAAGTCAAAGCCACCGG
                >>>>>>>>>>>>>>>>>>>>

61 CTTCTCTCTTCTCCCTCCCATTGCTCCTGACAGCCAGGGTTAATATTTTGCCTCATGTAA

121 ACAGGGAGGCAtCCACCCGAGAATCTCCCCTCAGCCCACATAAGC
                                  <<<<<<<<<<<<<<<<<<
```

65) Whole sequence ::: rs465612-rs8131220

```
atcaagctaattaatgttatctatcacttcAcatagttcaaccttttttgtggtgagag
tactgaagatctactctcttagcaattttcaaatctaaaatacattattattaacacagt
cactgtgccGtacgttagctctgaggaccttattcatttt (SEQ ID NO: 185)

OLIGO              (SEQ ID NOs: 186, 187)
LEFT PRIMER         1    22    47.51    22.73    6.00    4.00
atcaagctaattaatgttatct
RIGHT PRIMER      158    20    50.92    40.00    5.00    5.00
aatgaataaggtcctcagag
SEQUENCE SIZE: 160
INCLUDED REGION SIZE: 160
```

FIG. 6AE

PRODUCT SIZE: 158, PAIR ANY COMPL: 5.00, PAIR 3' COMPL: 2.00

```
  1 atcaagctaattaatgttatctatcacttcAcatagttcaaccttttttgtggtgagag
    >>>>>>>>>>>>>>>>>>>>>

61 tactgaagatctactctcttagcaattttcaaatctaaaatacattattattaacacagt 121 cactgtgccGtacgttagctctgaggaccttattcatttt
                                    <<<<<<<<<<<<<<<<<<
```

66) Whole sequence ::: rs9980072-rs8130031

TTTAATCTGATCATTGCCCTATGAGGTAGGgAGTATTCTGATTCCCATTTTATAAATAAG
GAACCCGAGGCTTAGAGAGCATCaGTGACTTGTTCAAGGTCACCCACAGCTGTCAAGTGA
CAGA (SEQ ID NO: 188)

```
OLIGO              (SEQ ID NOs: 189, 190)
LEFT PRIMER            1    21    55.02    33.33    6.00    2.00
TTTAATCTGATCATTGCCCTA
RIGHT PRIMER         111    18    57.61    55.56    5.00    1.00
AGCTGTGGGTGACCTTGA
SEQUENCE SIZE: 124
INCLUDED REGION SIZE: 124
```

PRODUCT SIZE: 111, PAIR ANY COMPL: 3.00, PAIR 3' COMPL: 1.00

```
  1 TTTAATCTGATCATTGCCCTATGAGGTAGGgAGTATTCTGATTCCCATTTTATAAATAAG
    >>>>>>>>>>>>>>>>>>>>>

61 GAACCCGAGGCTTAGAGAGCATCaGTGACTTGTTCAAGGTCACCCACAGCTGTCAAGTGA
                                           <<<<<<<<<<<<<<<<<<

121 CAGA
```

10$^{th}$ group

67) Whole sequence ::: rs418359-rs2836926 tgtcccaccattgtgtattaggtttgtagagCgtagacaacttgccttttagtttgtag
gtttctgtatcaagagaagatgtgtgtGggcctaacctagattacaggatcctggacttc
aagtctga (SEQ ID NO: 191)

```
OLIGO              (SEQ ID NOs: 192, 193)
LEFT PRIMER            1    20    54.64    40.00    6.00    3.00
tgtcccaccattgtgtatta
RIGHT PRIMER         128    20    54.70    45.00    9.00    3.00
tcagacttgaagtccaggat
SEQUENCE SIZE: 128
INCLUDED REGION SIZE: 128
```

PRODUCT SIZE: 128, PAIR ANY COMPL: 3.00, PAIR 3' COMPL: 1.00

```
  1 tgtcccaccattgtgtattaggtttgtagagCgtagacaacttgccttttagtttgtag
    >>>>>>>>>>>>>>>>>>>>
```

FIG. 6AF

```
 61 gtttctgtatcaagagaagatgtgtgtCggcctaacctagattacaggatcctggacttc
                                                    <<<<<<<<<<

121 aagtctga
    <<<<<<<<
```

68) Whole sequence ::: rs11701943-rs4816634 tcatttgctaaggtcggatagctcctaattggcaaagtcaCgatgggatcccagggattc
tgaggatgaagcctgtgtttaataactAttatgccaAGTGAGCATTTTCAAATATATGAG
AGAAATTA (SEQ ID NO: 194)

```
OLIGO            (SEQ ID NOs: 195, 196)
LEFT PRIMER         2    19   53.86   42.11   4.00   2.00
catttgctaaggtcggata
RIGHT PRIMER      114    20   51.56   30.00   6.00   2.00
TATTTGAAAATGCTCACTtg
SEQUENCE SIZE: 128
INCLUDED REGION SIZE: 128
```

PRODUCT SIZE: 113, PAIR ANY COMPL: 6.00, PAIR 3' COMPL: 0.00

```
  1 tcatttgctaaggtcggatagctcctaattggcaaagtcaCgatgggatcccagggattc
    >>>>>>>>>>>>>>>>>>>

61 tgaggatgaagcctgtgtttaataactAttatgccaAGTGAGCATTTTCAAATATATGAG
                                        <<<<<<<<<<<<<<<<<<<<

121 AGAAATTA
```

69) Whole sequence ::: rs7278447-rs7278858

CATTGCTTCAGGGGTGTTAGTTTTGTGTTCaCAACTAGATTATAAACTCCTCTTGCATTC
CTGATGGCAGTGACTTGAAGGCAttLatLLgaagaataatagacatacagaaaggggcac
atgtcataaaggtacagctggacgactttcacaaagtg (SEQ ID NO: 197)

```
OLIGO            (SEQ ID NOs: 198, 199)
LEFT PRIMER         5    20   55.96   45.00   2.00   0.00
GCTTCAGGGGTGTTAGTTTT
RIGHT PRIMER      157    20   55.97   45.00   5.00   1.00
ctttgtgaaaagtcgtccag
SEQUENCE SIZE: 159
INCLUDED REGION SIZE: 159
```

PRODUCT SIZE: 153, PAIR ANY COMPL: 4.00, PAIR 3' COMPL: 0.00

```
  1 CATTGCTTCAGGGGTGTTAGTTTTGTGTTCaCAACTAGATTATAAACTCCTCTTGCATTC
       >>>>>>>>>>>>>>>>>>>>

61 CTGATGGCAGTGACTTGAAGGCAtttatttgaagaataatagacatacagaaaggggcac 121 atgtcataaaggtacagctggacgactttcacaaagtg
                                 <<<<<<<<<<<<<<<<<<<<
```

FIG. 6AG

70) Whole sequence ::: rs385787-rs367001

GAGAGGATGGTGCCATCATGGAAAGCATGGGGCAGTCATGGAGATGACGGaGTAGCTCAT
GGAGAAgATAATGCCATCATGGAAGGCATAGTGCAGTCATGGAGATGATGGTGCAGC (SEQ ID NO: 200)

```
OLIGO            (SEQ ID NOs: 201, 202)
LEFT PRIMER           13     18    58.34    50.00    7.00    3.00
CCATCATGGAAAGCATGG
RIGHT PRIMER         108     20    55.09    45.00    4.00    2.00
TCATCTCCATGACTGCACTA
SEQUENCE SIZE: 117
INCLUDED REGION SIZE: 117
```

PRODUCT SIZE: 96, PAIR ANY COMPL: 7.00, PAIR 3' COMPL: 3.00

```
   1 GAGAGGATGGTGCCATCATGGAAAGCATGGGGCAGTCATGGAGATGACGGaGTAGCTCAT
                    >>>>>>>>>>>>>>>>>>

61 GGAGAAgATAATGCCATCATGGAAGGCATAGTGCAGTCATGGAGATGATGGTGCAGC
                                       <<<<<<<<<<<<<<<<<<<<
```

71) Whole sequence ::: rs367001-rs386095

ATGGGGCAGTCATGGAGATGACGGAGTAGCTCATGGAGAAaATAATGCCATCATGGAAGG
CATAGTGCAGTCATGGAGATGATGGTGCAGCTCATGGAGAAGATGGTGCCATCATGGaAG
GCATGGTGCAATCATGGAGTAGACAGTGCAGCTGGGCCaagattctc (SEQ ID NO: 203)

```
OLIGO            (SEQ ID NOs: 204, 205)
LEFT PRIMER           15     20    54.39    50.00    4.00    3.00
GAGATGACGGAGTAGCTCAT
RIGHT PRIMER         156     18    55.17    61.11    6.00    2.00
CCCAGCTGCACTGTCTAC
SEQUENCE SIZE: 167
INCLUDED REGION SIZE: 167
```

PRODUCT SIZE: 142, PAIR ANY COMPL: 6.00, PAIR 3' COMPL: 2.00

```
   1 ATGGGGCAGTCATGGAGATGACGGAGTAGCTCATGGAGAAaATAATGCCATCATGGAAGG
                    >>>>>>>>>>>>>>>>>>>>

61 CATAGTGCAGTCATGGAGATGATGGTGCAGCTCATGGAGAAGATGGTGCCATCATGGgAAG

121 GCATGGTGCAATCATGGAGTAGACAGTGCAGCTGGGCCaagattctc
                                <<<<<<<<<<<<<<<<<<
```

72) Whole sequence ::: rs2837296-rs2837297

GATGTGCCTCTCTTGTTCCAATCACAGGACAGGGGTATAAcTAGGGGCACTGTCTATACT
GGCTGCACTCTGGCCAGTGCTGTCCCAgGTAGATTCATCAGGGTCTAGAGCTTCAGCTAA
CAGCATGA (SEQ ID NO: 206)

```
OLIGO            (SEQ ID NOs: 207, 208)
LEFT PRIMER           11     20    56.00    45.00    4.00    1.00
TCTTGTTCCAATCACAGGAC
```

FIG. 6AH

```
RIGHT PRIMER       126    20    54.59    45.00    6.00    3.00
ATGCTGTTAGCTGAAGCTCT
SEQUENCE SIZE: 128
INCLUDED REGION SIZE: 128

PRODUCT SIZE: 116, PAIR ANY COMPL: 4.00, PAIR 3' COMPL: 1.00

1 GATGTGCCTCTCTTGTTCCAATCACAGGACAGGGGTATAAcTAGGGGCACTGTCTATACT
      >>>>>>>>>>>>>>>>>>>>

61 GGCTGCACTCTGGCCAGTGCTGTCCCAgGTAGATTCATCAGGGTCTAGAGCTTCAGCTAA
                                                  <<<<<<<<<<<<

121 CAGCATGA
      <<<<<<
```

73) Whole sequence ::: rs4239808-rs2410205

```
AGGGCCATGGGATGATGCAGGTGGAGACTGGAGTGCTACAGCTGCAAGCAAATACATTTCTGTGCTGTCA
AGCCAcCCATTTGGTGGTACTACGTTAAAACAGCTCTAGGAAATTAAtACAGATGTTGCCTGTATTTTTG
TTTCTCATATTACTACTCATTGTTTTAATGATCACTGTTTTATT   (SEQ ID NO: 355)

OLIGO           (SEQ ID NOs: 356, 357)
LEFT PRIMER        19    20    57.45    55.00    4.00    2.00
AGGTGGAGACTGGAGTGCTA
RIGHT PRIMER      145    22    56.58    31.82    2.00    0.00
AGAAACAAAAATACAGGCAACA
SEQUENCE SIZE: 184
INCLUDED REGION SIZE: 184

PRODUCT SIZE: 127, PAIR ANY COMPL: 3.00, PAIR 3' COMPL: 1.00

1 AGGGCCATGGGATGATGCAGGTGGAGACTGGAGTGCTACAGCTGCAAGCAAATACATTTC
                             >>>>>>>>>>>>>>>>>>>>

61 TGTGCTGTGAAGCCAcCCATTTGGTGGTACTACGTTAAAACAGCTCTAGGAAATTAAtAC

121 AGATGTTGCCTGTATTTTTGTTTCTCATATTACTACTCATTGTTTTAATGATGACTGTTT
                          <<<<<<<<<<<<<<<<<<<<<<

181 TATT
```

74) Whole sequence ::: rs2837381-rs4816672

```
TTTTATTCATTAAGTTGAAAGCTCCTAAAGCAGAGGGACCaTATTTTTATGTCCCAACTC
TCCTTAAGgCCTTGCCTATGATAGCACATCTCTTCAATAGAATTGTCCT (SEQ ID NO: 209)

OLIGO           (SEQ ID NOs: 210, 211)
LEFT PRIMER        16    20    55.17    45.00    4.00    0.00
TGAAAGCTCCTAAAGCAGAG
RIGHT PRIMER       97    20    50.59    35.00    4.00    3.00
TTGAAGAGATGTGCTATCAT
SEQUENCE SIZE: 109
INCLUDED REGION SIZE: 109
```

FIG. 6AI

PRODUCT SIZE: 82, PAIR ANY COMPL: 5.00, PAIR 3' COMPL: 1.00

```
    1 TTTTATTCATTAAGTTGAAAGCTCCTAAAGCAGAGGGACCaTATTTTTATGTCCCAACTC
                         >>>>>>>>>>>>>>>>>>>>

61 TCCTTAAGgCCTTGCCTATGATAGCACATCTCTTCAATAGAATTGTCCT
                <<<<<<<<<<<<<<<<<<<<
```

11 th group

75) Whole sequence ::: rs13047873-rs2837697

AAAGACCAGCTTTTAGCTGAACATCAGGGCTGCCTTCAGAGTTTAATTACCGCCCTCCCC
ATGGGGCCAAATGAGCCATCGACTCCTCCCAAGGGGGTTCgGCTTGGTACTGATCTTTAA
GTAAGTaAACGCTAAACCAGCTCATCTTAAAGCGCCCACATCTGATTTCCTGCTCTGCTG
CAAGACAGTAGGTGACTGGTAATGACC (SEQ ID NO: 214)

```
OLIGO           (SEQ ID NOs: 215, 216)
LEFT PRIMER       26      20    59.08    50.00   5.00   2.00
AGGGCTGCCTTCAGAGTTTA
RIGHT PRIMER     155      20    59.62    50.00   5.00   2.00
GCGCTTTAAGATGAGCTGGT
SEQUENCE SIZE: 207
INCLUDED REGION SIZE: 207
```

PRODUCT SIZE: 130, PAIR ANY COMPL: 3.00, PAIR 3' COMPL: 1.00

```
    1 AAAGACCAGCTTTTAGCTGAACATCAGGGCTGCCTTCAGAGTTTAATTACCGCCCTCCCC
                        >>>>>>>>>>>>>>>>>>>>

61 ATGGGGCCAAATGAGCCATCGACTCCTCCCAAGGGGGTTCgGCTTGGTACTGATCTTTAA

121 GTAAGTaAACGCTAAACCAGCTCATCTTAAAGCGCCCACATCTGATTTCCTGCTCTGCTG
                        <<<<<<<<<<<<<<<<<<<<

181 CAAGACAGTAGGTGACTGGTAATGACC
```

76) Whole sequence ::: rs455999-rs9305700

ACTCTGCTCCCAGTGTGAACATGGGGAAAGTTGATTAAACTCTCTGACTTCAGATTCCTC
aTGTAAAATGTGGGGAAACAGCTCTGACTTAATGGTGTCACTGTGAGGAGTAAATGAGGT
AgCATATTTAAAGGATTTTGTATAGTCCTCGTGACAGTAACCAGCCAATAGATGATATAG
CTAGTAATAGCA (SEQ ID NO: 217)

```
OLIGO           (SEQ ID NOs: 218, 219)
LEFT PRIMER       16      20    57.84    40.00   4.00   2.00
TGAACATGGGGAAAGTTGAT
RIGHT PRIMER     154      22    56.81    40.91   4.00   0.00
TCACCAGCACTATACAAAATCC
SEQUENCE SIZE: 192
INCLUDED REGION SIZE: 192
```

PRODUCT SIZE: 139, PAIR ANY COMPL: 4.00, PAIR 3' COMPL: 2.00

```
    1 ACTCTGCTCCCAGTGTGAACATGGGGAAAGTTGATTAAACTCTCTGACTTCAGATTCCTC
```

FIG. 6AJ

```
              >>>>>>>>>>>>>>>>>>>
   61  aTGTAAAATGTGGGGAAACAGCTCTGACTTAATGGTGTCACTGTGAGGAGTAAATGAGGT

121  AgCATATTTAAAGGATTTTGTATAGTGCTGGTGACAGTAACCAGCCAATAGATGATATAG
              <<<<<<<<<<<<<<<<<<<

181  CTAGTAATAGCA
```

77) Whole sequence ::: rs9976207-rs455473 cttcactgaccacttccttaactgtccactccgaaacaccCcttcttcctgttcttccaa
tacaccaaactctttcttgcctctgtgtgcttgcccatgctgttccttctggcttcttcc
ttcACATTCAAGTCTTGACTTAGATGTCACTTGCCAAGGGAGACCTTGGA (SEQ ID NO: 220)

```
OLIGO           (SEQ ID NOs: 221, 222)
LEFT PRIMER       12     21    54.96    47.62   4.00   0.00
acttccttaactgtccactcc
RIGHT PRIMER     159     19    54.64    47.37   7.00   2.00
CCTTGGCAAGTGACATCTA
SEQUENCE SIZE: 170
INCLUDED REGION SIZE: 170
```

PRODUCT SIZE: 148, PAIR ANY COMPL: 5.00, PAIR 3' COMPL: 3.00

```
    1  cttcactgaccacttccttaactgtccactccgaaacaccCcttcttcctgttcttccaa
                  >>>>>>>>>>>>>>>>>>>>>

61  tacaccaaactctttcttgcctctgtgtgcttgcccatgctgttccttctggcttcttcc 121  ttcACATTCAAGTCTTGACTTAGATGTCACTTGCCAAGGGAGACCTTGGA
                       <<<<<<<<<<<<<<<<<<<
```

78) Whole sequence ::: rs2837807-rs2837808

AAACATCCCAATAGACAAAACTCCAAGAAGAGTCAAAACAAGAATAAAGTaCAGGTCATC
TTTTCTTTTGCACTCCTGACAGCACTTTGTACATGGTAATAATAATCTACCAATTAACTA
CATAAGCCACATGGTTTTATCATAGTGTGAAGCTTTGTATCCAGAAAGGAGAGAAGGCTCC (SEQ ID
NO: 223)

```
OLIGO           (SEQ ID NOs: 224, 225)
LEFT PRIMER       23     22    56.31    36.36   3.00   0.00
CCAAGAAGAGTCAAAACAAGAA
RIGHT PRIMER     172     21    56.19    42.86   4.00   2.00
TCTCCTTTCTGGATACAAAGC
SEQUENCE SIZE: 181
INCLUDED REGION SIZE: 181
```

PRODUCT SIZE: 150, PAIR ANY COMPL: 5.00, PAIR 3' COMPL: 1.00

```
    1  AAACATCCCAATAGACAAAACTCCAAGAAGAGTCAAAACAAGAATAAAGTaCAGGTCATC
                         >>>>>>>>>>>>>>>>>>>>>>
```

FIG. 6AK

```
 61 TTTTCTTTTGCACTCCTGACAGCACTTTGTACATGGTAATAATAATCTACCAATTAACTA

121 CATAAGCCACATGGTTTTATcATAGTGTGAAGCTTTGTATCCAGAAAGGAGAGAAGGCTC
                                          <<<<<<<<<<<<<<<<<<<<

181 C
```

79) Whole sequence ::: rs9974587-rs2776356

GGCAGAGGCATGGGGTGCATAGGGATATGGGGTGGGCCAGTTTGCTCCTCAGACCAGAAG
GGGTGCAGGAcTCCCCCCGATCAGGATCaTGGAGAAAGGTGTGTGGACAGAGGAAGGGAGGG
AGGGAGAAATGGCAGCTGCCCTGCAGTGG (SEQ ID NO: 226)

```
OLIGO              (SEQ ID NOs: 227, 228)
LEFT PRIMER        42      20     60.52     55.00    3.00    2.00
TTGCTCCTCAGACCAGAAGG
RIGHT PRIMER      118      20     59.68     60.00    4.00    2.00
CTCCCTTCCTCTGTCCACAC
SEQUENCE SIZE: 149
INCLUDED REGION SIZE: 149
```

PRODUCT SIZE: 77, PAIR ANY COMPL: 5.00, PAIR 3' COMPL: 1.00

```
  1 GGCAGAGGCATGGGGTGCATAGGGATATGGGGTGGGCCAGTTTGCTCCTCAGACCAGAAG
                                         >>>>>>>>>>>>>>>>>>>>

61 GGGTGCAGGAcTCCCCCCGATCAGGATCaTGGAGAAAGGTGTGGACAGAGGAAGGGAGGG
      >                              <<<<<<<<<<<<<<<<<<<<

121 AGGGAGAAATGGCAGCTGCCCTGCAGTGG
```

80) Whole sequence ::: rs2838089-rs2838090 cagggactaagtgtctctgacaatacattcagccactactAcagtatgaagccagccct
catccccaccttcagagacccctggtgcctcagattcctcggccattctggagctgctgt
gCCCGAGGCTTGTGTAGTTGGAGATCATTTTGGCAGTCAGTGCTG (SEQ ID NO: 229)

```
OLIGO              (SEQ ID NOs: 230, 231)
LEFT PRIMER        12      22     55.48     40.91    5.00    2.00
tgtctctgacaatacattcagc
RIGHT PRIMER      160      20     55.81     45.00    4.00    2.00
CTGACTGCCAAAATGATCTC
SEQUENCE SIZE: 165
INCLUDED REGION SIZE: 165
```

PRODUCT SIZE: 149, PAIR ANY COMPL: 5.00, PAIR 3' COMPL: 1.00

```
  1 cagggactaagtgtctctgacaatacattcagccactactAcagtatgaagccagccct
                >>>>>>>>>>>>>>>>>>>>>>

61 catccccaccttcagagacccctggtgcctcagattcctcggccattctggagctgctgt
```

FIG. 6AL

```
121 gCCCGAGGCTTGTGTAGTTGGAGATCATTTTGGCAGTCAGTGCTG
         <<<<<<<<<<<<<<<<<<<<
```

12th group

81) Whole sequence ::: rs453592-rs380152

CCTGTCTCCGTGCGTGAAAGCCGGCTCCAAAGTGCCTTCTGTCCTATCTGCCTTCcGCAC
CTGGCTTTCCTGAAAGAAAGAAAACGCGTGGCTTATCTTTTCACGGCACGCCACCTTCAC
TCTCaCTTTTTCTTTTCTAATAAATACCTCTGGATGGGTTAGTGGTAATCTCTCCTCAAAC (SEQ ID NO: 232)

```
OLIGO           (SEQ ID NOs: 233, 234)
LEFT PRIMER         24    20   60.00   55.00   4.00   1.00
GCTCCAAAGTCCCTTCTCTC
RIGHT PRIMER       165    20   58.87   55.00   3.00   2.00
CCACTAACCCATCCAGAGGT
SEQUENCE SIZE: 181
INCLUDED REGION SIZE: 181

PRODUCT SIZE: 142, PAIR ANY COMPL: 4.00, PAIR 3' COMPL: 1.00

1 CCTGTCTCCGTGCGTGAAAGCCGGCTCCAAAGTGCCTTCTGTCCTATCTGCCTTCcGCAC
                              >>>>>>>>>>>>>>>>>>>>

61 CTGGCTTTCCTGAAAGAAAGAAAACGCGTGGCTTATCTTTTCACGGCACGCCACCTTCAC

121 TCTCaCTTTTTCTTTTCTAATAAATACCTCTGGATGGGTTAGTGGTAATCTCTCCTCAAA
                         <<<<<<<<<<<<<<<<<<<<

181 C
```

82) Whole sequence ::: rs442723-rs449888

GGGAGCACAACCTAGGCCCCTCCTGGGGAGGTGGTGGAGTCAGAATCACGTAAGAGaCAA
AGTTCCAGTCCCTCAGTGCCGGCTCCATTGTCCCCTGGACTTCCCTTACAAACCACAGAT
GCAAAGAGAGCACTTCTCgGAATCTCCACACAGCCACGGTGGAGCACTCAACCCACGCGA
CCCTCGGGCGCAGGTGCT (SEQ ID NO: 235)

```
OLIGO           (SEQ ID NOs: 236, 237)
LEFT PRIMER         23    20   65.82   65.00   3.00   1.00
CTGGGGAGGTGGTGGAGTCA
RIGHT PRIMER       169    20   66.12   65.00   7.00   1.00
GAGTGCTCCACCGTGGCTGT
SEQUENCE SIZE: 198
INCLUDED REGION SIZE: 198

PRODUCT SIZE: 147, PAIR ANY COMPL: 7.00, PAIR 3' COMPL: 1.00

1 GGGAGCACAACCTAGGCCCCTCCTGGGGAGGTGGTGGAGTCAGAATCACGTAAGAGaCAA
                              >>>>>>>>>>>>>>>>>>>>

61 AGTTCCAGTCCCTCAGTGCCGGCTCCATTGTCCCCTGGACTTCCCTTACAAACCACAGAT
```

FIG. 6AM

```
121 GCAAAGAGAGCACTTCTCgGAATCTCCACACAGCCACGGTGGAGCACTCAACCCACGCGA
                                 <<<<<<<<<<<<<<<<<<

181 CCCTCGGGCGCAGGTGCT
```

83) Whole sequence ::: rs375886-rs9976560

CCTGAGAAGCTTCCAGCAAAGCACCAGCACGAACCGCCCCACCTCCCCACCTCCCCGCAA
GCGTTGcCGGGACTGACAGATTACAGAGCTCTGgTCCCTCTGCACTCCTGCTCTGCCACC
CCCAGGGTGTCAGAATGTGCCCCCCACACAGTTTCCAAAAG (SEQ ID NO: 238)

```
OLIGO            (SEQ ID NOs: 239, 240)
LEFT PRIMER          18     18    59.84   55.56   2.00   0.00
AAAGCACCAGCACGAACC
RIGHT PRIMER        143     18    59.89   61.11   3.00   3.00
GGGGCACATTCTGACACC
SEQUENCE SIZE: 161
INCLUDED REGION SIZE: 161
```

PRODUCT SIZE: 126, PAIR ANY COMPL: 3.00, PAIR 3' COMPL: 0.00

```
  1 CCTGAGAAGCTTCCAGCAAAGCACCAGCACGAACCGCCCCACCTCCCCACCTCCCCGCAA
                    >>>>>>>>>>>>>>>>>>

61 GCGTTGcCGGGACTGACAGATTACAGAGCTCTGgTCCCTCTGCACTCCTGCTCTGCCACC

121 CCCAGGGTGTCAGAATGTGCCCCCCACACAGTTTCCAAAAG
          <<<<<<<<<<<<<<<<<<
```

84) Whole sequence ::: rs3819900-rs3819901

ATGGAGCTGCTGCGCCGGCCTGAGCTCTGATCCCTCCTCCGACCCAGCCTCACCCTGCaA
GCAGCACCATGTGGGGCTCAGAATGGGGATCTTAAGGGACCCTcCCCACAACCTCCCGAT
AAGCCTTTCCACGGAGGGCCCAAGCGGAGACAGGAGAACACT (SEQ ID NO: 241)

```
OLIGO            (SEQ ID NOs: 242, 243)
LEFT PRIMER          20     19    57.00   57.89   6.00   0.00
CTGAGCTCTGATCCCTCCT
RIGHT PRIMER        158     18    57.51   55.56   2.00   0.00
TTCTCCTGTCTCCGCTTG
SEQUENCE SIZE: 162
INCLUDED REGION SIZE: 162
```

PRODUCT SIZE: 139, PAIR ANY COMPL: 3.00, PAIR 3' COMPL: 0.00

```
  1 ATGGAGCTGCTGCGCCGGCCTGAGCTCTGATCCCTCCTCCGACCCAGCCTCACCCTGCaA
                       >>>>>>>>>>>>>>>>>>>

61 GCAGCACCATGTGGGGCTCAGAATGGGGATCTTAAGGGACCCTcCCCACAACCTCCCGAT

121 AAGCCTTTCCACGGAGGGCCCAAGCGGAGACAGGAGAACACT
                  <<<<<<<<<<<<<<<<<<
```

85) Whole sequence ::: rs10451852-rs10451853

FIG. 6AN

ACTTTCAGAATGTGCTGCCTTCCACGTGTGAACCAGACTGAGCTCCTTTCTGCCACTGAT
GTTGAATTGTCCATTTGCTCACaTCAGTGTCCACGTGGCAAATCCACAGGGCgTGGGTGG
GATCCTGCAGTCTAGACAAAGCCAAGGAGCACCGCTGGAGGCCACGTTGGGCTTCCCAAT
CCACATGCAAACCC (SEQ ID NO: 244)

```
OLIGO           (SEQ ID NOs: 245, 246)
LEFT PRIMER           45    20    59.29    50.00    3.00    1.00
CCTTTCTGCCACTGATGTTG
RIGHT PRIMER         190    19    60.46    47.37    4.00    0.00
TTGCATGTGGATTGGGAAG
SEQUENCE SIZE: 194
INCLUDED REGION SIZE: 194

PRODUCT SIZE: 146, PAIR ANY COMPL: 4.00, PAIR 3' COMPL: 0.00

1 ACTTTCAGAATGTGCTGCCTTCCACGTGTGAACCAGACTGAGCTCCTTTCTGCCACTGAT
                                                  >>>>>>>>>>>>>>>>

61 GTTGAATTGTCCATTTGCTCACaTCAGTGTCCACGTGGCAAATCCACAGGGCgTGGGTGG
      >>>>

121 GATCCTGCAGTCTAGACAAAGCCAAGGAGCACCGCTGGAGGCCACGTTGGGCTTCCCAAT
                                                          <<<<<<<<<

181 CCACATGCAAACCC
      <<<<<<<<<<
```

86) Whole sequence ::: rs7278528-rs11701158

TCTCCAGCCAGCGTGTCACAAAGCCGCTCACCTGCTCGTGTGAGTGTCTGAATGCACGTG
TTTGAGTGTCAGaGGCGTGTGAACCACAGCAACTCAATCTTGAATAGGGGCTGGGTAAAG
TGAGGCTgAGACCTCCCGGGGCTGCATTCCCAGATGGTTAAGGCATTCTAAGTCACAAGA
TGAGATAGGAAGTTCGCACAAGACACTGGTCAT (SEQ ID NO: 247)

```
OLIGO           (SEQ ID NOs: 248, 249)
LEFT PRIMER           28    20    60.53    55.00    4.00    0.00
TCACCTGCTCGTGTGAGTGT
RIGHT PRIMER         163    20    59.39    50.00    4.00    2.00
CCTTAACCATCTGGGAATGC
SEQUENCE SIZE: 213
INCLUDED REGION SIZE: 213

PRODUCT SIZE: 136, PAIR ANY COMPL: 3.00, PAIR 3' COMPL: 0.00

1 TCTCCAGCCAGCGTGTCACAAAGCCGCTCACCTGCTCGTGTGAGTGTCTGAATGCACGTG
                                 >>>>>>>>>>>>>>>>>>>>

61 TTTGAGTGTCAGaGGCGTGTGAACCACAGCAACTCAATCTTGAATAGGGGCTGGGTAAAG

121 TGAGGCTgAGACCTCCCGGGGCTGCATTCCCAGATGGTTAAGGCATTCTAAGTCACAAGA
                              <<<<<<<<<<<<<<<<<<<<

181 TGAGATAGGAAGTTCGCACAAGACACTGGTCAT
```

FIG. 6AO

87) Whole sequence ::: rs2839627-rs170916

TTGAGTCCTCTTAAGTAGTTACTATAGTGGAGAACTTGAGTCATTCTTTGTAGCGTGCTT
cGTAGAGCAGCGTGTTTGTTAGAAGGATTTGTTAATCCTGTATAGgGTCTTTACGAAGGC
TGTTTTCATGGAAGCTTCTCTTTGTTGACTCC (SEQ ID NO: 250)

```
OLIGO              (SEQ ID NOs: 251, 252)
LEFT PRIMER           28      22    55.68   36.36   5.00   1.00
TGGAGAACTTGAGTCATTCTTT
RIGHT PRIMER         152      19    52.33   47.37   3.00   2.00
GGAGTCAACAAAGAGAAGC
SEQUENCE SIZE: 152
INCLUDED REGION SIZE: 152

PRODUCT SIZE: 125, PAIR ANY COMPL: 5.00, PAIR 3' COMPL: 3.00

1 TTGAGTCCTCTTAAGTAGTTACTATAGTGGAGAACTTGAGTCATTCTTTGTAGCGTGCTT
                                 >>>>>>>>>>>>>>>>>>>>>>

61 cGTAGAGCAGCGTGTTTGTTAGAAGGATTTGTTAATCCTGTATAGgGTCTTTACGAAGGC

121 TGTTTTCATGGAAGCTTCTCTTTGTTGACTCC
                    <<<<<<<<<<<<<<<<<<<
```

88) Whole sequence ::: rs2839628-rs234740

CATTCTCTCCAGCTGCAAACTTTCTTCAACTTTCCTAAATTCTTAcTAAATTCAGAGGAA
TAGGATAAAGATCACTTAGAGAAAGGGTGCTTATGGACATAGCCTGAGTTTCCTTTAACC
TCTCTgCAATGGGTGCTTTTAACTAGCTTCTACATGGCAAGCTGTTTCAGTTTG (SEQ ID NO: 253)

```
OLIGO              (SEQ ID NOs: 254, 255)
LEFT PRIMER           20      21    50.06   28.57   3.00   2.00
CTTTCTTCAACTTTCCTAAAT
RIGHT PRIMER         160      19    50.96   42.11   4.00   2.00
TTGCCATGTAGAAGCTAGT
SEQUENCE SIZE: 174
INCLUDED REGION SIZE: 174

PRODUCT SIZE: 141, PAIR ANY COMPL: 5.00, PAIR 3' COMPL: 2.00

1 CATTCTCTCCAGCTGCAAACTTTCTTCAACTTTCCTAAATTCTTAcTAAATTCAGAGGAA
                         >>>>>>>>>>>>>>>>>>>>>

61 TAGGATAAAGATCACTTAGAGAAAGGGTGCTTATGGACATAGCCTGAGTTTCCTTTAACC

121 TCTCTgCAATGGGTGCTTTTAACTAGCTTCTACATGGCAAGCTGTTTCAGTTTG
                            <<<<<<<<<<<<<<<<<<<
```

89) Whole sequence ::: rs2838239-rs2838240

GGACATCTGGAACTGCACCAGCACAGAACCGACACGTTGTTAcTCATCGTCACTCGGCAG
GGCTGAAGACCACCAGAACTCATGACAGGCAGACGTGCCTGGCCCAGTTGAGGATGTAGC

FIG. 6AP tTCAGAGCCAAGCGCCAGTCCTGTTGGCCACGTGGGCTGGGGGCAGGATAGACCA (SEQ ID NO: 256)

```
OLIGO            (SEQ ID NOs: 257, 258)
LEFT PRIMER        17    19   59.73   57.89   2.00   0.00
ACCAGCACAGAACCGACAC
RIGHT PRIMER      145    18   62.40   61.11   4.00   0.00
AACAGGACTGGCGCTTGG
SEQUENCE SIZE: 175
INCLUDED REGION SIZE: 175

PRODUCT SIZE: 129, PAIR ANY COMPL: 4.00, PAIR 3' COMPL: 1.00

1 GGACATCTGGAACTGCACCAGCACAGAACCGACACGTTGTTAcTCATCGTCACTCGGCAG
                       >>>>>>>>>>>>>>>>>>>

61 GGCTGAAGACCACCAGAACTCATGACAGGCAGACGTGCCTGGCCCAGTTGAGGATGTAGC 121 tTCAGAGCCAAGCGCCAGTCCTGTTGGCCACGTGGGCTGGGGGCAGGATAGACCA
                <<<<<<<<<<<<<<<<<<
```

90) Whole sequence ::: rs630397-rs11089106

GGCTGGTTCTGCCCCTTGGGAGGTGGTTCCTTTGGCTGGACCAGAATGTCTGaAGATGATC
AGGAGAGGGCCAAGGGTTGGGGGGTGCCCCATGTGCACCCTGAGAATTGCACCAGGCACA
GtGAGCAACTTCAGCCCTCCTTGTGCAGAGCTGCAGCGTACAGTGCCAGCCCTCGCTGGC
CC (SEQ ID NO: 259)

```
OLIGO            (SEQ ID NOs: 260, 261)
LEFT PRIMER        14    20   61.79   55.00   3.00   0.00
CTTGGGAGGTGGTTCCTTTG
RIGHT PRIMER      148    18   61.15   61.11   4.00   1.00
CTGCACAAGGAGGGCTGA
SEQUENCE SIZE: 182
INCLUDED REGION SIZE: 182

PRODUCT SIZE: 135, PAIR ANY COMPL: 5.00, PAIR 3' COMPL: 0.00

1 GGCTGGTTCTGCCCCTTGGGAGGTGGTTCCTTTGGCTGGACCAGAATGTCTGaAGATGATC
                    >>>>>>>>>>>>>>>>>>>>

61 AGGAGAGGGCCAAGGGTTGGGGGGTGCCCCATGTGCACCCTGAGAATTGCACCAGCCACA

121 GtGAGCAACTTCAGCCCTCCTTGTGCAGAGCTGCAGCGTACAGTGCCAGCCCTCGCTGGC
                  <<<<<<<<<<<<<<<<<<

181 CC
```

91) Whole sequence ::: rs9637180-rs481767

GTTCTCACTTTACTGAGAAACCTGGCAGCTTCTCAGGCCACCGCCCAGGTCACCTGCTCA
CCAGCAAcGTGAACCACAGGAACtGAGGCTGTGCGGGAGGCGGCTCTGCTCTGTGCTGGG
CCCCCCTCCTCCTCACTCACCCTCTTCAGTCAAAG (SEQ ID NO: 262)

FIG. 6AQ

```
OLIGO           (SEQ ID NOs: 263, 264)
LEFT PRIMER         11   20   57.70   50.00   5.00   5.00
TACTGAGAAACCTGGCAGCT
RIGHT PRIMER       155   20   54.98   50.00   3.00   0.00
CTTTGACTGAAGAGGGTGAG
SEQUENCE SIZE: 155
INCLUDED REGION SIZE: 155

PRODUCT SIZE: 145, PAIR ANY COMPL: 3.00, PAIR 3' COMPL: 2.00

1 GTTCTCACTTTACTGAGAAACCTGGCAGCTTCTCAGGCCACCGCCCAGGTCACCTGCTCA
                 >>>>>>>>>>>>>>>>>>>>

61 CCAGCAAcGTGAACCACAGGAACtGAGGCTGTGCGGGAGGCGGCTCTGCTCTGTGCTGGG

121 CCCCCCTCCTCCTCACTCACCCTCTTCAGTCAAAG
              <<<<<<<<<<<<<<<<<<<<

92) Whole sequence ::: rs162360-rs162359

TTAGTATTATTATTTTCATATATATTTTTTATAATAATCATATATTCAATTTTATCATCA
AGAAAAAAGTTTTAAAATTCaAAATCCTTTCATGTGCACTGTTTTAAACTtAGGTAGAAG
AAAAAAAGTCACTGAAAATCCAAGATGTAATAAACAGGCCCAACAAAGGCCAACAAACTT (SEQ ID
NO: 265)

OLIGO           (SEQ ID NOs: 266, 267)
LEFT PRIMER         45   20   48.37   20.00   5.00   3.00
TTCAATTTTATCATCAAGAA
RIGHT PRIMER       163   20   55.18   40.00   4.00   1.00
TTGGGCCTGTTTATTACATC
SEQUENCE SIZE: 180
INCLUDED REGION SIZE: 180

PRODUCT SIZE: 119, PAIR ANY COMPL: 4.00, PAIR 3' COMPL: 1.00

1 TTAGTATTATTATTTTCATATATATTTTTTATAATAATCATATATTCAATTTTATCATCA
                                                   >>>>>>>>>>>>>>>>>>>>

61 AGAAAAAAGTTTTAAAATTCaAAATCCTTTCATGTGCACTGTTTTAAACTtAGGTAGAAG
      >>>>

121 AAAAAAAGTCACTGAAAATCCAAGATGTAATAAACAGGCCCAACAAAGGCCAACAAACTT
                        <<<<<<<<<<<<<<<<<<<<

93) Whole sequence ::: rs162356-rs162355

AGGGAACATGGCCTTGCCCACACAGATTTCAGACATCTGGCTCCAGAACTGTGGGAGGAC
ACATTTCTGTTGTTTAGAACTGCaTGTTTTTTATACTTTGTTATGGCTGCCCTAGGcAAC
TAATACAGATATTATTTTCCACTTCTGAACTTAGCAAAATATTTTTAAAATGAAATTCT
TAAATGTTGGCACAGT (SEQ ID NO: 268)

OLIGO           (SEQ ID NOs: 269, 270)
LEFT PRIMER         14   20   60.24   45.00   3.00   3.00
TTGCCCACACAGATTTCAGA
RIGHT PRIMER       156   22   56.88   36.36   5.00   0.00
TGCTAAGTTCAGAAGTGGAAAA
```

FIG. 6AR

```
SEQUENCE SIZE: 196
INCLUDED REGION SIZE: 196

PRODUCT SIZE: 143, PAIR ANY COMPL: 4.00, PAIR 3' COMPL: 2.00

1 AGGGAACATGGCCTTGCCCACACAGATTTCAGACATCTGGCTCCAGAACTGTGGGAGGAC
      >>>>>>>>>>>>>>>>>>>>

61 ACATTTCTGTTGTTTAGAACTGCaTGTTTTTTATACTTTGTTATGGCTGCCCTAGGcAAC

121 TAATACAGATATTATTTTCCACTTCTGAACTTAGCAAAATATTTTTAAAATGAAAATTCT
                        <<<<<<<<<<<<<<<<<<<<

181 TAAATGTTCGCACAGT

94) Whole sequence ::: rs91424-rs463738

CTGGATAAAGGATGCTACACGTCCCTGGTGGGACAGAGCAGGACGGCAGGGGATTTCATT
AcGCCAcTCAGAATGGCAGGCAATTGAAAAAACTTATAAATTGTTTATTTCCAGAATTTT (SEQ ID
NO: 271)

OLIGO           (SEQ ID NOs: 272, 273)
LEFT PRIMER        3    20   54.33   45.00   4.00   4.00
GGATAAAGGATGCTACACGT
RIGHT PRIMER     120    20   49.40   20.00   4.00   0.00
AAAATTCTGGAAATAAACAA
SEQUENCE SIZE: 120
INCLUDED REGION SIZE: 120

PRODUCT SIZE: 118, PAIR ANY COMPL: 3.00, PAIR 3' COMPL: 1.00

1 CTGGATAAAGGATGCTACACGTCCCTGGTGGGACAGAGCAGGACGGCAGGGGATTTCATT
      >>>>>>>>>>>>>>>>>>>>

61 AcGCCAcTCAGAATGGCAGGCAATTGAAAAAACTTATAAATTGTTTATTTCCAGAATTTT
                                           <<<<<<<<<<<<<<<<<<<<

95) Whole sequence ::: rs2838318-rs2838319

TGTCAGTGGTGTAATCCGACTGTGAAAGATCAGTCTAACAAAACAGCGGGGAGAGAGAGG
GCTGAATCAGAGCaACTAGGTCCAAAGCCGAGGGAACCACCAACAGATCCCCTGGTGACC
CAACAAGAAATGCTCACAGTCTGGACCCAgTCAGAGTCTGCAGGACACAGCAGACATTCT
GGAAGTTACAACAGCCAGGAGCAAGAGGACGCATGGCCTGACTG (SEQ ID NO: 274)

OLIGO           (SEQ ID NOs: 275, 276)
LEFT PRIMER       49    20   60.30   60.00   3.00   3.00
GGGAGAGAGAGGGCTGAATC
RIGHT PRIMER     202    21   59.00   52.38   4.00   2.00
GCTCCTGGCTGTTGTAACTTC
SEQUENCE SIZE: 224
INCLUDED REGION SIZE: 224

PRODUCT SIZE: 154, PAIR ANY COMPL: 4.00, PAIR 3' COMPL: 1.00

1 TGTCAGTGGTGTAATCCGACTGTGAAAGATCAGTCTAACAAAACAGCGGGGAGAGAGAGG
```

```
 61 GCTGAATCAGAGCaACTAGGTCCAAAGCCGAGGGAACCACCAACAGATCCCCTGGTGACC
    >>>>>>>>

121 CAACAAGAAATGCTCACAGTCTGGACCCAgTCAGAGTCTGCAGGACACAGCAGACATTCT

181 GGAAGTTACAACACCCACGAGCAAGAGGACGCATGGCCTGACTG
    <<<<<<<<<<<<<<<<<<<<
```

96) Whole sequence ::: rs915770-rs731935

CGCCAGAGCACCCCTTCTCAGAACAGAAAGCGTCTCTACAaAGTGATCCGGAAGTGAGTG
TGTGAGGGCGCTGCGTCCTCCCTGCTCCCCTTGGAGTTGCCCTTTCTTGCTCAGATCTGG
GTGCCTTgGCCTTGTCCTGGGCCCTTCCGCAGCCCCGGGGTGATCCCCGCTAG (SEQ ID NO: 277)

```
OLIGO           (SEQ ID NOs: 278, 279)
LEFT PRIMER         3    19   60.95   63.16   3.00   3.00
CCAGAGCACCCCTTCTCAG
RIGHT PRIMER      148    18   62.95   66.67   6.00   0.00
GGAAGGGCCCAGGACAAG
SEQUENCE SIZE: 174
INCLUDED REGION SIZE: 174
```

PRODUCT SIZE: 146, PAIR ANY COMPL: 6.00, PAIR 3' COMPL: 2.00

```
  1 CGCCAGAGCACCCCTTCTCAGAACAGAAAGCGTCTCTACAaAGTGATCCGGAAGTGAGTG
    >>>>>>>>>>>>>>>>>>>

61 TGTGAGGGCGCTGCGTCCTCCCTGCTCCCCTTGGAGTTGCCCTTTCTTGCTCAGATCTGG

121 GTGCCTTgGCCTTGTCCTGGGCCCTTCCGCAGCCCCGGGGTGATCCCCGCTAG
              <<<<<<<<<<<<<<<<<<
```

Final Set

97) Whole sequence ::: rs1573338-rs1573339

TATCTTACGGATTTGTCAACATCATTTGAGAAGAAGTCCATAGGCTCAGCAGATTTTTAT
GCCAGGTGGGCCATGGCATAAAAATGTGAAGAATGTGCTCaCTTAGACAATACcTGTGCT
AAAATTGGAACAATACAGAGAAGATTAGCAAATTAAAACAATGTTAGGAAGTCAGTGTGG
TGAGGTACGGTGCCTCATGCC (SEQ ID NO: 280)

```
OLIGO           (SEQ ID NOs: 281, 282)
LEFT PRIMER        47    21   59.24   42.86   3.00   1.00
CAGCAGATTTTTATGCCAGGT
RIGHT PRIMER      192    20   60.06   60.00   4.00   3.00
CACCGTACCTCACCACACTG
SEQUENCE SIZE: 201
INCLUDED REGION SIZE: 201
```

PRODUCT SIZE: 146, PAIR ANY COMPL: 4.00, PAIR 3' COMPL: 3.00

```
  1 TATCTTACGGATTTGTCAACATCATTTGAGAAGAAGTCCATAGGCTCAGCAGATTTTTAT
```

FIG. 6AT

```
                                           >>>>>>>>>>>>>
 61 GCCAGGTGGGCCATGGCATAAAAATGTGAAGAATGTGCTCaCTTAGACAATACcTGTGCT
    >>>>>>>

121 AAAATTGGAACAATACAGAGAAGATTAGCAAATTAAAACAATGTTAGGAAGTCAGTGTGG
                                                    <<<<<<<<

181 TCACCTACGGTGCCTCATGCC
    <<<<<<<<<<<
```

98) Whole sequence ::: rs3788094-rs3788095

AGGCAGGGCCCTCCTTGCCACATGTAAAGCTGCACAGAGCGGTCACTATATGTGTTTCCA
TATTTGCAATCCAACCACCACCAACTGAGTGTGCGTCCTGaTCAGCCGAGCCTGCCCACG
GTGGCCACAGGCCCTCTACATTCTAATCTCGAGAGCCTGAGCATGTACAAATTAAACgAA
GCAAAACGACACCACCCAGTTCTGGCCGTACTATAGGAGGTTTCCAGGAAGGGTTTGTGA
ACATAAACATAAGCTAGGTAACACTCCTTTCTGAA (SEQ ID NO: 283)

OLIGO           (SEQ ID NOs: 284, 285)
LEFT PRIMER            73    20    57.88    50.00    5.00    3.00
AACCACCACCAACTGAGTGT
RIGHT PRIMER          220    20    56.94    55.00    6.00    2.00
CCTCCTATAGTACGGCCAGA
SEQUENCE SIZE: 275
INCLUDED REGION SIZE: 275

PRODUCT SIZE: 148, PAIR ANY COMPL: 3.00, PAIR 3' COMPL: 1.00

```
  1 AGGCAGGGCCCTCCTTGCCACATGTAAAGCTGCACAGAGCGGTCACTATATGTGTTTCCA

61 TATTTGCAATCCAACCACCACCAACTGAGTGTGCGTCCTGaTCAGCCGAGCCTGCCCACG
                   >>>>>>>>>>>>>>>>>>>>

121 GTGGCCACAGGCCCTCTACATTCTAATCTCGAGAGCCTGAGCATGTACAAATTAAACgAA

181 GCAAAACGACACCACCCAGTTCTGGCCGTACTATAGGAGGTTTCCAGGAAGGGTTTGTGA
                            <<<<<<<<<<<<<<<<<<<<

241 ACATAAACATAAGCTAGGTAACACTCCTTTCTGAA
```

99) Whole sequence ::: rs756554-rs756555

TCAGAGCATCGCCTCAGTGGCCATCAATAGCTCGGGGGACTGGATTGCTTTTGGCTGTTC
AGGTTTGTCCCCaGCCTGGGTGGTAGAGATGGACTCCCCATTAGGGACCAGTGCTGCCCG
GCTACAGGCtTACTTGACAGCCACCCACTGGGGGTGCCCTCCCCTCCCCAGTTGTCTTC
CATGGGGTGCCCTCTCCCCCAGCCGCCTTTCAGAAGGGGCCCTCCCCTCC (SEQ ID NO: 286)

OLIGO           (SEQ ID NOs: 287, 288)
LEFT PRIMER            41    20    61.15    45.00    2.00    0.00
TGGATTGCTTTTGGCTGTTC
RIGHT PRIMER          189    20    61.37    55.00    6.00    2.00
CACCCCATGGAAGACAACTG

FIG. 6AU

SEQUENCE SIZE: 230
INCLUDED REGION SIZE: 230

PRODUCT SIZE: 149, PAIR ANY COMPL: 4.00, PAIR 3' COMPL: 2.00

```
    1 TCAGAGCATCGCCTCAGTGGCCATCAATAGCTCGGGGGACTGGATTGCTTTTGGCTGTTC
                                 >>>>>>>>>>>>>>>>>>>>

61 AGGTTTGTCCCCaGCCTGGGTGGTAGAGATGGACTCCCCATTAGGGACCAGTGCTGCCCG

121 GCTACAGGCtTACTTGACAGCCACCCACTGGGGGTGCCCTCCCCTCCCCCAGTTGTCTTC
                                                      <<<<<<<<<<

181 CATGGGGTGCCCTCTCCCCCAGCCGCCTTTCAGAAGGGGCCCTCCCCTCC
         <<<<<<<<
```

100 )Whole sequence ::: rs4350841-rs2838545

CTCATGCTTACATCCTTAGCTGATCATTAAACTTTGTGACCATTTCATGCTCACTGCTTT
CTTGCCcGGGAGCTAATGGTGAGGAAAGGTCACTGGGAACCAGCGCACCAACCTCAGACA
TcGATTTTGTTCCAGCCTTTTTTCCTGGGCAGGGGTGGCTATCACCTGCTGGTAGGCAGC
GGCAGGCCCACTGTCCTGC (SEQ ID NO: 289)

OLIGO           (SEQ ID NOs: 290, 291)
LEFT PRIMER          27     21    53.45    28.57    5.00    2.00
TTAAACTTTGTGACCATTTCA
RIGHT PRIMER        174     18    54.55    55.56    6.00    2.00
TACCAGCAGGTGATAGCC
SEQUENCE SIZE: 199
INCLUDED REGION SIZE: 199

PRODUCT SIZE: 148, PAIR ANY COMPL: 3.00, PAIR 3' COMPL: 0.00

```
    1 CTCATGCTTACATCCTTAGCTGATCATTAAACTTTGTGACCATTTCATGCTCACTGCTTT
                                 >>>>>>>>>>>>>>>>>>>>>

61 CTTGCCcGGGAGCTAATGGTGAGGAAAGGTCACTGGGAACCAGCGCACCAACCTCAGACA

121 TcGATTTTGTTCCAGCCTTTTTTCCTGGGCAGGCCTCCCTATCACCTGCTGGTAGGCAGC
                                           <<<<<<<<<<<<<<<<<<

181 GGCAGGCCCACTGTCCTGC
```

101 )Whole sequence ::: rs2838551-rs2838552

TGACAGAAAAGTCTCAGAGCAGTGCCTTCTGAGCTCTTCTACACCAAGCAGGCAGAATGT
TCACTGCTAATGAGgCTGGAGCTGGTCCCCAGCAGTGGTAGGAAGCTTCCAaCAGGCTCA
GGCTGTGGGTGCTTGCAGGGGCACAGTGTGACGGCCACGGGCCTCAGAGCTCTGGTGGGC
T (SEQ ID NO: 292)

OLIGO           (SEQ ID NOs: 293, 294)
LEFT PRIMER           2     20    53.05    45.00    5.00    3.00
GACAGAAAAGTCTCAGAGCA

FIG. 6AV

```
RIGHT PRIMER        135    18    62.10    61.11    5.00    3.00
CAAGCACCCACAGCCTGA
SEQUENCE SIZE: 181
INCLUDED REGION SIZE: 181

PRODUCT SIZE: 134, PAIR ANY COMPL: 4.00, PAIR 3' COMPL: 3.00

1 TGACAGAAAAGTCTCAGAGCAGTGCCTTCTGAGCTCTTCTACACCAAGCAGGCAGAATGT
      >>>>>>>>>>>>>>>>>>>

61 TCACTGCTAATGAGgCTGGAGCTGGTCCCCAGCAGTGGTAGGAAGCTTCCAaCAGGCTCA
                                                               <<<

121 GGCTGTGGGTGCTTGCAGGGGCACAGTGTGACGGCCACGGGCCTCAGAGCTCTGGTGGGC
         <<<<<<<<<<<<<<<

181 T

102 )Whole sequence ::: rs8134902-rs8133874

ACATCTTTCTCAAATAAAGATAACAGCGATGTATTTTCACAAAAGCAAGAGCTTAGAAAG
TACTcCACCCAGGTATCCCTCTTGGAAAAAATaCTTAAGGAAATATGACAAATGGCAAAG
TGATTGTTATGGATGGAATGTTTGTATCCTCCCAAAATTCACATGTTGAGACCCTAATTC
CAATATG (SEQ ID NO: 295)

OLIGO             (SEQ ID NOs: 296, 297)
LEFT PRIMER        33    20    54.84    35.00    5.00    2.00
ATTTTCACAAAAGCAAGAGC
RIGHT PRIMER      155    20    54.97    40.00    3.00    0.00
TTGGGAGGATACAAACATTC
SEQUENCE SIZE: 187
INCLUDED REGION SIZE: 187

PRODUCT SIZE: 123, PAIR ANY COMPL: 4.00, PAIR 3' COMPL: 0.00

1 ACATCTTTCTCAAATAAAGATAACAGCGATGTATTTTCACAAAAGCAAGAGCTTAGAAAG
                                      >>>>>>>>>>>>>>>>>>>>

61 TACTcCACCCAGGTATCCCTCTTGGAAAAAATaCTTAAGGAAATATGACAAATGGCAAAG

121 TGATTGTTATGGATGGAATGTTTGTATCCTCCCAAAATTCACATGTTGAGACCCTAATTC
                               <<<<<<<<<<<<<<<<<<<<

181 CAATATG

103 )Whole sequence ::: rs425667-rs382478

AGGGGCATTCTACAAAACACCCAACCGGTCAAGGTCGCTGAGGCCAAGGAGAGATTGGGC
AACCGTCACAAACCAGAGAAGcCGAGGAGAcCTTTCAGCCAACGCCATGTGGGGTCCTGA
GCAGGACCCACCGGAAGTTGGTGCAGCTGCCTAAAGACCGTCCTGGCTGAGAAGAAACAG (SEQ ID
NO: 298)

OLIGO             (SEQ ID NOs: 299, 300)
```

FIG. 6AW

```
LEFT PRIMER        46   18   55.06   50.00   4.00   2.00
AAGGAGAGATTGGGCAAC
RIGHT PRIMER      178   19   54.85   52.63   3.00   1.00
GTTTCTTCTCAGCCAGGAC
SEQUENCE SIZE: 180
INCLUDED REGION SIZE: 180

PRODUCT SIZE: 133, PAIR ANY COMPL: 4.00, PAIR 3' COMPL: 0.00

1 AGGGGCATTCTACAAAACACCCAACCGGTCAAGGTCGCTGAGGCCAAGGAGAGATTGGGC
                                                 >>>>>>>>>>>>>>

61 AACCGTCACAAACCAGAGAAGcCGAGGAGAcCTTTCAGCCAACGCCATGTGGGGTCCTGA
      >>>

121 GCAGGACCCACCGGAAGTTGGTGCAGCTGCCTAAAGACCGTCCTGGCTGAGAAGAAACAG
                                             <<<<<<<<<<<<<<<<<<<
```

104 )Whole sequence ::: rs2838650-rs2838651

```
TGGCCCTGACCTGCCAGAGCTGTTGGCCTCCAGCTGGCGGGTAAAACCCACGGCCTTCTC
AGAACAGGTTTCTCAACACATGAGACAGAACACACCAGACTTCCaAGGGGAACACCTGGA
TGGAGCTGGTTACCCAGATcGTTCAACACCGAGGGGCAGCGGCTTGAGGGTCTTTCCACG
AAGGCTTGGATTAACAAGAGGAGCASRGGTCTCTCCAGGATGGGCCCA (SEQ ID NO: 301)

OLIGO              (SEQ ID NOs: 302, 303)
LEFT PRIMER        79   20   54.89   50.00   4.00   1.00
CATGAGACAGAACACACCAG
RIGHT PRIMER      199   20   54.61   40.00   5.00   3.00
TCTTGTTAATCCAAGCCTTC
SEQUENCE SIZE: 228
INCLUDED REGION SIZE: 228

PRODUCT SIZE: 121, PAIR ANY COMPL: 4.00, PAIR 3' COMPL: 1.00

1 TGGCCCTGACCTGCCAGAGCTGTTGGCCTCCAGCTGGCGGGTAAAACCCACGGCCTTCTC

61 AGAACAGGTTTCTCAACACATGAGACAGAACACACCAGACTTCCaAGGGGAACACCTGGA
                        >>>>>>>>>>>>>>>>>>>>

121 TGGAGCTGGTTACCCAGATcGTTCAACACCGAGGGGCAGCGGCTTGAGGGTCTTTCCACG
                                                                <

181 AAGGCTTGGATTAACAAGAGGAGCASRGGTCTCTCCAGGATGGGCCCA
      <<<<<<<<<<<<<<<<<<<<
```

105 )Whole sequence ::: rs2838654-rs1296489

```
CCACCCAGTGTCACGTCACGGCCCCGGCACGCCATCCACGGACCCTGGATGGAGCCCAGC
TGCCTCCaGGAGCCCAGTTTAACTACAAAGGAGCCCTGGCTGCCCGCCCCGCCCAGACGC
ACTGACCTGTTGTTCTCTGTGGCTGCTGATGGCCaTCCCCAACCACTGGTGACTCTTCC
CTGGGGCCCCAAGCTCAGCCCCTAACCCCCTGTTGCTGGAAGT (SEQ ID NO: 304)

OLIGO              (SEQ ID NOs: 305, 306)
LEFT PRIMER        37   18   62.56   66.67   5.00   2.00
CACGGACCCTGGATGGAG
```

FIG. 6AX

```
RIGHT PRIMER        183    18    53.14    55.56    3.00    2.00
CAGGGAAGAGTCACCAGT
SEQUENCE SIZE: 223
INCLUDED REGION SIZE: 223

PRODUCT SIZE: 147, PAIR ANY COMPL: 5.00, PAIR 3' COMPL: 2.00

1 CCACCCAGTGTCACGTCACGGCCCCGGCACGCCATCCACGGACCCTGGATGGAGCCCAGC
                                                  >>>>>>>>>>>>>>>>>

61 TGCCTCCaGGAGCGCAGTTTAACTACAAAGGAGCCCTGGCTGCCCGCCCCGCCCAGACGC

121 ACTGACCTGTTGTTCTCTGTGGCTGCTGATGGCCCaTCCCCAACCACTGGTGACTCTTCC
                                                   <<<<<<<<<<<<<<

181 CTGGGGCCCCAAGCTCAGCCCCTAACCCCCTGTTGCTGGAAGT
      <<<
```

106 )Whole sequence ::: rs2838659-rs1108261

```
CAGAGGACTGGGCTGCGGGGTCAGGAATGGGCACACTTCCTAACTGCAGGACACTCTAAG
GGCTTTGGTCATGCACACgCAGCCAAGAGAAGGTGTCGCTGaCACACAGCCTTCCAGGAG
CGGACTTGGAGACCTCGCCAAGGACCAGGACTCCCCAGCACTCACACTCCCTTAGGCGCT
GAAGTC (SEQ ID NO: 307)

OLIGO              (SEQ ID NOs: 308, 309)
LEFT PRIMER         53    20    55.48    45.00    4.00    2.00
ACTCTAAGGGCTTTGGTCAT
RIGHT PRIMER       175    20    56.02    55.00    3.00    1.00
CTAAGGGAGTGTGAGTGCTG
SEQUENCE SIZE: 186
INCLUDED REGION SIZE: 186

PRODUCT SIZE: 123, PAIR ANY COMPL: 4.00, PAIR 3' COMPL: 1.00

1 CAGAGGACTGGGCTGCGGGGTCAGGAATGGGCACACTTCCTAACTGCAGGACACTCTAAG
                                                         >>>>>>>>

61 GGCTTTGGTCATGCACACgCAGCCAAGAGAAGGTGTCGCTGaCACACAGCCTTCCAGGAG
      >>>>>>>>>>>>

121 CGGACTTGGAGACCTCGCCAAGGACCAGGACTCCCCAGCACTCACACTCCCTTAGGCGCT
                                           <<<<<<<<<<<<<<<<<<<<

181 GAAGTC
```

107 )Whole sequence ::: rs585587-rs585601

```
GAAGAGGACAACACGGGGCTGTCTGCAGAGCACCTGCCACGCGCCAGGCTCTGTGTCCAC
AAGCACGGCGGCTGCTCCCACATGACaGAGCTCGTGcGGCAGCTCCAGGACTGTCTGGTG
CCAGAGCCCCAGCTCTCCGCCAGCCCCAGGCCACTGTGCGAGGCCCTCAGTGAAGAGGGG
GCCGT (SEQ ID NO: 310)

OLIGO              (SEQ ID NOs: 311, 312)
```

FIG. 6AY

```
LEFT PRIMER          42    18    64.78    66.67    5.00    2.00
CGCCAGGCTCTGTGTCCA
RIGHT PRIMER        183    18    60.76    66.67    5.00    3.00
GGCCCCTCTTCACTGAG
SEQUENCE SIZE: 185
INCLUDED REGION SIZE: 185

PRODUCT SIZE: 142, PAIR ANY COMPL: 5.00, PAIR 3' COMPL: 3.00

1 GAAGAGGACAACACGGGGCTGTCTGCAGAGCACCTGCCACGCGCCAGGCTCTGTGTCCAC
                                               >>>>>>>>>>>>>>>>>>

61 AAGCACGGCGGCTGCTCCCACATGACaGAGCTCGTGcGGCAGCTCCAGGACTGTCTGGTG

121 CCAGAGCCCCAGCTCTCCGCCAGCCCCAGGCCACTGTGCGAGGCCCTCAGTGAAGAGGGG
                                                  <<<<<<<<<<<<<<

181 GCCGT
       <<<
```

108 )Whole sequence ::: rs9981033-rs4818998

TCTAAATAATGTTAATGATCAAATTTAGTCAGATCTCAATCTTCATATGTTAGTTGCCTT
CTTAaTAAATATTCTGTTTTCTTTATCGTTCTTTATTTGTATCTCcACCTTCATTTCTGA
TTAAATTAAGAAGTTTTGTCTCTTCCATTTAATAATTAATGTATTTAATAACC (SEQ ID NO: 313)

```
OLIGO            (SEQ ID NOs: 314, 315)
LEFT PRIMER          24    22    51.86    31.82    6.00    2.00
TTTAGTCAGATCTCAATCTTCA
RIGHT PRIMER        149    22    54.02    31.82    4.00    3.00
AATGGAAGAGACAAAACTTCTT
SEQUENCE SIZE: 173
INCLUDED REGION SIZE: 173

PRODUCT SIZE: 126, PAIR ANY COMPL: 5.00, PAIR 3' COMPL: 1.00

1 TCTAAATAATGTTAATGATCAAATTTAGTCAGATCTCAATCTTCATATGTTAGTTGCCTT
                                 >>>>>>>>>>>>>>>>>>>>>>

61 CTTAaTAAATATTCTGTTTTCTTTATCGTTCTTTATTTGTATCTCcACCTTCATTTCTGA

121 TTAAATTAAGAAGTTTTGTCTCTTCCATTTAATAATTAATGTATTTAATAACC
           <<<<<<<<<<<<<<<<<<<<<<
```

109 )Whole sequence ::: rs2838802-rs2838803

CACACTCCACACTGGCCCCACGCGGGTGGCGAAGGACTCAGCCAGAGCCTGGCAGGATCC
TGGGGTGTCTaTTTCCAAGGAATGTTCTGGAAGAAACATACACACATACTTGTTTGCCAG
ATTTACCTGTGTCGTcTTCCAGATGAGAAGCAGCCTGTGTCACTCCATAAGGGAGAGTGC
GTGCAGCATTGAGA (SEQ ID NO: 316)

```
OLIGO            (SEQ ID NOs: 317, 318)
LEFT PRIMER          31    18    55.96    61.11    5.00    3.00
GAAGGACTCAGCCAGAGC
```

FIG. 6AZ

```
RIGHT PRIMER        177    20    55.20    50.00    7.00    3.00
CTCTCCCTTATGGAGTGACA
SEQUENCE SIZE: 194
INCLUDED REGION SIZE: 194

PRODUCT SIZE: 147, PAIR ANY COMPL: 4.00, PAIR 3' COMPL: 0.00

1 CACACTCCACACTGGCCCCACGCGGGTGGCGAAGGACTCAGCCAGAGCCTGGCAGGATCC
```

FIG. 6AAA

```
                    >>>>>>>>>>>>>>>>>
     61 TGGGGTGTCTaTTTCCAAGGAATGTTCTGGAAGAAACATACACACATACTTGTTTGCCAG

121 ATTTACCTGTGTGGTcTTCCAGATGAGAAGCAGCCTGTGTCACTCCATAAGGGAGAGTGC
                                      <<<<<<<<<<<<<<<<<<<

181 GTGCAGCATTGAGA
```

110 )Whole sequence ::: rs2183596-rs2150452

AAGAAACTCCCAAGGAACGCATTGTCCCAAGTTGCTGCACCAGTCAGTGTACATTCCCAC
AAaCAGTGCATGAGAGTTCCTGTTGCTTGTGAAATAAATGGTCAGCATTCAGTGTTGTCA
GCTTTTAAAATTTTCTCCTTTCTAGTGGGCATGTAATGGTcTCACATTATAGTTTTAATT
TGCATTTTCCTGCTGACATGTGATACGGAACCTTCCTCCCATGCT (SEQ ID NO: 319)

```
OLIGO          (SEQ ID NOs: 320, 321)
LEFT PRIMER        39    19    50.19   47.37   6.00   2.00
ACCAGTCAGTGTACATTCC
RIGHT PRIMER      190    19    50.12   26.32   4.00   0.00
GGAAAATGCAAATTAAAAC
SEQUENCE SIZE: 225
INCLUDED REGION SIZE: 225

PRODUCT SIZE: 152, PAIR ANY COMPL: 4.00, PAIR 3' COMPL: 1.00

1 AAGAAACTCCCAAGGAACGCATTGTCCCAAGTTGCTGCACCAGTCAGTGTACATTCCCAC
                                              >>>>>>>>>>>>>>>>>>>

61 AAaCAGTGCATGAGAGTTCCTGTTGCTTGTGAAATAAATGGTCAGCATTCAGTGTTGTCA

121 GCTTTTAAAATTTTCTCCTTTCTAGTGGGCATGTAATGGTcTCACATTATAGTTTTAATT
                                                        <<<<<<<<<

181 TGCATTTTCCTGGTGACATGTGATACGGAACCTTCCTCCCATGCT
           <<<<<<<<<<
```

111 )Whole sequence ::: rs4599218-rs9978646

GTGCAATTTAATTACAAACGCTTAAATGGGGAGGTCAGGGGCAGAGGGATGATGTCACAA
ACACACCCAcGTGTGCTTGGTGCAAAACAGTAAAACAAACAGCAAGAAGgTCCATGAAGG
AAAGATCGCCTCTGTCAGTGGGAGTAATGAGAGTGGCTGATGGACAGGTG (SEQ ID NO: 322)

```
OLIGO          (SEQ ID NOs: 323, 324)
LEFT PRIMER        19    20    61.86   55.00   4.00   1.00
CGCTTAAATGGGGAGGTCAG
RIGHT PRIMER      168    20    60.83   60.00   3.00   0.00
CCTGTCCATCAGCCACTCTC
SEQUENCE SIZE: 170
INCLUDED REGION SIZE: 170

PRODUCT SIZE: 150, PAIR ANY COMPL: 5.00, PAIR 3' COMPL: 2.00
```

FIG. 6AAB

```
  1 GTGCAATTTAATTACAAACGCTTAAATGGGGAGGTCAGGGGCAGAGGGATGATGTCACAA
                       >>>>>>>>>>>>>>>>>>>>

61 ACACACCCAcGTGTGCTTGGTGCAAAACAGTAAAACAAACAGCAAGAAGgTCCATGAAGG

121 AAAGATCGCCTCTGTCAGTGGGAGTAATGAGAGTGGCTGATGGACAGGTG
                          <<<<<<<<<<<<<<<<<<<<
```

112 )Whole sequence ::: rs11702503-rs3827270

ACGCCAAGCAGGAGATGCCAGACACAGAGTCCATCCTGAGAGAGTCTGTTCCTGTCCAAG
CTCAGAAACACAGGAAGCcACCTGTGCTGTAGCAGCACaCGGAGATGCATCCTTTCTGGT
CCACCCCACGGCCCTCATTGCAGTCAGGGATCCTCTCCCAGAAAGTCCCTGCTGCCAGCC
CCTGCCCTT (SEQ ID NO: 325)

```
OLIGO              (SEQ ID NOs: 326, 327)
LEFT PRIMER            7      20     62.02    55.00   3.00   0.00
AGCAGGAGATGCCAGACACA
RIGHT PRIMER         125      20     63.37    55.00   5.00   4.00
GGTGGACCAGAAAGGATGCA
SEQUENCE SIZE: 189
INCLUDED REGION SIZE: 189
```

PRODUCT SIZE: 119, PAIR ANY COMPL: 3.00, PAIR 3' COMPL: 0.00

```
  1 ACGCCAAGCAGGAGATGCCAGACACAGAGTCCATCCTGAGAGAGTCTGTTCCTGTCCAAG
              >>>>>>>>>>>>>>>>>>>>

61 CTCAGAAACACAGGAAGCcACCTGTGCTGTAGCAGCACaCGGAGATGCATCCTTTCTGGT
                                                <<<<<<<<<<<<<<<<

121 CCACCCCACGGCCCTCATTGCAGTCAGGGATCCTCTCCCAGAAAGTCCCTGCTGCCAGCC
    <<<<

181 CCTGCCCTT
```

113 )Whole sequence ::: rs2839084-rs9984302

CATGAGAAAGACTTTGTTCCCATGAGAACAACAAGAGAAACTCAAACAAAATTAAAATTG
TACTTTTCTAAAAGACcGGGGTGGGGGTCGTGGTCAGGCAGCaGCATGAAGAAAGCCTTG
AGAACTGAATTCCAGAAAGAAACAAGCATAGGCAAGAAAGAGAGATGACA (SEQ ID NO: 328)

```
OLIGO              (SEQ ID NOs: 329, 330)
LEFT PRIMER           19      22     59.21    40.91   4.00   0.00
CCCATGAGAACAACAAGAGAAA
RIGHT PRIMER         162      20     55.46    45.00   4.00   2.00
CTCTTTCTTGCCTATGCTTG
SEQUENCE SIZE: 170
INCLUDED REGION SIZE: 170
```

PRODUCT SIZE: 144, PAIR ANY COMPL: 5.00, PAIR 3' COMPL: 3.00

```
  1 CATGAGAAAGACTTTGTTCCCATGAGAACAACAAGAGAAACTCAAACAAAATTAAAATTG
                        >>>>>>>>>>>>>>>>>>>>>>
```

FIG. 6AAC

```
 61 TACTTTTCTAAAAGACcGGGGTGGGGGTCGTGGTCAGGCAGCaGCATGAAGAAAGCCTTG

121 AGAACTGAATTCCAGAAAGAAACAAGCATAGGCAAGAAAGAGAGATGACA
    <<<<<<<<<<<<<<<<<<
```

114 )Whole sequence ::: rs2249057-rs2249060

```
AAGATTTAGAACAGCTGAAGCAGCGAGAAAAAACCCAGCATGAGTCaGAACTGGAGCAAC
TGAGGATTTATTTTGAAAAGAAGTTAAGGGATGCTGAGAAAACTTACCAAGAAGACCTAA
cCCTGTTACAGCAGAGGCTGCAGGGGGCGAGGGAAGATGCTCTTCTG (SEQ ID NO: 331)

OLIGO            (SEQ ID NOs: 332, 333)
LEFT PRIMER         12    21   63.07   47.62   6.00   0.00
CAGCTGAAGCAGCGAGAAAAA
RIGHT PRIMER       146    19   66.33   68.42   6.00   3.00
CCCCTGCAGCCTCTGCTGT
SEQUENCE SIZE: 167
INCLUDED REGION SIZE: 167

PRODUCT SIZE: 135, PAIR ANY COMPL: 7.00, PAIR 3' COMPL: 1.00

1 AAGATTTAGAACAGCTGAAGCAGCGAGAAAAAACCCAGCATGAGTCaGAACTGGAGCAAC
                 >>>>>>>>>>>>>>>>>>>>>

61 TGAGGATTTATTTTGAAAAGAAGTTAAGGGATGCTGAGAAAACTTACCAAGAAGACCTAA 121 cCCTGTTACAGCAGAGGCTGCAGGGGGCGAGGGAAGATGCTCTTCTG
          <<<<<<<<<<<<<<<<<<<
```

115 )Whole sequence ::: rs2839226-rs2839227

```
GGGAAACTGACTTGGCTTTTGCAAGGGTCATTGCTTCCTGATGCATGTTTAACTGTCCTG
TGTTCACTTTGTTGCcGCAGGTTTTTAGAGGAACGTAAAGAGATCaCCGAGAAATTCAGT
GCGGAACAAGATGCCTTCCTGCAGGAGGCCCAGGAGCAGCATGCCCGTGAGCTG (SEQ ID NO:
334)

OLIGO            (SEQ ID NOs: 335, 336)
LEFT PRIMER          1    22   64.29   50.00   3.00   2.00
GGGAAACTGACTTGGCTTTTGC
RIGHT PRIMER       135    20   64.63   55.00   3.00   2.00
GGCATCTTGTTCCGCACTGA
SEQUENCE SIZE: 174
INCLUDED REGION SIZE: 174

PRODUCT SIZE: 135, PAIR ANY COMPL: 4.00, PAIR 3' COMPL: 0.00

1 GGGAAACTGACTTGGCTTTTGCAAGGGTCATTGCTTCCTGATGCATGTTTAACTGTCCTG
      >>>>>>>>>>>>>>>>>>>>>>

61 TGTTCACTTTGTTGCcGCAGGTTTTTAGAGGAACGTAAAGAGATCaCCGAGAAATTCAGT
                                                          <<<<<

121 GCGGAACAAGATGCCTTCCTGCAGGAGGCCCAGGAGCAGCATGCCCGTGAGCTG
      <<<<<<<<<<<<<<<
```

FIG. 6AAD

116 )Whole sequence ::: rs10854482-rs2839261

CCCTGCACACTGACCTGCATGCCCTCGTCACCTGCACTCTGCATGCTCACCATCTGACGG
ACTCCTGCGAcGGGCATGGGAAGGTCGCCGCCGCCGGCAGCCtTGCGAGCACTTTGGATG
TGTGCACCCGGCATGCCAGGCCCGAGTCAACAGACTGGCCGACCTTGGCGTCCTG (SEQ ID NO: 337)

OLIGO          (SEQ ID NOs: 338, 339)
LEFT PRIMER           21     20    65.22   65.00   4.00   0.00
GCCCTCGTCACCTGCACTCT
RIGHT PRIMER         168     20    64.77   60.00   5.00   1.00
CCAAGGTCGGCCAGTCTGTT
SEQUENCE SIZE: 175
INCLUDED REGION SIZE: 175

PRODUCT SIZE: 148, PAIR ANY COMPL: 4.00, PAIR 3' COMPL: 0.00

```
    1 CCCTGCACACTGACCTGCATGCCCTCGTCACCTGCACTCTGCATGCTCACCATCTGACGG
                           >>>>>>>>>>>>>>>>>>>>

61 ACTCCTGCGAcGGGCATGGGAAGGTCGCCGCCGCCGGCAGCCtTGCGAGCACTTTGGATG

121 TGTGCACCCGGCATGCCAGGCCCGAGTCAACAGACTGGCCGACCTTGGCGTCCTG
                                      <<<<<<<<<<<<<<<<<<<<
```

117 )Whole sequence ::: rs2032111-rs718496

TTTATTGCTGAGTGGTATTCCATTTTATGGGTCCATTATAGTTTATTTGTCCAGACACTT
CATGGAAaGACATCAGTCTTTCCtGTTTTTCAATCATAAATTGATGTTTAATTTTAAAAT
TTTGGAATTGTAGAAGAAATGCAATTCTTTTTTCC (SEQ ID NO: 340)

OLIGO          (SEQ ID NOs: 341, 342)
LEFT PRIMER           28     22    53.65   31.82   4.00   3.00
TGGGTCCATTATAGTTTATTTG
RIGHT PRIMER         143     22    57.46   31.82   4.00   2.00
TGCATTTCTTCTACAATTCCAA
SEQUENCE SIZE: 155
INCLUDED REGION SIZE: 155

PRODUCT SIZE: 116, PAIR ANY COMPL: 5.00, PAIR 3' COMPL: 3.00

```
    1 TTTATTGCTGAGTGGTATTCCATTTTATGGGTCCATTATAGTTTATTTGTCCAGACACTT
                                  >>>>>>>>>>>>>>>>>>>>>>

61 CATGGAAaGACATCAGTCTTTCCtGTTTTTCAATCATAAATTGATGTTTAATTTTAAAAT

121 TTTGGAATTGTAGAAGAAATGCAATTCTTTTTTCC
         <<<<<<<<<<<<<<<<<<<<<<
```

118 )Whole sequence ::: rs2070434-rs2070435

CTTTGGTGCAGAATCATGCTGCAGGCAAGGTGGGCCCACCTCCCTGGAATTTCATCCCCC
cCGTCAGTTAAACCCATGGTGGTTTTATTTTCTAGGCCACCTGATCTGGGAGGACCACCT
CCAAGAAAAGCAGTCCTaTCGATGAACGGTCTAAGTTATGGTGTTATCAGAGTGGATACT

FIG. 6AAE

GAAGAAAAGTTGTCAGTCCTTACTGTTC (SEQ ID NO: 343)

```
OLIGO              (SEQ ID NOs: 344, 345)
LEFT PRIMER         33    20    66.57    60.00    4.00    3.00
GGCCCACCTCCCTGGAATTT
RIGHT PRIMER       176    22    54.26    40.91    4.00    0.00
TCCACTCTGATAACACCATAAC
SEQUENCE SIZE: 208
INCLUDED REGION SIZE: 208

PRODUCT SIZE: 144, PAIR ANY COMPL: 4.00, PAIR 3' COMPL: 1.00

1 CTTTGGTGCAGAATCATGCTGCAGGCAAGGTGGGCCCACCTCCCTGGAATTTCATCCCCC
                                      >>>>>>>>>>>>>>>>>>>>

61 cCGTCAGTTAAACCCATGGTGGTTTTATTTTCTAGGCCACCTGATCTGGGAGGACCACCT

121 CCAAGAAAAGCAGTCCTaTCGATGAACGGTCTAAGTTATGGTGTTATCAGAGTGGATACT
                                   <<<<<<<<<<<<<<<<<<<<<<

181 GAAGAAAAGTTGTCAGTCCTTACTGTTC
```

Mother carrying a non-trisomy 21 fetus:

| Subject 9 result for triplicate | p1 | p2 | p3 | p1/p2 | p1-p2 | HR |
|---|---|---|---|---|---|---|
| Buccal swab | 3293 | 3272 | ----- | 1.005 | ----- | ----- |
| Maternal serum | 2550 | 2323 | 230 | ----- | 227 | 0.99 + 0.16 |

FIG. 9A

Chromosome 13

| | | | |
|---|---|---|---|
| 31403476 | 31403533 | rs9590624 | rs384975 |
| 31493027 | 31493109 | rs9566986 | rs9562411 |
| 31527771 | 31527803 | rs411126 | rs398251 |
| 31605663 | 31605691 | rs9594995 | rs9594996 |
| 31608545 | 31608638 | rs9567251 | rs2106134 |
| 31619730 | 31619743 | rs204571 | rs204572 |
| 31629896 | 31629948 | rs537967 | rs689338 |
| 31631138 | 31631179 | rs17634824 | rs205004 |
| 31787968 | 31788026 | rs206119 | rs9562605 |
| 31896328 | 31896362 | rs206334 | rs169562 |
| 31934660 | 31934759 | rs1088550 | rs1081796 |
| 31997315 | 31997347 | rs535803 | rs45604 |
| 32219045 | 32219091 | rs12877579 | rs2051570 |
| 32380735 | 32380821 | rs766345 | rs766346 |
| 109352953 | 1.09E+08 | rs1763037 | rs376476 |
| 109354048 | 1.09E+08 | rs1763036 | rs1763034 |
| 109431411 | 1.09E+08 | rs9555657 | rs4771655 |
| 109436361 | 1.09E+08 | rs3742209 | rs1333982 |
| 109461769 | 1.09E+08 | rs7326063 | rs9559708 |
| 109477161 | 1.09E+08 | rs7986126 | rs9559710 |
| 109508102 | 1.1E+08 | rs7327434 | rs6492238 |
| 109515518 | 1.1E+08 | rs7334921 | rs7334783 |
| 109515760 | 1.1E+08 | rs4503663 | rs9559717 |
| 109516464 | 1.1E+08 | rs9559718 | rs9559719 |
| 109591078 | 1.1E+08 | rs7319307 | rs656533 |
| 109604491 | 1.1E+08 | rs1192201 | rs1192202 |
| 109606682 | 1.1E+08 | rs631428 | rs17588591 |
| 109606739 | 1.1E+08 | rs17588591 | rs613116 |
| 109609579 | 1.1E+08 | rs1192198 | rs8002698 |
| 109626892 | 1.1E+08 | rs1975514 | rs1562173 |
| 109655824 | 1.1E+08 | rs482757 | rs677877 |
| 109667423 | 1.1E+08 | rs6492246 | rs9515168 |
| 109677008 | 1.1E+08 | rs679958 | rs660433 |
| 109701188 | 1.1E+08 | rs72509 | rs751749 |
| 109715483 | 1.1E+08 | rs9559755 | rs903352 |
| 109715769 | 1.1E+08 | rs686642 | rs554882 |
| 109720695 | 1.1E+08 | rs6492252 | rs681777 |
| 109753036 | 1.1E+08 | rs7317591 | rs7317784 |
| 109759237 | 1.1E+08 | rs6492260 | rs2391824 |
| 109761032 | 1.1E+08 | rs4773145 | rs4773147 |
| 109783608 | 1.1E+08 | rs1556122 | rs7323190 |

FIG. 9B

Chromosome 18

| | | | |
|---|---|---|---|
| 2619101 | 2619162 | rs11080967 | rs11080969 |
| 2624848 | 2624943 | rs9303909 | rs7237881 |
| 2626514 | 2626605 | rs11660259 | rs11663451 |
| 2630789 | 2630803 | rs1568207 | rs1568208 |
| 2631809 | 2631858 | rs9958281 | rs7229070 |
| 2715198 | 2715268 | rs12605423 | rs673364 |
| 2781571 | 2781603 | rs585064 | rs9964586 |
| 2859839 | 2859916 | rs7241980 | rs679153 |
| 2862368 | 2862449 | rs9950998 | rs613796 |
| 2863900 | 2863939 | rs568289 | rs17553620 |
| 2864364 | 2864408 | rs680173 | rs642887 |
| 5762047 | 5762139 | rs1917929 | rs1917930 |
| 5913280 | 5913341 | rs1940613 | rs8097201 |
| 5942499 | 5942544 | rs523295 | rs626823 |
| 5945083 | 5945181 | rs3745091 | rs1940622 |
| 5945911 | 5945932 | rs2298535 | rs2298534 |
| 5946116 | 5946145 | rs3737351 | rs3737352 |
| 5946145 | 5946238 | rs3737352 | rs3737353 |
| 5954761 | 5954799 | rs606266 | rs1940611 |
| 6046847 | 6046888 | rs1785234 | rs1784816 |
| 72822082 | 72822160 | rs2282569 | rs470822 |
| 72822160 | 72822206 | rs470822 | rs470821 |
| 72823947 | 72823973 | rs470823 | rs470826 |
| 72825169 | 72825247 | rs2279078 | rs2279079 |
| 72825247 | 72825322 | rs2279079 | rs470550 |
| 72825322 | 72825413 | rs470550 | rs470546 |
| 72854057 | 72854154 | rs12406 | rs2282557 |
| 72876412 | 72876476 | rs8092433 | rs470549 |
| 72892082 | 72892105 | rs7232346 | rs11150996 |
| 72920062 | 72920157 | rs9964602 | rs9954182 |
| 72981791 | 72981859 | rs4890903 | rs1617137 |

FIG. 9C

Chromosome 22q11.2 region

| | | | |
|---|---|---|---|
| 16302735 | 16302770 | rs5746385 | rs5747145 |
| 16311483 | 16311566 | rs5747167 | rs1004973 |
| 16326168 | 16326202 | rs2522288 | rs5747187 |
| 16377569 | 16377619 | rs78914 | rs174302 |
| 16400773 | 16400796 | rs1003861 | rs5992732 |
| 16495251 | 16495277 | rs5747295 | rs5747296 |
| 16501246 | 16501334 | rs12628818 | rs11089197 |
| 16823681 | 16823699 | rs5992916 | rs5992917 |
| 16824657 | 16824734 | rs7286607 | rs1110659 |
| 16859382 | 16859447 | rs410456 | rs401910 |
| 16892282 | 16892325 | rs107321 | rs9605500 |
| 16898634 | 16898651 | rs4819660 | rs1076115 |
| 16913335 | 16913434 | rs455758 | rs458888 |
| 19634408 | 19634463 | rs737894 | rs1548410 |
| 20312249 | 20312340 | rs878825 | rs861857 |

SEQUENCE LISTING

<160> NUMBER OF SEQ ID NOS: 357

<210> SEQ ID NO 1
<211> LENGTH: 127
<212> TYPE: DNA
<213> ORGANISM: Homo sapiens

<400> SEQUENCE: 1
aacaaatctt catcttggaa tagcctgtga gaatgcctaa tcatctacga atgttacttt      60
ggcaccatct actggacaga ttaaataaca accaactcac tgtggattag acctacttct     120
atttcag                                                              127

<210> SEQ ID NO 2
<211> LENGTH: 20
<212> TYPE: DNA
<213> ORGANISM: Homo sapiens

```
<400> SEQUENCE: 2
atagcctgtg agaatgccta                                              20

<210> SEQ ID NO 3
<211> LENGTH: 20
<212> TYPE: DNA
<213> ORGANISM: Homo sapiens

<400> SEQUENCE: 3
atccacagtg agttggttgt                                              20

<210> SEQ ID NO 4
<211> LENGTH: 84
<212> TYPE: DNA
<213> ORGANISM: Homo sapiens

<400> SEQUENCE: 4
ttcctggaaa acaaaagtat ttctttcata gcccagctag catgataaat cagcgagtca   60
gaattctagc tttgttgtaa ggtt                                         84

<210> SEQ ID NO 5
<211> LENGTH: 20
<212> TYPE: DNA
<213> ORGANISM: Homo sapiens

<400> SEQUENCE: 5
tcctggaaaa caaaagtatt                                              20

<210> SEQ ID NO 6
<211> LENGTH: 21
<212> TYPE: DNA
<213> ORGANISM: Homo sapiens

<400> SEQUENCE: 6
aaccttacaa caaagctaga a                                            21

<210> SEQ ID NO 7
<211> LENGTH: 71
<212> TYPE: DNA
<213> ORGANISM: Homo sapiens

<400> SEQUENCE: 7
cactaagcct tggggatcca gctgcttaag gactaagacc gtatctagct ccttttagta   60
tttccacagc a                                                       71

<210> SEQ ID NO 8
<211> LENGTH: 20
<212> TYPE: DNA
<213> ORGANISM: Homo sapiens

<400> SEQUENCE: 8
actaagcctt ggggatccag                                              20

<210> SEQ ID NO 9
<211> LENGTH: 21
<212> TYPE: DNA
<213> ORGANISM: Homo sapiens

<400> SEQUENCE: 9
tgctgtggaa atactaaaag g                                            21
```

```
<210> SEQ ID NO 10
<211> LENGTH: 155
<212> TYPE: DNA
<213> ORGANISM: Homo sapiens

<400> SEQUENCE: 10
tcctccagag gtaatcctgt gatcagcact aacaccacat accagccctt tcatcagctt      60
gttggagaag catctttact tcccgccaag cagtgaccta gataccatct cacaccagtt     120
agaatcagga tcattaaaaa gtcaagaaaa aacag                                155

<210> SEQ ID NO 11
<211> LENGTH: 20
<212> TYPE: DNA
<213> ORGANISM: Homo sapiens

<400> SEQUENCE: 11
ctccagaggt aatcctgtga                                                  20

<210> SEQ ID NO 12
<211> LENGTH: 21
<212> TYPE: DNA
<213> ORGANISM: Homo sapiens

<400> SEQUENCE: 12
tggtgtgaga tggtatctag g                                                21

<210> SEQ ID NO 13
<211> LENGTH: 146
<212> TYPE: DNA
<213> ORGANISM: Homo sapiens

<400> SEQUENCE: 13
tccaagtata atccatgaat cttgtttaaa tatagatcaa ataaaccact ataccaaaaa      60
catcaaaaga caactgggta aatttttttaa atgactagct atttgatgtt aaggaagtaa    120
tgttactctc ttatatacaa tttgaa                                          146

<210> SEQ ID NO 14
<211> LENGTH: 22
<212> TYPE: DNA
<213> ORGANISM: Homo sapiens

<400> SEQUENCE: 14
gtataatcca tgaatcttgt tt                                               22

<210> SEQ ID NO 15
<211> LENGTH: 22
<212> TYPE: DNA
<213> ORGANISM: Homo sapiens

<400> SEQUENCE: 15
ttcaaattgt atataagaga gt                                               22

<210> SEQ ID NO 16
<211> LENGTH: 132
<212> TYPE: DNA
<213> ORGANISM: Homo sapiens

<400> SEQUENCE: 16
atggaaccga aacttcaagt agtttcatac gtatcacatt gacagttttc tctaagtttt      60
ctggtcttat gactcgttgt ttcattatta aaactgtgcc agtgtatgca tagggcttag     120
aaatttttta at                                                         132
```

```
<210> SEQ ID NO 17
<211> LENGTH: 18
<212> TYPE: DNA
<213> ORGANISM: Homo sapiens

<400> SEQUENCE: 17
atggaaccga aacttcaa                                                    18

<210> SEQ ID NO 18
<211> LENGTH: 22
<212> TYPE: DNA
<213> ORGANISM: Homo sapiens

<400> SEQUENCE: 18
ttaataatga acaacgagt ca                                                22

<210> SEQ ID NO 19
<211> LENGTH: 157
<212> TYPE: DNA
<213> ORGANISM: Homo sapiens

<400> SEQUENCE: 19
acaggatcct tcctgaagac accaccttgg ggagggtgaa ggataaagaa tttgatcaga        60
aatcaagggt ggtgagatac atgttaagga tgaataaact ggccttttag gattcttgct      120
aaaattagac aatgcagagg caaccacaga gtccaag                               157

<210> SEQ ID NO 20
<211> LENGTH: 19
<212> TYPE: DNA
<213> ORGANISM: Homo sapiens

<400> SEQUENCE: 20
ttcctgaaga caccaccttt                                                  19

<210> SEQ ID NO 21
<211> LENGTH: 18
<212> TYPE: DNA
<213> ORGANISM: Homo sapiens

<400> SEQUENCE: 21
cttggactct gtggttgc                                                    18

<210> SEQ ID NO 22
<211> LENGTH: 173
<212> TYPE: DNA
<213> ORGANISM: Homo sapiens

<400> SEQUENCE: 22
aatttccatt aaatcttgtt cgttgcttta ctgaggcact gaagttacca atgttccact       60
ggttgacctg cggggctatc tctaggttat gttactccag aaaatgaatt gtgtataaaa      120
gaggccttgg aggaaggcgt tttattcaca tcagttgttt tgcacattgc tta            173

<210> SEQ ID NO 23
<211> LENGTH: 20
<212> TYPE: DNA
<213> ORGANISM: Homo sapiens

<400> SEQUENCE: 23
actgaggcac tgaagttacc                                                  20
```

```
<210> SEQ ID NO 24
<211> LENGTH: 20
<212> TYPE: DNA
<213> ORGANISM: Homo sapiens

<400> SEQUENCE: 24
taagcaatgt gcaaaacaac                                                    20

<210> SEQ ID NO 25
<211> LENGTH: 191
<212> TYPE: DNA
<213> ORGANISM: Homo sapiens

<400> SEQUENCE: 25
tcggtttcag caggaaagtt attttttaata acttccctgt atttcttggt ttcagttatt       60
aattaactca ttaatgctaa actttgtgat cctaggttaa aaaacatatt caagatagct      120
tcagaatgtt tggtatacaa gtaggtctgg ctaaatataa gtgttagctt tctcaagcat      180
ctaaatgctg g                                                           191

<210> SEQ ID NO 26
<211> LENGTH: 20
<212> TYPE: DNA
<213> ORGANISM: Homo sapiens

<400> SEQUENCE: 26
gcaggaaagt tattttttaat                                                   20

<210> SEQ ID NO 27
<211> LENGTH: 21
<212> TYPE: DNA
<213> ORGANISM: Homo sapiens

<400> SEQUENCE: 27
tgcttgagaa agctaacact t                                                  21

<210> SEQ ID NO 28
<211> LENGTH: 166
<212> TYPE: DNA
<213> ORGANISM: Homo sapiens

<400> SEQUENCE: 28
aagttatttt taataacttc cctgtatttc ttggtttcag ttattaatta actcattaat        60
gctaaacttt gtgatcctag gttaaaaaac atattcaaga tagcttcaga atgtttggta      120
tacaagtagg tctggctaaa tataagtgtt agctttctca agcatc                     166

<210> SEQ ID NO 29
<211> LENGTH: 20
<212> TYPE: DNA
<213> ORGANISM: Homo sapiens

<400> SEQUENCE: 29 attttttaata acttccctgt                                                   20

<210> SEQ ID NO 30
<211> LENGTH: 20
<212> TYPE: DNA
<213> ORGANISM: Homo sapiens

<400> SEQUENCE: 30
cacttatatt tagccagacc                                                    20
```

```
<210> SEQ ID NO 31
<211> LENGTH: 152
<212> TYPE: DNA
<213> ORGANISM: Homo sapiens

<400> SEQUENCE: 31
attcattgtg tagaaagtgc ctgactcagt gtttggaaat tgtctgactt ttcctcatat    60
atagtgtggt ttcatgttat tgtatataag aactgacatg aactctgttt acaataatct   120
cccagtgcca taaagaccat aataaataat at                                 152

<210> SEQ ID NO 32
<211> LENGTH: 20
<212> TYPE: DNA
<213> ORGANISM: Homo sapiens

<400> SEQUENCE: 32
cagtgtttgg aaattgtctg                                               20

<210> SEQ ID NO 33
<211> LENGTH: 20
<212> TYPE: DNA
<213> ORGANISM: Homo sapiens

<400> SEQUENCE: 33
ggcactggga gattattgta                                               20

<210> SEQ ID NO 34
<211> LENGTH: 163
<212> TYPE: DNA
<213> ORGANISM: Homo sapiens

<400> SEQUENCE: 34
cactgggtcc tgttgttaag tacacataat accacacagg agaaaatcag gctaattgta    60
aatgggcaac ctacttaatt gtttcattaa aaagcataca gattacattt acactatagc   120
tagtcttgtt tgttttttta ttttgcaaaa gtaattacgg ccc                     163

<210> SEQ ID NO 35
<211> LENGTH: 20
<212> TYPE: DNA
<213> ORGANISM: Homo sapiens

<400> SEQUENCE: 35
tcctgttgtt aagtacacat                                               20

<210> SEQ ID NO 36
<211> LENGTH: 18
<212> TYPE: DNA
<213> ORGANISM: Homo sapiens

<400> SEQUENCE: 36
gggccgtaat tacttttg                                                 18

<210> SEQ ID NO 37
<211> LENGTH: 108
<212> TYPE: DNA
<213> ORGANISM: Homo sapiens

<400> SEQUENCE: 37
ctactcagta ggcactttgt gtctagaaac ttctgtgtca acggttttcc ctctctctgg    60
aattcatcag gacagaagtg attggtgtgg tggaagaggg ttgtgsta               108
```

```
<210> SEQ ID NO 38
<211> LENGTH: 21
<212> TYPE: DNA
<213> ORGANISM: Homo sapiens

<400> SEQUENCE: 38
actcagtagg cactttgtgt c                                              21

<210> SEQ ID NO 39
<211> LENGTH: 18
<212> TYPE: DNA
<213> ORGANISM: Homo sapiens

<400> SEQUENCE: 39
tcttccacca caccaatc                                                  18

<210> SEQ ID NO 40
<211> LENGTH: 144
<212> TYPE: DNA
<213> ORGANISM: Homo sapiens

<400> SEQUENCE: 40
tggcttttca aggtaaaat ttactaagtg tattaatatt ttaccaattt ccagccagga     60
gagtatgaat gttgcattat tacattgctt tgaaacaaag cattagtctt aattcagaag   120
tttaaattca gatgttaacg ttgc                                          144

<210> SEQ ID NO 41
<211> LENGTH: 19
<212> TYPE: DNA
<213> ORGANISM: Homo sapiens

<400> SEQUENCE: 41
tggcttttca aggtaaaa                                                  19

<210> SEQ ID NO 42
<211> LENGTH: 21
<212> TYPE: DNA
<213> ORGANISM: Homo sapiens

<400> SEQUENCE: 42
gcaacgttaa catctgaatt t                                              21

<210> SEQ ID NO 43
<211> LENGTH: 110
<212> TYPE: DNA
<213> ORGANISM: Homo sapiens

<400> SEQUENCE: 43
taagtattga agaaaggaga atttaaatta cttcatatac ctgataaagg aaaacatata    60
caaggcaaat aaacatctta gatcatgaca tataaaataa tagattatta               110

<210> SEQ ID NO 44
<211> LENGTH: 20
<212> TYPE: DNA
<213> ORGANISM: Homo sapiens

<400> SEQUENCE: 44
ttgaagaaag gagaatttaa                                                20

<210> SEQ ID NO 45
<211> LENGTH: 22
<212> TYPE: DNA
<213> ORGANISM: Homo sapiens
```

<400> SEQUENCE: 45
attttatatg tcatgatcta ag                                      22

<210> SEQ ID NO 46
<211> LENGTH: 165
<212> TYPE: DNA
<213> ORGANISM: Homo sapiens

<400> SEQUENCE: 46
tgcagagatt acaggtgtga gccaccgtgc ccagcctcat aaccgtttca actactttt     60 cacttgacaa gcagatgtga agttaacaaa gtcacccata tttgaaataa agatagtata    120
ttcctggggt aggcagaggc agttgaggat catgaaataa ctatg                    165

<210> SEQ ID NO 47
<211> LENGTH: 19
<212> TYPE: DNA
<213> ORGANISM: Homo sapiens

<400> SEQUENCE: 47
agagattaca ggtgtgagc                                          19

<210> SEQ ID NO 48
<211> LENGTH: 19
<212> TYPE: DNA
<213> ORGANISM: Homo sapiens

<400> SEQUENCE: 48
atgatcctca actgcctct                                          19

<210> SEQ ID NO 49
<211> LENGTH: 178
<212> TYPE: DNA
<213> ORGANISM: Homo sapiens

<400> SEQUENCE: 49
tgcaatgaaa ctcaaaagag aaaagttaac aggtgcaaaa ggtagtttta ttataaaagg     60
agggtaggca acaagaatat gtttaatttt tcttcctttt catgagtaag gacaagagtg    120
tcatatatgt gaatattttt atttaatttt aagtagaaat ctgttttaa aatatggg       178

<210> SEQ ID NO 50
<211> LENGTH: 20
<212> TYPE: DNA
<213> ORGANISM: Homo sapiens

<400> SEQUENCE: 50
tgaaactcaa aagagaaaag                                         20

<210> SEQ ID NO 51
<211> LENGTH: 20
<212> TYPE: DNA
<213> ORGANISM: Homo sapiens

<400> SEQUENCE: 51
acagatttct acttaaaatt                                         20

<210> SEQ ID NO 52
<211> LENGTH: 102
<212> TYPE: DNA
<213> ORGANISM: Homo sapiens -continued

```
<400> SEQUENCE: 52
ccaccattca tcaaaacttt gatactggac tcaattgtga atttgacttg aaatttgata      60
atgcttttgt tttactgttc tgctcagcaa aatagtacat gt                       102

<210> SEQ ID NO 53
<211> LENGTH: 20
<212> TYPE: DNA
<213> ORGANISM: Homo sapiens

<400> SEQUENCE: 53
caaaactttg atactggact                                                 20

<210> SEQ ID NO 54
<211> LENGTH: 19
<212> TYPE: DNA
<213> ORGANISM: Homo sapiens

<400> SEQUENCE: 54
acatgtacta ttttgctga                                                  19

<210> SEQ ID NO 55
<211> LENGTH: 166
<212> TYPE: DNA
<213> ORGANISM: Homo sapiens

<400> SEQUENCE: 55
gcctgcataa agtgaggatg gtgtagtaat tgggtatctc cagttataaa cacaaaaagc     60
atgatagagc tgggactgtg attgcaggaa agcaatagtc actccaaaag gagatcctca    120
tgatatgaat acggaagaaa caatatttcc tgctaatgta gtagcc                   166

<210> SEQ ID NO 56
<211> LENGTH: 20
<212> TYPE: DNA
<213> ORGANISM: Homo sapiens

<400> SEQUENCE: 56
cctgcataaa gtgaggatgg                                                 20

<210> SEQ ID NO 57
<211> LENGTH: 21
<212> TYPE: DNA
<213> ORGANISM: Homo sapiens

<400> SEQUENCE: 57
tgaggatctc cttttggagt g                                               21

<210> SEQ ID NO 58
<211> LENGTH: 154
<212> TYPE: DNA
<213> ORGANISM: Homo sapiens

<400> SEQUENCE: 58 gcaaagggt actctatgta atgaacatga cctggcagta ctgacatctc ctgagggact      60
gttagaagtg cagactcttg tatcttttct caagtctatg aaatctagac ttcattttaa    120
caagatgacc cgatatttac atacacatta aagt                                154

<210> SEQ ID NO 59
<211> LENGTH: 20
<212> TYPE: DNA
```

```
<400> SEQUENCE: 59
gcaaaggggt actctatgta                                              20

<210> SEQ ID NO 60
<211> LENGTH: 20
<212> TYPE: DNA
<213> ORGANISM: Homo sapiens

<400> SEQUENCE: 60
tatcgggtca tcttgttaaa                                              20

<210> SEQ ID NO 61
<211> LENGTH: 174
<212> TYPE: DNA
<213> ORGANISM: Homo sapiens

<400> SEQUENCE: 61
gtatctaaca aagctctgtc caaaattttg aatttctcgt taaaagcatc atgattatag   60
aacagaggtt acaatcaatt attcagtcac acaatcactc tcatcagtca ttaaggtgcg  120
tacctggtgt tccagttatt cagtgtggta taacaaacta cctggaactt aatg        174

<210> SEQ ID NO 62
<211> LENGTH: 22
<212> TYPE: DNA
<213> ORGANISM: Homo sapiens

<400> SEQUENCE: 62
tctaacaaag ctctgtccaa aa                                           22

<210> SEQ ID NO 63
<211> LENGTH: 21
<212> TYPE: DNA
<213> ORGANISM: Homo sapiens

<400> SEQUENCE: 63
ccacactgaa taactggaac a                                            21

<210> SEQ ID NO 64
<211> LENGTH: 202
<212> TYPE: DNA
<213> ORGANISM: Homo sapiens

<400> SEQUENCE: 64
agagtggtta agtgacttga tcaattcctc aggtggggat tcaagctctt aaagctgtag   60
actatgtcgt ccaaacaaac actgacatga atatgacttc caataggcaa gaaaagaggc  120
ctaggtcgag atactgcaag acatgcaagc aatctagtaa tggcataaaa cctgctatcc  180
gaattggcta aaattatgta tt                                           202

<210> SEQ ID NO 65
<211> LENGTH: 20
<212> TYPE: DNA
<213> ORGANISM: Homo sapiens

<400> SEQUENCE: 65
ggtggggatt caagctctta                                              20

<210> SEQ ID NO 66
<211> LENGTH: 22
<212> TYPE: DNA
<213> ORGANISM: Homo sapiens
```

<400> SEQUENCE: 66
ggatagcagg tttatgcca tt                                       22

<210> SEQ ID NO 67
<211> LENGTH: 156
<212> TYPE: DNA
<213> ORGANISM: Homo sapiens

<400> SEQUENCE: 67
ttctttctca cacaatgggt tccattccca ctactactcc attcaaattg aagtgccttc    60
aatgattatt aaaaaactct ctttaaaata gctcacgtaa ccttacatcc tttgactgag   120
gctcaactca tgtcaatgct tcagtatcaa cttttc                            156

<210> SEQ ID NO 68
<211> LENGTH: 21
<212> TYPE: DNA
<213> ORGANISM: Homo sapiens

<400> SEQUENCE: 68
aatgggttcc attcccacta c                                            21

<210> SEQ ID NO 69
<211> LENGTH: 20
<212> TYPE: DNA
<213> ORGANISM: Homo sapiens

<400> SEQUENCE: 69
tgagcctcag tcaaaggatg                                              20

<210> SEQ ID NO 70
<211> LENGTH: 202
<212> TYPE: DNA
<213> ORGANISM: Homo sapiens

<400> SEQUENCE: 70
atttgtaata acatttagta agtatttatt tgaggagttt gaattttgtt cttgtttatc    60
ttgttctctt tcttcgtaga ttagttggtg ttaacatcaa taggataacc ctttctttca   120
gcatatgtga atgaaataaa ccaattattg ccactttcca ggttaaccag aatatacata   180
gatacgagga cagtggactg tt                                           202

<210> SEQ ID NO 71
<211> LENGTH: 22
<212> TYPE: DNA
<213> ORGANISM: Homo sapiens

<400> SEQUENCE: 71
ttgaggagtt tgaattttgt tc                                           22

<210> SEQ ID NO 72
<211> LENGTH: 20
<212> TYPE: DNA
<213> ORGANISM: Homo sapiens

<400> SEQUENCE: 72
aacctggaaa gtggcaataa                                              20

<210> SEQ ID NO 73
<211> LENGTH: 171
<212> TYPE: DNA
<213> ORGANISM: Homo sapiens -continued

<400> SEQUENCE: 73
tagggcagag agagcaagca agctctctac cttctcatat aagggcacta atcccaccat    60
gaaggcgcca ctgtcatgac ctgattatgt cacaaagacc ccggggcaaa tattaccact   120
gtgaggagta cagttttagc atgtgaattt tggaagaaca caaacattta g            171

<210> SEQ ID NO 74
<211> LENGTH: 21
<212> TYPE: DNA
<213> ORGANISM: Homo sapiens

<400> SEQUENCE: 74
gcaagcaagc tctctaccct c                                              21

<210> SEQ ID NO 75
<211> LENGTH: 22
<212> TYPE: DNA
<213> ORGANISM: Homo sapiens

<400> SEQUENCE: 75
tgttcttcca aaattcacat gc                                             22

<210> SEQ ID NO 76
<211> LENGTH: 195
<212> TYPE: DNA
<213> ORGANISM: Homo sapiens

<400> SEQUENCE: 76
attctaattt taaatatcat tgatgtagaa cattctattt cactattcct tcattttatt    60
attatgggaa attatataca gttctccaga tttttaaagc cttgctaaca tgttttaagt   120
cacacaaata ttctcctgtg ggaaaatgac agtaatttag tgtgcaacaa ttatatagaa   180 ctattttttca aactt                                                    195

<210> SEQ ID NO 77
<211> LENGTH: 21
<212> TYPE: DNA
<213> ORGANISM: Homo sapiens

<400> SEQUENCE: 77
atttcactat tccttcattt t                                              21

<210> SEQ ID NO 78
<211> LENGTH: 22
<212> TYPE: DNA
<213> ORGANISM: Homo sapiens

<400> SEQUENCE: 78
taattgttgc acactaaatt ac                                             22

<210> SEQ ID NO 79
<211> LENGTH: 138
<212> TYPE: DNA
<213> ORGANISM: Homo sapiens

<400> SEQUENCE: 79
actgtcatgg acttaaacaa ttgtctttga attgtctttt ttcatacttt tatttgcatc    60
tttccactaa aaagatggca caaagtaatc ctagtttaca ttttttacca tgtaattcca   120
tattactttt tcctgaaa                                                  138

```
<210> SEQ ID NO 80
<211> LENGTH: 20
<212> TYPE: DNA
<213> ORGANISM: Homo sapiens

<400> SEQUENCE: 80
actgtcatgg acttaaacaa                                                   20

<210> SEQ ID NO 81
<211> LENGTH: 22
<212> TYPE: DNA
<213> ORGANISM: Homo sapiens

<400> SEQUENCE: 81
ttcaggaaaa agtaatatgg aa                                                22

<210> SEQ ID NO 82
<211> LENGTH: 119
<212> TYPE: DNA
<213> ORGANISM: Homo sapiens

<400> SEQUENCE: 82
aaagaaaaaa aagccacaga aatcagtcct agagaaaacc gatctatgag ctgcctgaaa       60
ataattataa ataactatc ataaaaatgc ccagtgagat aagaaaac acagacaac          119

<210> SEQ ID NO 83
<211> LENGTH: 21
<212> TYPE: DNA
<213> ORGANISM: Homo sapiens

<400> SEQUENCE: 83
aaaaagccac agaaatcagt c                                                 21

<210> SEQ ID NO 84
<211> LENGTH: 22
<212> TYPE: DNA
<213> ORGANISM: Homo sapiens

<400> SEQUENCE: 84
ttcttatatc tcactgggca tt                                                22

<210> SEQ ID NO 85
<211> LENGTH: 143
<212> TYPE: DNA
<213> ORGANISM: Homo sapiens

<400> SEQUENCE: 85
caaggtcaga gaagttatct tggatggtag aagagaagaa aggagaagaa aggataagca       60
gaaaatcaaa aagggcataa aaaaattact ggggaaaata attcttagtc actcaccatt      120
tcttatgttt gtgaaaacag aaa                                              143

<210> SEQ ID NO 86
<211> LENGTH: 22
<212> TYPE: DNA
<213> ORGANISM: Homo sapiens

<400> SEQUENCE: 86
ggatggtaga agagaagaaa gg                                                22

<210> SEQ ID NO 87
<211> LENGTH: 22
<212> TYPE: DNA
<213> ORGANISM: Homo sapiens
```

```
<400> SEQUENCE: 87
tcacaaacat aagaaatggt ga                                          22

<210> SEQ ID NO 88
<211> LENGTH: 136
<212> TYPE: DNA
<213> ORGANISM: Homo sapiens

<400> SEQUENCE: 88
gaccacaatt cacaaatgca aagatgcaga accaacctaa gtggccactg actaatgaga   60
ggataaagaa gatgtggcat atatatatca gggactacta ctcagccatt acaaggaaca  120
aaataatgtc ttttgc                                                 136

<210> SEQ ID NO 89
<211> LENGTH: 20
<212> TYPE: DNA
<213> ORGANISM: Homo sapiens

<400> SEQUENCE: 89
tgcaaagatg cagaaccaac                                              20

<210> SEQ ID NO 90
<211> LENGTH: 22
<212> TYPE: DNA
<213> ORGANISM: Homo sapiens

<400> SEQUENCE: 90
ttttgttcct tgtaatggct ga                                           22

<210> SEQ ID NO 91
<211> LENGTH: 160
<212> TYPE: DNA
<213> ORGANISM: Homo sapiens

<400> SEQUENCE: 91
gaccacaatt cacaaatgca aagatgcaga accaacctaa gtggccactg actaatgaga   60
ggataaagaa gatgtggcat atatacatca gggactactt ctcagccatt acaaggaaca  120
aaataatgtc ttttgcaaca acttggatag agctggaggc                        160

<210> SEQ ID NO 92
<211> LENGTH: 20
<212> TYPE: DNA
<213> ORGANISM: Homo sapiens

<400> SEQUENCE: 92
tgcaaagatg cagaaccaac                                              20

<210> SEQ ID NO 93
<211> LENGTH: 21
<212> TYPE: DNA
<213> ORGANISM: Homo sapiens

<400> SEQUENCE: 93
gcctccagct ctatccaagt t                                            21

<210> SEQ ID NO 94
<211> LENGTH: 160
<212> TYPE: DNA
<213> ORGANISM: Homo sapiens
```

<400> SEQUENCE: 94
aatcctagac cttggattgc aagagactcc ttaatatctt cccatgtcca catttccttc    60
acatagtttg aatgtggctt ctattatata cagatacaag attcaaatcc aacctctatg   120
atgactggtc ttgtgaataa gcagaagagg cactaacaat                         160

<210> SEQ ID NO 95
<211> LENGTH: 22
<212> TYPE: DNA
<213> ORGANISM: Homo sapiens

<400> SEQUENCE: 95
ccttaatatc ttcccatgtc ca                                             22

<210> SEQ ID NO 96
<211> LENGTH: 22
<212> TYPE: DNA
<213> ORGANISM: Homo sapiens

<400> SEQUENCE: 96
attgttagtg cctcttctgc tt                                             22

<210> SEQ ID NO 97
<211> LENGTH: 162
<212> TYPE: DNA
<213> ORGANISM: Homo sapiens

<400> SEQUENCE: 97
aagagaagtg aggtcagcag ctgcaagcca cctccgtcat ttagaaaagc ttcatgatgt    60
agtgtgtcgt ttcgatgtga cactgtctca cagagttaaa atgatgttaa ggaactgttc   120
aatggaaatt tagaaatttc tctttttctc aattttagtg ta                      162

<210> SEQ ID NO 98
<211> LENGTH: 20
<212> TYPE: DNA
<213> ORGANISM: Homo sapiens

<400> SEQUENCE: 98
gagaagtgag gtcagcagct                                                20

<210> SEQ ID NO 99
<211> LENGTH: 22
<212> TYPE: DNA
<213> ORGANISM: Homo sapiens

<400> SEQUENCE: 99
tttctaaatt tccattgaac ag                                             22

<210> SEQ ID NO 100
<211> LENGTH: 160
<212> TYPE: DNA
<213> ORGANISM: Homo sapiens

<400> SEQUENCE: 100
atggctgaat agtattccct tgtgtatata tctatttatc cttttattca ttgatggaca    60
cttaggctga ttttctctct tctcatggct ggcttctcat cacccttggg tcctcctgta   120
tcctcgtgta ataaagctct tccccaatat ctcgatagat                         160

```
<210> SEQ ID NO 101
<211> LENGTH: 22
<212> TYPE: DNA
<213> ORGANISM: Homo sapiens

<400> SEQUENCE: 101
ggctgaatag tattcccttg tg                                              22

<210> SEQ ID NO 102
<211> LENGTH: 20
<212> TYPE: DNA
<213> ORGANISM: Homo sapiens

<400> SEQUENCE: 102
tcgagatatt ggggaagagc                                                 20

<210> SEQ ID NO 103
<211> LENGTH: 199
<212> TYPE: DNA
<213> ORGANISM: Homo sapiens

<400> SEQUENCE: 103
cattttaact tgattacctc cacaaagact attccagaat aaggttatgt tctgaggtat     60
taggggttac aacttcaaca tatgaatttt gagtggacac aattcaaccc atagcacctc    120
cgtgtaagag ctgggaaggg aaagtggcta agttgtgcaa atgtgcacat tggttggaga   180
tgattaactt ctggcatgt                                                 199

<210> SEQ ID NO 104
<211> LENGTH: 22
<212> TYPE: DNA
<213> ORGANISM: Homo sapiens

<400> SEQUENCE: 104
cctccacaaa gactattcca ga                                              22

<210> SEQ ID NO 105
<211> LENGTH: 20
<212> TYPE: DNA
<213> ORGANISM: Homo sapiens

<400> SEQUENCE: 105
cactttccct tcccagctct                                                 20

<210> SEQ ID NO 106
<211> LENGTH: 157
<212> TYPE: DNA
<213> ORGANISM: Homo sapiens

<400> SEQUENCE: 106
agggggaaat tggcaatctg attctaaaat tcatacggaa aaaacaatg gagttagaat      60 aactaaaaca gtccgaaaa agaaaaagaa atggaggact aatgctacct gatttcaagt    120
cttatcttat aaatctacat caataaagga caagttg                            157

<210> SEQ ID NO 107
<211> LENGTH: 20
<212> TYPE: DNA
<213> ORGANISM: Homo sapiens

<400> SEQUENCE: 107
gaaattggca atctgattct                                                 20
```

```
<210> SEQ ID NO 108
<211> LENGTH: 21
<212> TYPE: DNA
<213> ORGANISM: Homo sapiens

<400> SEQUENCE: 108
caacttgtcc tttattgatg t                                              21

<210> SEQ ID NO 109
<211> LENGTH: 173
<212> TYPE: DNA
<213> ORGANISM: Homo sapiens

<400> SEQUENCE: 109
tctgtgtttg tctatgttga taaaacattg aaatgccaaa tagctcaaag gtcattcact    60
taagaaatct aagtactgat aacatcttag ccccgattct tcataggcat tgttaagcct   120
attataattt tggttcagag agaaggtaaa ctatattcca gacaggcata taa          173

<210> SEQ ID NO 110
<211> LENGTH: 22
<212> TYPE: DNA
<213> ORGANISM: Homo sapiens

<400> SEQUENCE: 110
ctatgttgat aaaacattga aa                                             22

<210> SEQ ID NO 111
<211> LENGTH: 20
<212> TYPE: DNA
<213> ORGANISM: Homo sapiens

<400> SEQUENCE: 111
gcctgtctgg aatatagttt                                                20

<210> SEQ ID NO 112
<211> LENGTH: 126
<212> TYPE: DNA
<213> ORGANISM: Homo sapiens

<400> SEQUENCE: 112
tgcagggcat ataatctaag ctgtaaacgt cctgtcagaa gacaacatat tcatcttgct    60
aaggtttaag ctatatgact ggcactgtgc tcaactcaga gtcattgaat gaacagtatt   120
tattta                                                              126

<210> SEQ ID NO 113
<211> LENGTH: 22
<212> TYPE: DNA
<213> ORGANISM: Homo sapiens

<400> SEQUENCE: 113
cagggcatat aatctaagct gt                                             22

<210> SEQ ID NO 114
<211> LENGTH: 21
<212> TYPE: DNA
<213> ORGANISM: Homo sapiens

<400> SEQUENCE: 114
caatgactct gagttgagca c                                              21
```

```
<210> SEQ ID NO 115
<211> LENGTH: 132
<212> TYPE: DNA
<213> ORGANISM: Homo sapiens

<400> SEQUENCE: 115
ttcacattat tcccttaaaa taaactctct ccctcccctc tcccgtctca accttgtccc    60
tttctttata taatgggtaa ttcgttaatg tcagcagaat agttttgggg ccataatggc   120
aagtatcacg tg                                                      132

<210> SEQ ID NO 116
<211> LENGTH: 19
<212> TYPE: DNA
<213> ORGANISM: Homo sapiens

<400> SEQUENCE: 116
aactctctcc ctcccctct                                                19

<210> SEQ ID NO 117
<211> LENGTH: 20
<212> TYPE: DNA
<213> ORGANISM: Homo sapiens

<400> SEQUENCE: 117
tatggcccca aaactattct                                               20

<210> SEQ ID NO 118
<211> LENGTH: 110
<212> TYPE: DNA
<213> ORGANISM: Homo sapiens

<400> SEQUENCE: 118
tcaggaagca acaagtactg ggcagattga tactgtagct aggctctagc tctatacctc    60
tagaataaat gttacaaact agcaacttga agctaaacc tggcccacag              110

<210> SEQ ID NO 119
<211> LENGTH: 20
<212> TYPE: DNA
<213> ORGANISM: Homo sapiens

<400> SEQUENCE: 119
acaagtactg ggcagattga                                               20

<210> SEQ ID NO 120
<211> LENGTH: 20
<212> TYPE: DNA
<213> ORGANISM: Homo sapiens

<400> SEQUENCE: 120
gccaggttta gctttcaagt                                               20

<210> SEQ ID NO 121
<211> LENGTH: 106
<212> TYPE: DNA
<213> ORGANISM: Homo sapiens

<400> SEQUENCE: 121
tggttcttga gaattttata tcaggagaaa cactgtcagt ctgtattgaa aggaacagag    60
aaaattcgaa attaaagaag actattaaac ctccaaaatt ctggca                 106
```

```
<210> SEQ ID NO 122
<211> LENGTH: 22
<212> TYPE: DNA
<213> ORGANISM: Homo sapiens

<400> SEQUENCE: 122
ttttatatca ggagaaacac tg                                              22

<210> SEQ ID NO 123
<211> LENGTH: 21
<212> TYPE: DNA
<213> ORGANISM: Homo sapiens

<400> SEQUENCE: 123
ccagaatttt ggaggtttaa t                                               21

<210> SEQ ID NO 124
<211> LENGTH: 171
<212> TYPE: DNA
<213> ORGANISM: Homo sapiens

<400> SEQUENCE: 124
gcatcaaact acacactgtc attcctcctt tatctccaaa agcttgaaaa ttcctcactt     60
gtatctcatt ctttctctct tagaaaactg atcacctctg atgaattaga acggaatgac    120
caagctttgg gagaggcaaa agaatctcgg tgttaaagac tcagagttta a             171

<210> SEQ ID NO 125
<211> LENGTH: 22
<212> TYPE: DNA
<213> ORGANISM: Homo sapiens

<400> SEQUENCE: 125
tgtcattcct cctttatctc ca                                              22

<210> SEQ ID NO 126
<211> LENGTH: 20
<212> TYPE: DNA
<213> ORGANISM: Homo sapiens

<400> SEQUENCE: 126
ttcttttgcc tctcccaaag                                                 20

<210> SEQ ID NO 127
<211> LENGTH: 163
<212> TYPE: DNA
<213> ORGANISM: Homo sapiens

<400> SEQUENCE: 127
ttgaaaatta agaaccctg gcacagtgtt gactggagcc acttacctta atagaaaata     60
aagctcacat atatccataa tgaaaagcag agaccagcac aaccatagtc acctgacagt    120
tttaaaatcc aaggccagga tcttctcaac tcaggcccac tca                      163

<210> SEQ ID NO 128
<211> LENGTH: 20
<212> TYPE: DNA
<213> ORGANISM: Homo sapiens

<400> SEQUENCE: 128
accctggcac agtgttgact                                                 20
```

<210> SEQ ID NO 129
<211> LENGTH: 20
<212> TYPE: DNA
<213> ORGANISM: Homo sapiens

<400> SEQUENCE: 129
tgggcctgag ttgagaagat                                              20

<210> SEQ ID NO 130
<211> LENGTH: 20
<212> TYPE: DNA
<213> ORGANISM: Homo sapiens

<400> SEQUENCE: 130
tttttcccat ttccaactct                                              20

<210> SEQ ID NO 131
<211> LENGTH: 122
<212> TYPE: DNA
<213> ORGANISM: Homo sapiens

<400> SEQUENCE: 131
aaaaaaaaag atgagacagg caggtgcgaa agaaataaaa gtcaaaactg atccagttgg   60
gaaactcaga attgacagtt acgtgtcctt tcatttattg atattttgag attcacaggg  120
gt                                                                122

<210> SEQ ID NO 132
<211> LENGTH: 20
<212> TYPE: DNA
<213> ORGANISM: Homo sapiens

<400> SEQUENCE: 132
aaaagatgag acaggcaggt                                              20

<210> SEQ ID NO 133
<211> LENGTH: 20
<212> TYPE: DNA
<213> ORGANISM: Homo sapiens

<400> SEQUENCE: 133
acccctgtga atctcaaaat                                              20

<210> SEQ ID NO 134
<211> LENGTH: 150
<212> TYPE: DNA
<213> ORGANISM: Homo sapiens

<400> SEQUENCE: 134
gagttaaata aagcacttgc ttctattgtt tgtacctaaa cttaacagaa cacagtaagt   60
aacaagtcat tgggatgcag aaaagaaaaa agagagtgaa ggaaggagaa aaggtgaagg  120
gagaatggaa gagaggaagg gagggaggaa                                  150

<210> SEQ ID NO 135
<211> LENGTH: 21
<212> TYPE: DNA
<213> ORGANISM: Homo sapiens

<400> SEQUENCE: 135
gcacttgctt ctattgtttg t                                            21

```
<210> SEQ ID NO 136
<211> LENGTH: 20
<212> TYPE: DNA
<213> ORGANISM: Homo sapiens

<400> SEQUENCE: 136
cccttcctct cttccattct                                              20

<210> SEQ ID NO 137
<211> LENGTH: 129
<212> TYPE: DNA
<213> ORGANISM: Homo sapiens

<400> SEQUENCE: 137
aaacgagcca ccagtgggag cactgcaggt atctgtgtga gacccgtact tcacaactcc  60
tgctttccct ccataaagta gcttgcattt tccacattga ctttgcagtt ctttggtatc  120
tgtattggt                                                          129

<210> SEQ ID NO 138
<211> LENGTH: 18
<212> TYPE: DNA
<213> ORGANISM: Homo sapiens

<400> SEQUENCE: 138
gtgggagcac tgcaggta                                                18

<210> SEQ ID NO 139
<211> LENGTH: 21
<212> TYPE: DNA
<213> ORGANISM: Homo sapiens

<400> SEQUENCE: 139
acagatacca aagaactgca a                                            21

<210> SEQ ID NO 140
<211> LENGTH: 145
<212> TYPE: DNA
<213> ORGANISM: Homo sapiens

<400> SEQUENCE: 140
tggacacctt tcaacttaga aatcataaac agattcattt ccttaaagtt aatgaaaaga  60
attaacagac cctcctcaaa aaagacatat atgcagccta caatcatatg aaaaaaagtt  120
caacattact gttcagcaaa tcaaa                                        145

<210> SEQ ID NO 141
<211> LENGTH: 20
<212> TYPE: DNA
<213> ORGANISM: Homo sapiens

<400> SEQUENCE: 141
tggacacctt tcaacttaga                                              20

<210> SEQ ID NO 142
<211> LENGTH: 22
<212> TYPE: DNA
<213> ORGANISM: Homo sapiens

<400> SEQUENCE: 142
gaacagtaat gttgaacttt tt                                           22
```

```
<210> SEQ ID NO 143
<211> LENGTH: 155
<212> TYPE: DNA
<213> ORGANISM: Homo sapiens

<400> SEQUENCE: 143
tggatacatt cctagaaata gatggaaact gctcttgcaa aaagcttagc acatgttaaa      60
aattttagaa acaatttgcc aaagtttatt tagtctagtg attttgacag gttaaatgga     120 cccttttgaga tcttttttcc tcaagtacaa aggct                                155

<210> SEQ ID NO 144
<211> LENGTH: 21
<212> TYPE: DNA
<213> ORGANISM: Homo sapiens

<400> SEQUENCE: 144
tcttgcaaaa agcttagcac a                                                21

<210> SEQ ID NO 145
<211> LENGTH: 21
<212> TYPE: DNA
<213> ORGANISM: Homo sapiens

<400> SEQUENCE: 145
aaaaagatct caaagggtcc a                                                21

<210> SEQ ID NO 146
<211> LENGTH: 119
<212> TYPE: DNA
<213> ORGANISM: Homo sapiens

<400> SEQUENCE: 146
gcttttgctg aacatcaagt ggtgagccag gactcaaagc cagatcttct tgtttccctg      60
ttaggtgttt gtagcacaac tggtatctgc agactatgct gctggaaggg ctagccgtc     119

<210> SEQ ID NO 147
<211> LENGTH: 20
<212> TYPE: DNA
<213> ORGANISM: Homo sapiens

<400> SEQUENCE: 147
gcttttgctg aacatcaagt                                                  20

<210> SEQ ID NO 148
<211> LENGTH: 19
<212> TYPE: DNA
<213> ORGANISM: Homo sapiens

<400> SEQUENCE: 148
ccttccagca gcatagtct                                                   19

<210> SEQ ID NO 149
<211> LENGTH: 161
<212> TYPE: DNA
<213> ORGANISM: Homo sapiens

<400> SEQUENCE: 149
actgtcctag aaaatccagg atgtgcagtg atcatgtatg aatgcatgga cctgcacaca      60
caggagtgaa caaaagaccc accctgcca ggtcaccact catatctcac cccagcccac     120
gctagctcac actcctcccc acacaccact gacctcatca t                         161
```

```
<210> SEQ ID NO 150
<211> LENGTH: 18
<212> TYPE: DNA
<213> ORGANISM: Homo sapiens

<400> SEQUENCE: 150
aaatccagga tgtgcagt                                                   18

<210> SEQ ID NO 151
<211> LENGTH: 19
<212> TYPE: DNA
<213> ORGANISM: Homo sapiens

<400> SEQUENCE: 151
atgatgaggt cagtggtgt                                                  19

<210> SEQ ID NO 152
<211> LENGTH: 124
<212> TYPE: DNA
<213> ORGANISM: Homo sapiens

<400> SEQUENCE: 152
cacatcacag atcatagtaa atggctttaa tttttttaacg aaatctcact actgcaaatg    60
cattgttgtc ctagctaatg aatgcataga gtattgcctg caaataata attgagattc    120 tatt                                                                 124

<210> SEQ ID NO 153
<211> LENGTH: 22
<212> TYPE: DNA
<213> ORGANISM: Homo sapiens

<400> SEQUENCE: 153
catcacagat catagtaaat gg                                              22

<210> SEQ ID NO 154
<211> LENGTH: 21
<212> TYPE: DNA
<213> ORGANISM: Homo sapiens

<400> SEQUENCE: 154
aattattatt ttgcaggcaa t                                               21

<210> SEQ ID NO 155
<211> LENGTH: 151
<212> TYPE: DNA
<213> ORGANISM: Homo sapiens

<400> SEQUENCE: 155
ttatcctcca catcctcatg aggcaaacac ctttcctacc ttaccgctcc ccagtggcct     60
ccctgttgcc ttcttattca agactaagac tctctagaat gttctttatc ctgagtccag    120
ctgattgtct atactaatat cagtacgggg t                                   151

<210> SEQ ID NO 156
<211> LENGTH: 20
<212> TYPE: DNA
<213> ORGANISM: Homo sapiens

<400> SEQUENCE: 156
catgaggcaa acacctttcc                                                 20
```

```
<210> SEQ ID NO 157
<211> LENGTH: 22
<212> TYPE: DNA
<213> ORGANISM: Homo sapiens

<400> SEQUENCE: 157
gctggactca ggataaagaa ca                                              22

<210> SEQ ID NO 158
<211> LENGTH: 145
<212> TYPE: DNA
<213> ORGANISM: Homo sapiens

<400> SEQUENCE: 158
agggtgcagc actttattat ggaagcctga gctgactaat acaggtgtct ctatatctca     60
ctgagggaaa gtgacaggaa agtaagaacc atttatgtcc aagagtccag aggagtcaac    120
cagattctgg gggaaaagaa ggtac                                          145

<210> SEQ ID NO 159
<211> LENGTH: 20
<212> TYPE: DNA
<213> ORGANISM: Homo sapiens

<400> SEQUENCE: 159
tggaagcctg agctgactaa                                                 20

<210> SEQ ID NO 160
<211> LENGTH: 20
<212> TYPE: DNA
<213> ORGANISM: Homo sapiens

<400> SEQUENCE: 160
ccttcttttc ccccagaatc                                                 20

<210> SEQ ID NO 161
<211> LENGTH: 154
<212> TYPE: DNA
<213> ORGANISM: Homo sapiens

<400> SEQUENCE: 161
tgagaattta ggagaacaga agatcagagg gctgcacagg ctaaactaga caatgagccc     60
atgcaagtaa gttaagagga gaagcgggta agtatgcacc tgctttgtct aggtgaccag    120
caagcattta gcaatagtct tttcaaaaca acag                                154

<210> SEQ ID NO 162
<211> LENGTH: 22
<212> TYPE: DNA
<213> ORGANISM: Homo sapiens

<400> SEQUENCE: 162
ttaggagaac agaagatcag ag                                              22

<210> SEQ ID NO 163
<211> LENGTH: 22
<212> TYPE: DNA
<213> ORGANISM: Homo sapiens

<400> SEQUENCE: 163
aaagactatt gctaaatgct tg                                              22
```

```
<210> SEQ ID NO 164
<211> LENGTH: 106
<212> TYPE: DNA
<213> ORGANISM: Homo sapiens

<400> SEQUENCE: 164
aaacaggcaa aataagcgta gggctgtgtg tgcaacagtt aatcataaag ccatcaccag     60
gagacgtcac tgggcgcctt ctggagtcta ccgtcctaa ctttgc                   106

<210> SEQ ID NO 165
<211> LENGTH: 20
<212> TYPE: DNA
<213> ORGANISM: Homo sapiens

<400> SEQUENCE: 165
taagcgtagg gctgtgtgtg                                                20

<210> SEQ ID NO 166
<211> LENGTH: 21
<212> TYPE: DNA
<213> ORGANISM: Homo sapiens

<400> SEQUENCE: 166
ggacggatag actccagaag g                                              21

<210> SEQ ID NO 167
<211> LENGTH: 105
<212> TYPE: DNA
<213> ORGANISM: Homo sapiens

<400> SEQUENCE: 167
gaatgacctt ggcactttta tcaaacatca actggccaca cacaggtgag tctacttctg    60
gacacttatc ctgttccatt catctgtata tctctatcct tacac                   105

<210> SEQ ID NO 168
<211> LENGTH: 23
<212> TYPE: DNA
<213> ORGANISM: Homo sapiens

<400> SEQUENCE: 168
gaatgacctt ggcactttta tca                                            23

<210> SEQ ID NO 169
<211> LENGTH: 27
<212> TYPE: DNA
<213> ORGANISM: Homo sapiens

<400> SEQUENCE: 169
aaggatagag atatacagat gaatgga                                        27

<210> SEQ ID NO 170
<211> LENGTH: 129
<212> TYPE: DNA
<213> ORGANISM: Homo sapiens

<400> SEQUENCE: 170
ctgctggaat aggctgcttg gccatgttct tggaagctac caccatatca aggtaatttc    60
ccacacaaca ttccagcccc tgctttcctc tctggcctta tctagggcca ttccccaact   120
caggtgaat                                                          129
```

```
<210> SEQ ID NO 171
<211> LENGTH: 20
<212> TYPE: DNA
<213> ORGANISM: Homo sapiens

<400> SEQUENCE: 171
ggccatgttc ttggaagcta                                                    20

<210> SEQ ID NO 172
<211> LENGTH: 20
<212> TYPE: DNA
<213> ORGANISM: Homo sapiens

<400> SEQUENCE: 172
ttcacctgag ttggggaatg                                                    20

<210> SEQ ID NO 173
<211> LENGTH: 138
<212> TYPE: DNA
<213> ORGANISM: Homo sapiens

<400> SEQUENCE: 173
acctttgttc catgcaccgc gcaaatacct gggaacccctt attgcccaac tcaagagcca       60
gagtcctctg tcatcatttt gcctctctcc taagtgagag gactgagtgc agacttggtg      120
tttgtgggtg aggcatgt                                                    138

<210> SEQ ID NO 174
<211> LENGTH: 18
<212> TYPE: DNA
<213> ORGANISM: Homo sapiens

<400> SEQUENCE: 174
catgcaccgc gcaaatac                                                      18

<210> SEQ ID NO 175
<211> LENGTH: 19
<212> TYPE: DNA
<213> ORGANISM: Homo sapiens

<400> SEQUENCE: 175
atgcctcacc cacaaacac                                                     19

<210> SEQ ID NO 176
<211> LENGTH: 159
<212> TYPE: DNA
<213> ORGANISM: Homo sapiens

<400> SEQUENCE: 176
ctcctgagtc caagcccttc tcactcacct ctttcttgaa ctaatttctt cctgtttttt        60
tccagtcctc ccttctgttc atgtctctcc tctgcacact tccatttttgt ggttcagaaa     120 atgtcaccgt cccagtcaca cttgccttat ggctgttgt                             159

<210> SEQ ID NO 177
<211> LENGTH: 20
<212> TYPE: DNA
<213> ORGANISM: Homo sapiens

<400> SEQUENCE: 177
tccaagccct tctcactcac                                                    20
```

```
<210> SEQ ID NO 178
<211> LENGTH: 20
<212> TYPE: DNA
<213> ORGANISM: Homo sapiens

<400> SEQUENCE: 178
ctgggacggt gacattttct                                                    20

<210> SEQ ID NO 179
<211> LENGTH: 132
<212> TYPE: DNA
<213> ORGANISM: Homo sapiens

<400> SEQUENCE: 179
cccaggaaga gtggaaagat taacctttgt gagccaaacc agtgacactt gattacttga        60
cagaactaat ccttctgtcc tgatgacaga acttcaacta cacaggtaca tgcaagctaa       120
tatctgttgt aa                                                           132

<210> SEQ ID NO 180
<211> LENGTH: 21
<212> TYPE: DNA
<213> ORGANISM: Homo sapiens

<400> SEQUENCE: 180
cccaggaaga gtggaaagat t                                                  21

<210> SEQ ID NO 181
<211> LENGTH: 21
<212> TYPE: DNA
<213> ORGANISM: Homo sapiens

<400> SEQUENCE: 181
ttagcttgca tgtacctgtg t                                                  21

<210> SEQ ID NO 182
<211> LENGTH: 165
<212> TYPE: DNA
<213> ORGANISM: Homo sapiens

<400> SEQUENCE: 182
gcctggcaag ctagatgggg tgaattttca cctgccacag ccgcaagtca aagccaccgg        60
cttctctctt ctccctccca ttgctcctga cagccagggt taatattttg cctcatgtaa       120
acagggaggc atccacccga gaatctcccc tcagcccaca taagc                       165

<210> SEQ ID NO 183
<211> LENGTH: 20
<212> TYPE: DNA
<213> ORGANISM: Homo sapiens

<400> SEQUENCE: 183
agctagatgg ggtgaatttt                                                    20

<210> SEQ ID NO 184
<211> LENGTH: 18
<212> TYPE: DNA
<213> ORGANISM: Homo sapiens

<400> SEQUENCE: 184
tgggctgagg ggagattc                                                      18
```

```
<210> SEQ ID NO 185
<211> LENGTH: 160
<212> TYPE: DNA
<213> ORGANISM: Homo sapiens

<400> SEQUENCE: 185
atcaagctaa ttaatgttat ctatcacttc acatagttca acctttttt gtggtgagag      60 tactgaagat ctactctctt agcaattttc aaatctaaaa tacattatta ttaacacagt    120
cactgtgccg tacgttagct ctgaggacct tattcatttt                          160

<210> SEQ ID NO 186
<211> LENGTH: 22
<212> TYPE: DNA
<213> ORGANISM: Homo sapiens

<400> SEQUENCE: 186
atcaagctaa ttaatgttat ct                                              22

<210> SEQ ID NO 187
<211> LENGTH: 20
<212> TYPE: DNA
<213> ORGANISM: Homo sapiens

<400> SEQUENCE: 187
aatgaataag gtcctcagag                                                 20

<210> SEQ ID NO 188
<211> LENGTH: 124
<212> TYPE: DNA
<213> ORGANISM: Homo sapiens

<400> SEQUENCE: 188
tttaatctga tcattgccct atgaggtagg gagtattctg attcccattt tataaataag     60
gaacccgagg cttagagagc atcagtgact tgttcaaggt cacccacagc tgtcaagtga    120
caga                                                                 124

<210> SEQ ID NO 189
<211> LENGTH: 21
<212> TYPE: DNA
<213> ORGANISM: Homo sapiens

<400> SEQUENCE: 189
tttaatctga tcattgccct a                                               21

<210> SEQ ID NO 190
<211> LENGTH: 18
<212> TYPE: DNA
<213> ORGANISM: Homo sapiens

<400> SEQUENCE: 190
agctgtgggt gaccttga                                                   18

<210> SEQ ID NO 191
<211> LENGTH: 128
<212> TYPE: DNA
<213> ORGANISM: Homo sapiens

<400> SEQUENCE: 191
tgtcccacca ttgtgtatta ggtttgtaga gcgtagacaa cttgcctttt tagtttgtag     60
gtttctgtat caagagaaga tgtgtgtggg cctaacctag attacaggat cctggacttc    120
aagtctga                                                             128
```

```
<210> SEQ ID NO 192
<211> LENGTH: 20
<212> TYPE: DNA
<213> ORGANISM: Homo sapiens

<400> SEQUENCE: 192
tgtcccacca ttgtgtatta                                                 20

<210> SEQ ID NO 193
<211> LENGTH: 20
<212> TYPE: DNA
<213> ORGANISM: Homo sapiens

<400> SEQUENCE: 193
tcagacttga agtccaggat                                                 20

<210> SEQ ID NO 194
<211> LENGTH: 128
<212> TYPE: DNA
<213> ORGANISM: Homo sapiens

<400> SEQUENCE: 194
tcatttgcta aggtcggata gctcctaatt ggcaaagtca cgatgggatc ccagggattc     60
tgaggatgaa gcctgtgttt aataactatt atgccaagtg agcattttca aatatatgag    120
agaaatta                                                            128

<210> SEQ ID NO 195
<211> LENGTH: 19
<212> TYPE: DNA
<213> ORGANISM: Homo sapiens

<400> SEQUENCE: 195
catttgctaa ggtcggata                                                  19

<210> SEQ ID NO 196
<211> LENGTH: 20
<212> TYPE: DNA
<213> ORGANISM: Homo sapiens

<400> SEQUENCE: 196
tatttgaaaa tgctcacttg                                                 20

<210> SEQ ID NO 197
<211> LENGTH: 159
<212> TYPE: DNA
<213> ORGANISM: Homo sapiens

<400> SEQUENCE: 197
cattgcttca ggggtgttag ttttgtgttc acaactagat tataaactcc tcttgcattc     60
ctgatggcag tgacttgaag gcatttattt gaagaataat agacatacag aaagggcac    120 atgtcataaa ggtacagctg gacgactttt cacaaagtg                          159

<210> SEQ ID NO 198
<211> LENGTH: 20
<212> TYPE: DNA
<213> ORGANISM: Homo sapiens

<400> SEQUENCE: 198
gcttcagggg tgttagtttt                                                 20
```

```
<210> SEQ ID NO 199
<211> LENGTH: 20
<212> TYPE: DNA
<213> ORGANISM: Homo sapiens

<400> SEQUENCE: 199
ctttgtgaaa agtcgtccag                                                   20

<210> SEQ ID NO 200
<211> LENGTH: 117
<212> TYPE: DNA
<213> ORGANISM: Homo sapiens

<400> SEQUENCE: 200
gagaggatgg tgccatcatg gaaagcatgg ggcagtcatg gagatgacgg agtagctcat       60
ggagaagata atgccatcat ggaaggcata gtgcagtcat ggagatgatg gtgcagc         117

<210> SEQ ID NO 201
<211> LENGTH: 18
<212> TYPE: DNA
<213> ORGANISM: Homo sapiens

<400> SEQUENCE: 201
ccatcatgga aagcatgg                                                     18

<210> SEQ ID NO 202
<211> LENGTH: 20
<212> TYPE: DNA
<213> ORGANISM: Homo sapiens

<400> SEQUENCE: 202
tcatctccat gactgcacta                                                   20

<210> SEQ ID NO 203
<211> LENGTH: 167
<212> TYPE: DNA
<213> ORGANISM: Homo sapiens

<400> SEQUENCE: 203
atggggcagt catggagatg acggagtagc tcatggagaa aataatgcca tcatggaagg       60
catagtgcag tcatggagat gatggtgcag ctcatggaga agatggtgcc atcatggaag      120
gcatggtgca atcatggagt agacagtgca gctgggccaa gattctc                   167

<210> SEQ ID NO 204
<211> LENGTH: 20
<212> TYPE: DNA
<213> ORGANISM: Homo sapiens

<400> SEQUENCE: 204
gagatgacgg agtagctcat                                                   20

<210> SEQ ID NO 205
<211> LENGTH: 18
<212> TYPE: DNA
<213> ORGANISM: Homo sapiens

<400> SEQUENCE: 205
cccagctgca ctgtctac                                                     18

<210> SEQ ID NO 206
<211> LENGTH: 128
<212> TYPE: DNA
<213> ORGANISM: Homo sapiens
```

```
<400> SEQUENCE: 206
gatgtgcctc tcttgttcca atcacaggac aggggtataa ctaggggcac tgtctatact    60
ggctgcactc tggccagtgc tgtcccaggt agattcatca gggtctagag cttcagctaa   120
cagcatga                                                            128

<210> SEQ ID NO 207
<211> LENGTH: 20
<212> TYPE: DNA
<213> ORGANISM: Homo sapiens

<400> SEQUENCE: 207
tcttgttcca atcacaggac                                                20

<210> SEQ ID NO 208
<211> LENGTH: 20
<212> TYPE: DNA
<213> ORGANISM: Homo sapiens

<400> SEQUENCE: 208
atgctgttag ctgaagctct                                                20

<210> SEQ ID NO 209
<211> LENGTH: 109
<212> TYPE: DNA
<213> ORGANISM: Homo sapiens

<400> SEQUENCE: 209
ttttattcat taagttgaaa gctcctaaag cagagggacc atattttat gtcccaactc     60 tccttaaggc cttgcctatg atagcacatc tcttcaatag aattgtcct               109

<210> SEQ ID NO 210
<211> LENGTH: 20
<212> TYPE: DNA
<213> ORGANISM: Homo sapiens

<400> SEQUENCE: 210
tgaaagctcc taaagcagag                                                20

<210> SEQ ID NO 211
<211> LENGTH: 20
<212> TYPE: DNA
<213> ORGANISM: Homo sapiens

<400> SEQUENCE: 211
ttgaagagat gtgctatcat                                                20

<210> SEQ ID NO 212
<211> LENGTH: 163
<212> TYPE: DNA
<213> ORGANISM: Homo sapiens

<400> SEQUENCE: 212
cacataacta ataaatttgt aagtatgtgc aacggctcac acttgcttcc agaatggcac    60
ctaaaaaaca gatttacctc tccccaaatt cagatatgga attaaatgta atgtcaggaa   120
aactgtctaa gagttggaaa tgggaaaaaa atgttctttt ggt                     163

<210> SEQ ID NO 213
<211> LENGTH: 21
<212> TYPE: DNA
<213> ORGANISM: Homo sapiens
```

-continued

```
<400> SEQUENCE: 213
aatttgtaag tatgtgcaac g                                               21

<210> SEQ ID NO 214
<211> LENGTH: 207
<212> TYPE: DNA
<213> ORGANISM: Homo sapiens

<400> SEQUENCE: 214
aaagaccagc ttttagctga acatcagggc tgccttcaga gtttaattac cgccctcccc     60
atggggccaa atgagccatc gactcctccc aagggggttc ggcttggtac tgatctttaa   120
gtaagtaaac gctaaaccag ctcatcttaa agcgcccaca tctgatttcc tgctctgctg   180
caagacagta ggtgactggt aatgacc                                        207

<210> SEQ ID NO 215
<211> LENGTH: 20
<212> TYPE: DNA
<213> ORGANISM: Homo sapiens

<400> SEQUENCE: 215
agggctgcct tcagagttta                                                 20

<210> SEQ ID NO 216
<211> LENGTH: 20
<212> TYPE: DNA
<213> ORGANISM: Homo sapiens

<400> SEQUENCE: 216
gcgctttaag atgagctggt                                                 20

<210> SEQ ID NO 217
<211> LENGTH: 192
<212> TYPE: DNA
<213> ORGANISM: Homo sapiens

<400> SEQUENCE: 217
actctgctcc cagtgtgaac atggggaaag ttgattaaac tctctgactt cagattcctc     60
atgtaaaatg tggggaaaca gctctgactt aatggtgtca ctgtgaggag taaatgaggt   120 agcatatttta aaggattttg tatagtgctg gtgacagtaa ccagccaata gatgatatag   180 ctagtaaatag ca                                                       192

<210> SEQ ID NO 218
<211> LENGTH: 20
<212> TYPE: DNA
<213> ORGANISM: Homo sapiens

<400> SEQUENCE: 218
tgaacatggg gaaagttgat                                                 20

<210> SEQ ID NO 219
<211> LENGTH: 22
<212> TYPE: DNA
<213> ORGANISM: Homo sapiens

<400> SEQUENCE: 219
tcaccagcac tatacaaaat cc                                              22
```

<210> SEQ ID NO 220
<211> LENGTH: 170
<212> TYPE: DNA
<213> ORGANISM: Homo sapiens

<400> SEQUENCE: 220
cttcactgac cacttcctta actgtccact ccgaaacacc ccttcttcct gttcttccaa    60
tacaccaaac tctttcttgc ctctgtgtgc ttgcccatgc tgttccttct ggcttcttcc    120
ttcacattca agtcttgact tagatgtcac ttgccaaggg agaccttgga    170

<210> SEQ ID NO 221
<211> LENGTH: 21
<212> TYPE: DNA
<213> ORGANISM: Homo sapiens

<400> SEQUENCE: 221
acttccttaa ctgtccactc c    21

<210> SEQ ID NO 222
<211> LENGTH: 19
<212> TYPE: DNA
<213> ORGANISM: Homo sapiens

<400> SEQUENCE: 222
ccttggcaag tgacatcta    19

<210> SEQ ID NO 223
<211> LENGTH: 181
<212> TYPE: DNA
<213> ORGANISM: Homo sapiens

<400> SEQUENCE: 223
aaacatccca atagacaaaa ctccaagaag agtcaaaaca agaataaagt acaggtcatc    60
ttttcttttg cactcctgac agcactttgt acatggtaat aataatctac caattaacta    120
cataagccac atggttttat catagtgtga agctttgtat ccagaaagga gagaaggctc    180
c    181

<210> SEQ ID NO 224
<211> LENGTH: 22
<212> TYPE: DNA
<213> ORGANISM: Homo sapiens

<400> SEQUENCE: 224
ccaagaagag tcaaaacaag aa    22

<210> SEQ ID NO 225
<211> LENGTH: 21
<212> TYPE: DNA
<213> ORGANISM: Homo sapiens

<400> SEQUENCE: 225
tctcctttct ggatacaaag c    21

<210> SEQ ID NO 226
<211> LENGTH: 149
<212> TYPE: DNA
<213> ORGANISM: Homo sapiens

```
<400> SEQUENCE: 226
ggcagaggca tggggtgcat agggatatgg ggtgggccag tttgctcctc agaccagaag      60
gggtgcagga ctccccccga tcaggatcat ggagaaaggt gtggacagag gaagggaggg     120
agggagaaat ggcagctgcc ctgcagtgg                                        149

<210> SEQ ID NO 227
<211> LENGTH: 20
<212> TYPE: DNA
<213> ORGANISM: Homo sapiens

<400> SEQUENCE: 227
ttgctcctca gaccagaagg                                                  20

<210> SEQ ID NO 228
<211> LENGTH: 20
<212> TYPE: DNA
<213> ORGANISM: Homo sapiens

<400> SEQUENCE: 228
ctcccttcct ctgtccacac                                                  20

<210> SEQ ID NO 229
<211> LENGTH: 165
<212> TYPE: DNA
<213> ORGANISM: Homo sapiens

<400> SEQUENCE: 229
cagggactaa gtgtctctga caatacattc agccactact acagtatgaa gccagcccct      60
catccccacc ttcagagacc cctggtgcct cagattcctc ggccattctg gagctgctgt     120
gcccgaggct tgtgtagttg gagatcattt tggcagtcag tgctg                     165

<210> SEQ ID NO 230
<211> LENGTH: 22
<212> TYPE: DNA
<213> ORGANISM: Homo sapiens

<400> SEQUENCE: 230
tgtctctgac aatacattca gc                                               22

<210> SEQ ID NO 231
<211> LENGTH: 20
<212> TYPE: DNA
<213> ORGANISM: Homo sapiens

<400> SEQUENCE: 231
ctgactgcca aaatgatctc                                                  20

<210> SEQ ID NO 232
<211> LENGTH: 181
<212> TYPE: DNA
<213> ORGANISM: Homo sapiens

<400> SEQUENCE: 232
cctgtctccg tgcgtgaaag ccggctccaa agtgccttct gtcctatctg ccttccgcac      60
ctggctttcc tgaaagaaag aaaacgcgtg gcttatcttt tcacggcacg ccaccttcac     120
tctcactttt tcttttctaa taaataccctc tggatgggtt agtggtaatc tctcctcaaa    180
c                                                                     181
```

```
<210> SEQ ID NO 233
<211> LENGTH: 20
<212> TYPE: DNA
<213> ORGANISM: Homo sapiens

<400> SEQUENCE: 233
gctccaaagt gccttctgtc                                               20

<210> SEQ ID NO 234
<211> LENGTH: 20
<212> TYPE: DNA
<213> ORGANISM: Homo sapiens

<400> SEQUENCE: 234
ccactaaccc atccagaggt                                               20

<210> SEQ ID NO 235
<211> LENGTH: 198
<212> TYPE: DNA
<213> ORGANISM: Homo sapiens

<400> SEQUENCE: 235
gggagcacaa cctaggcccc tcctggggag gtggtggagt cagaatcacg taagagacaa   60
agttccagtc cctcagtgcc ggctccattg tcccctggac ttcccttaca aaccacagat  120
gcaaagagag cacttctcgg aatctccaca cagccacggt ggagcactca acccacgcga  180
ccctcgggcg caggtgct                                                198

<210> SEQ ID NO 236
<211> LENGTH: 20
<212> TYPE: DNA
<213> ORGANISM: Homo sapiens

<400> SEQUENCE: 236
ctggggaggt ggtggagtca                                               20

<210> SEQ ID NO 237
<211> LENGTH: 20
<212> TYPE: DNA
<213> ORGANISM: Homo sapiens

<400> SEQUENCE: 237
gagtgctcca ccgtggctgt                                               20

<210> SEQ ID NO 238
<211> LENGTH: 161
<212> TYPE: DNA
<213> ORGANISM: Homo sapiens

<400> SEQUENCE: 238
cctgagaagc ttccagcaaa gcaccagcac gaaccgcccc acctccccac ctccccgcaa   60
gcgttgccgg gactgacaga ttacagagct ctggtccctc tgcactcctg ctctgccacc  120
cccagggtgt cagaatgtgc cccccacaca gtttccaaaa g                      161

<210> SEQ ID NO 239
<211> LENGTH: 18
<212> TYPE: DNA
<213> ORGANISM: Homo sapiens
```

```
<400> SEQUENCE: 239
aaagcaccag cacgaacc                                                  18

<210> SEQ ID NO 240
<211> LENGTH: 18
<212> TYPE: DNA
<213> ORGANISM: Homo sapiens

<400> SEQUENCE: 240
ggggcacatt ctgacacc                                                  18

<210> SEQ ID NO 241
<211> LENGTH: 162
<212> TYPE: DNA
<213> ORGANISM: Homo sapiens

<400> SEQUENCE: 241
atggagctgc tgcgccggcc tgagctctga tccctcctcc gacccagcct caccctgcaa    60
gcagcaccat gtggggctca gaatggggat cttaagggac cctccccaca acctcccgat   120 aagccttttcc acggagggcc caagcggaga caggagaaca ct                     162

<210> SEQ ID NO 242
<211> LENGTH: 19
<212> TYPE: DNA
<213> ORGANISM: Homo sapiens

<400> SEQUENCE: 242
ctgagctctg atccctcct                                                 19

<210> SEQ ID NO 243
<211> LENGTH: 18
<212> TYPE: DNA
<213> ORGANISM: Homo sapiens

<400> SEQUENCE: 243
ttctcctgtc tccgcttg                                                  18

<210> SEQ ID NO 244
<211> LENGTH: 194
<212> TYPE: DNA
<213> ORGANISM: Homo sapiens

<400> SEQUENCE: 244
actttcagaa tgtgctgcct tccacgtgtg aaccagactg agctcctttc tgccactgat    60
gttgaattgt ccatttgctc acatcagtgt ccacgtggca aatccacagg gcgtgggtgg   120
gatcctgcag tctagacaaa gccaaggagc accgctggag gccacgttgg gcttcccaat   180
ccacatgcaa accc                                                     194

<210> SEQ ID NO 245
<211> LENGTH: 20
<212> TYPE: DNA
<213> ORGANISM: Homo sapiens

<400> SEQUENCE: 245
cctttctgcc actgatgttg                                                20

<210> SEQ ID NO 246
<211> LENGTH: 19
<212> TYPE: DNA
<213> ORGANISM: Homo sapiens
```

<400> SEQUENCE: 246
ttgcatgtgg attgggaag                                          19

<210> SEQ ID NO 247
<211> LENGTH: 213
<212> TYPE: DNA
<213> ORGANISM: Homo sapiens

<400> SEQUENCE: 247
tctccagcca gcgtgtcaca aagccgctca cctgctcgtg tgagtgtctg aatgcacgtg    60
tttgagtgtc agaggcgtgt gaaccacagc aactcaatct tgaatagggg ctgggtaaag   120
tgaggctgag acctcccggg gctgcattcc cagatggtta aggcattcta agtcacaaga   180
tgagatagga agttcgcaca agacactggt cat                               213

<210> SEQ ID NO 248
<211> LENGTH: 20
<212> TYPE: DNA
<213> ORGANISM: Homo sapiens

<400> SEQUENCE: 248
tcacctgctc gtgtgagtgt                                          20

<210> SEQ ID NO 249
<211> LENGTH: 20
<212> TYPE: DNA
<213> ORGANISM: Homo sapiens

<400> SEQUENCE: 249
ccttaaccat ctgggaatgc                                          20

<210> SEQ ID NO 250
<211> LENGTH: 152
<212> TYPE: DNA
<213> ORGANISM: Homo sapiens

<400> SEQUENCE: 250
ttgagtcctc ttaagtagtt actatagtgg agaacttgag tcattctttg tagcgtgctt    60
cgtagagcag cgtgtttgtt agaaggattt gttaatcctg tatagggtct ttacgaaggc   120
tgttttcatg gaagcttctc tttgttgact cc                               152

<210> SEQ ID NO 251
<211> LENGTH: 22
<212> TYPE: DNA
<213> ORGANISM: Homo sapiens

<400> SEQUENCE: 251
tggagaactt gagtcattct tt                                       22

<210> SEQ ID NO 252
<211> LENGTH: 19
<212> TYPE: DNA
<213> ORGANISM: Homo sapiens

<400> SEQUENCE: 252
ggagtcaaca aagagaagc                                           19

<210> SEQ ID NO 253
<211> LENGTH: 174
<212> TYPE: DNA
<213> ORGANISM: Homo sapiens -continued

```
<400> SEQUENCE: 253
cattctctcc agctgcaaac tttcttcaac tttcctaaat tcttactaaa ttcagaggaa      60
taggataaag atcacttaga gaaagggtgc ttatggacat agcctgagtt tccttaacc      120 tctctgcaat gggtgctttt aactagcttc tacatggcaa gctgtttcag tttg           174

<210> SEQ ID NO 254
<211> LENGTH: 21
<212> TYPE: DNA
<213> ORGANISM: Homo sapiens

<400> SEQUENCE: 254
ctttcttcaa ctttcctaaa t                                                21

<210> SEQ ID NO 255
<211> LENGTH: 19
<212> TYPE: DNA
<213> ORGANISM: Homo sapiens

<400> SEQUENCE: 255
ttgccatgta gaagctagt                                                   19

<210> SEQ ID NO 256
<211> LENGTH: 175
<212> TYPE: DNA
<213> ORGANISM: Homo sapiens

<400> SEQUENCE: 256
ggacatctgg aactgcacca gcacagaacc gacacgttgt tactcatcgt cactcggcag      60
ggctgaagac caccagaact catgacaggc agacgtgcct ggcccagttg aggatgtagc     120
ttcagagcca agcgccagtc ctgttggcca cgtgggctgg gggcaggata gacca          175

<210> SEQ ID NO 257
<211> LENGTH: 19
<212> TYPE: DNA
<213> ORGANISM: Homo sapiens

<400> SEQUENCE: 257
accagcacag aaccgacac                                                   19

<210> SEQ ID NO 258
<211> LENGTH: 18
<212> TYPE: DNA
<213> ORGANISM: Homo sapiens

<400> SEQUENCE: 258
aacaggactg gcgcttgg                                                    18

<210> SEQ ID NO 259
<211> LENGTH: 182
<212> TYPE: DNA
<213> ORGANISM: Homo sapiens

<400> SEQUENCE: 259
ggctggttct gcccttggga ggtggttcct ttggctggac cagaatgtct gaagatgatc      60
aggagagggc caagggttgg ggggtgcccc atgtgcaccc tgagaattgc accaggcaca     120
gtgagcaact tcagccctcc ttgtgcagag ctgcagcgta cagtgccagc cctcgctggc     180
cc                                                                    182
```

```
<210> SEQ ID NO 260
<211> LENGTH: 20
<212> TYPE: DNA
<213> ORGANISM: Homo sapiens

<400> SEQUENCE: 260
cttgggaggt ggttcctttg                                              20

<210> SEQ ID NO 261
<211> LENGTH: 18
<212> TYPE: DNA
<213> ORGANISM: Homo sapiens

<400> SEQUENCE: 261
ctgcacaagg agggctga                                                18

<210> SEQ ID NO 262
<211> LENGTH: 155
<212> TYPE: DNA
<213> ORGANISM: Homo sapiens

<400> SEQUENCE: 262
gttctcactt tactgagaaa cctggcagct tctcaggcca ccgcccaggt cacctgctca   60
ccagcaacgt gaaccacagg aactgaggct gtgcgggagg cggctctgct ctgtgctggg  120 ccccctcct cctcactcac cctcttcagt caaag                              155

<210> SEQ ID NO 263
<211> LENGTH: 20
<212> TYPE: DNA
<213> ORGANISM: Homo sapiens

<400> SEQUENCE: 263
tactgagaaa cctggcagct                                              20

<210> SEQ ID NO 264
<211> LENGTH: 20
<212> TYPE: DNA
<213> ORGANISM: Homo sapiens

<400> SEQUENCE: 264
ctttgactga agagggtgag                                              20

<210> SEQ ID NO 265
<211> LENGTH: 180
<212> TYPE: DNA
<213> ORGANISM: Homo sapiens

<400> SEQUENCE: 265
ttagtattat tatttttcata tatatttttt ataataatca tatattcaat tttatcatca  60
agaaaaaagt tttaaaattc aaaatccttt catgtgcact gttttaaact taggtagaag  120
aaaaaaagtc actgaaaatc caagatgtaa taaacaggcc caacaaaggc caacaaactt  180

<210> SEQ ID NO 266
<211> LENGTH: 20
<212> TYPE: DNA
<213> ORGANISM: Homo sapiens

<400> SEQUENCE: 266 ttcaattta tcatcaagaa                                               20
```

```
<210> SEQ ID NO 267
<211> LENGTH: 20
<212> TYPE: DNA
<213> ORGANISM: Homo sapiens

<400> SEQUENCE: 267
ttgggcctgt ttattacatc                                                 20

<210> SEQ ID NO 268
<211> LENGTH: 196
<212> TYPE: DNA
<213> ORGANISM: Homo sapiens

<400> SEQUENCE: 268
agggaacatg gccttgccca cacagatttc agacatctgg ctccagaact gtgggaggac     60
acatttctgt tgtttagaac tgcatgtttt ttatactttg ttatggctgc cctaggcaac    120
taatacagat attattttcc acttctgaac ttagcaaaat atttttaaaa tgaaaattct    180
taaatgttgg cacagt                                                    196

<210> SEQ ID NO 269
<211> LENGTH: 20
<212> TYPE: DNA
<213> ORGANISM: Homo sapiens

<400> SEQUENCE: 269
ttgcccacac agatttcaga                                                 20

<210> SEQ ID NO 270
<211> LENGTH: 22
<212> TYPE: DNA
<213> ORGANISM: Homo sapiens

<400> SEQUENCE: 270
tgctaagttc agaagtggaa aa                                              22

<210> SEQ ID NO 271
<211> LENGTH: 120
<212> TYPE: DNA
<213> ORGANISM: Homo sapiens

<400> SEQUENCE: 271
ctggataaag gatgctacac gtccctggtg ggacagagca ggacggcagg ggatttcatt     60
acgccactca gaatggcagg caattgaaaa aacttataaa ttgtttattt ccagaatttt    120

<210> SEQ ID NO 272
<211> LENGTH: 20
<212> TYPE: DNA
<213> ORGANISM: Homo sapiens

<400> SEQUENCE: 272
ggataaagga tgctacacgt                                                 20

<210> SEQ ID NO 273
<211> LENGTH: 20
<212> TYPE: DNA
<213> ORGANISM: Homo sapiens

<400> SEQUENCE: 273
aaaattctgg aaataaacaa                                                 20
```

```
<210> SEQ ID NO 274
<211> LENGTH: 224
<212> TYPE: DNA
<213> ORGANISM: Homo sapiens

<400> SEQUENCE: 274
tgtcagtggt gtaatccgac tgtgaaagat cagtctaaca aaacagcggg gagagagagg      60
gctgaatcag agcaactagg tccaaagccg agggaaccac caacagatcc cctggtgacc     120
caacaagaaa tgctcacagt ctggacccag tcagagtctg caggacacag cagacattct     180
ggaagttaca acagccagga gcaagaggac gcatggcctg actg                      224

<210> SEQ ID NO 275
<211> LENGTH: 20
<212> TYPE: DNA
<213> ORGANISM: Homo sapiens

<400> SEQUENCE: 275
gggagagaga gggctgaatc                                                  20

<210> SEQ ID NO 276
<211> LENGTH: 21
<212> TYPE: DNA
<213> ORGANISM: Homo sapiens

<400> SEQUENCE: 276
gctcctggct gttgtaactt c                                                21

<210> SEQ ID NO 277
<211> LENGTH: 174
<212> TYPE: DNA
<213> ORGANISM: Homo sapiens

<400> SEQUENCE: 277
cgccagagca ccccttctca gaacagaaag cgtctctaca aagtgatccg gaagtgagtg      60
tgtgagggcg ctgcgtcctc cctgctcccc ttggagttgc cctttcttgc tcagatctgg     120
gtgccttggc cttgtcctgg gcccttccgc agcccccggg gtgatccccg ctag           174

<210> SEQ ID NO 278
<211> LENGTH: 19
<212> TYPE: DNA
<213> ORGANISM: Homo sapiens

<400> SEQUENCE: 278
ccagagcacc ccttctcag                                                   19

<210> SEQ ID NO 279
<211> LENGTH: 18
<212> TYPE: DNA
<213> ORGANISM: Homo sapiens

<400> SEQUENCE: 279
ggaagggccc aggacaag                                                    18

<210> SEQ ID NO 280
<211> LENGTH: 201
<212> TYPE: DNA
<213> ORGANISM: Homo sapiens

<400> SEQUENCE: 280
tatcttacgg atttgtcaac atcatttgag aagaagtcca taggctcagc agatttttat      60
gccaggtggg ccatggcata aaaatgtgaa gaatgtgctc acttagacaa tacctgtgct     120
```

| aaaattggaa caatacagag aagattagca aattaaaaca atgttaggaa gtcagtgtgg | 180 |
| tgaggtacgg tgcctcatgc c | 201 |

<210> SEQ ID NO 281
<211> LENGTH: 21
<212> TYPE: DNA
<213> ORGANISM: Homo sapiens

<400> SEQUENCE: 281

| cagcagattt ttatgccagg t | 21 |

<210> SEQ ID NO 282
<211> LENGTH: 20
<212> TYPE: DNA
<213> ORGANISM: Homo sapiens

<400> SEQUENCE: 282

| caccgtacct caccacactg | 20 |

<210> SEQ ID NO 283
<211> LENGTH: 275
<212> TYPE: DNA
<213> ORGANISM: Homo sapiens

<400> SEQUENCE: 283

| aggcagggcc ctccttgcca catgtaaagc tgcacagagc ggtcactata tgtgtttcca | 60 |
| tatttgcaat ccaaccacca ccaactgagt gtgcgtcctg atcagccgag cctgcccacg | 120 |
| gtggccacag gccctctaca ttctaatctc gagagcctga gcatgtacaa attaaacgaa | 180 |
| gcaaaacgac accacccagt tctggccgta ctataggagg tttccaggaa gggtttgtga | 240 |
| acataaacat aagctaggta acactccttt ctgaa | 275 |

<210> SEQ ID NO 284
<211> LENGTH: 20
<212> TYPE: DNA
<213> ORGANISM: Homo sapiens

<400> SEQUENCE: 284

| aaccaccacc aactgagtgt | 20 |

<210> SEQ ID NO 285
<211> LENGTH: 20
<212> TYPE: DNA
<213> ORGANISM: Homo sapiens

<400> SEQUENCE: 285

| cctcctatag tacggccaga | 20 |

<210> SEQ ID NO 286
<211> LENGTH: 230
<212> TYPE: DNA
<213> ORGANISM: Homo sapiens

<400> SEQUENCE: 286

| tcagagcatc gcctcagtgg ccatcaatag ctcggggggac tggattgctt ttggctgttc | 60 |
| aggtttgtcc ccagcctggg tggtagagat ggactcccca ttagggacca gtgctgcccg | 120 |
| gctacaggct tacttgacag ccaccccactg ggggtgccct cccctccccc agttgtcttc | 180 |
| catggggtgc cctctccccc agccgccttt cagaaggggc cctcccctcc | 230 |

```
<210> SEQ ID NO 287
<211> LENGTH: 20
<212> TYPE: DNA
<213> ORGANISM: Homo sapiens

<400> SEQUENCE: 287
tggattgctt ttggctgttc                                                 20

<210> SEQ ID NO 288
<211> LENGTH: 20
<212> TYPE: DNA
<213> ORGANISM: Homo sapiens

<400> SEQUENCE: 288
caccccatgg aagacaactg                                                 20

<210> SEQ ID NO 289
<211> LENGTH: 199
<212> TYPE: DNA
<213> ORGANISM: Homo sapiens

<400> SEQUENCE: 289
ctcatgctta catccttagc tgatcattaa actttgtgac catttcatgc tcactgcttt     60
cttgcccggg agctaatggt gaggaaaggt cactgggaac cagcgcacca acctcagaca    120
tcgattttgt tccagccttt tttcctgggc aggggtggct atcacctgct ggtaggcagc    180
ggcaggccca ctgtcctgc                                                 199

<210> SEQ ID NO 290
<211> LENGTH: 21
<212> TYPE: DNA
<213> ORGANISM: Homo sapiens

<400> SEQUENCE: 290
ttaaactttg tgaccatttc a                                               21

<210> SEQ ID NO 291
<211> LENGTH: 18
<212> TYPE: DNA
<213> ORGANISM: Homo sapiens

<400> SEQUENCE: 291
taccagcagg tgatagcc                                                   18

<210> SEQ ID NO 292
<211> LENGTH: 181
<212> TYPE: DNA
<213> ORGANISM: Homo sapiens

<400> SEQUENCE: 292
tgacagaaaa gtctcagagc agtgccttct gagctcttct acaccaagca ggcagaatgt     60
tcactgctaa tgaggctgga gctggtcccc agcagtggta ggaagcttcc aacaggctca    120
ggctgtgggt gcttgcaggg gcacagtgtg acggccacgg gcctcagagc tctggtgggc    180
t                                                                    181

<210> SEQ ID NO 293
<211> LENGTH: 20
<212> TYPE: DNA
<213> ORGANISM: Homo sapiens

<400> SEQUENCE: 293
gacagaaaag tctcagagca                                                 20
```

```
<210> SEQ ID NO 294
<211> LENGTH: 18
<212> TYPE: DNA
<213> ORGANISM: Homo sapiens

<400> SEQUENCE: 294
caagcaccca cagcctga                                                   18

<210> SEQ ID NO 295
<211> LENGTH: 187
<212> TYPE: DNA
<213> ORGANISM: Homo sapiens

<400> SEQUENCE: 295
acatctttct caaataaaga taacagcgat gtattttcac aaaagcaaga gcttagaaag     60
tactccaccc aggtatccct cttggaaaaa atacttaagg aaatatgaca aatggcaaag    120
tgattgttat ggatggaatg tttgtatcct cccaaaattc acatgttgag accctaattc    180
caatatg                                                              187

<210> SEQ ID NO 296
<211> LENGTH: 20
<212> TYPE: DNA
<213> ORGANISM: Homo sapiens

<400> SEQUENCE: 296
attttcacaa aagcaagagc                                                 20

<210> SEQ ID NO 297
<211> LENGTH: 20
<212> TYPE: DNA
<213> ORGANISM: Homo sapiens

<400> SEQUENCE: 297
ttgggaggat acaaacattc                                                 20

<210> SEQ ID NO 298
<211> LENGTH: 180
<212> TYPE: DNA
<213> ORGANISM: Homo sapiens

<400> SEQUENCE: 298 agggcattc tacaaaacac ccaaccggtc aaggtcgctg aggccaagga gagattgggc      60
aaccgtcaca aaccagagaa gccgaggaga cctttcagcc aacgccatgt ggggtcctga   120
gcaggaccca ccggaagttg gtgcagctgc ctaaagaccg tcctggctga aagaaacag    180

<210> SEQ ID NO 299
<211> LENGTH: 18
<212> TYPE: DNA
<213> ORGANISM: Homo sapiens

<400> SEQUENCE: 299
aaggagagat tgggcaac                                                   18

<210> SEQ ID NO 300
<211> LENGTH: 19
<212> TYPE: DNA
<213> ORGANISM: Homo sapiens

<400> SEQUENCE: 300
gtttcttctc agccaggac                                                  19
```

```
<210> SEQ ID NO 301
<211> LENGTH: 228
<212> TYPE: DNA
<213> ORGANISM: Homo sapiens

<400> SEQUENCE: 301
tggccctgac ctgccagagc tgttggcctc cagctggcgg gtaaaaccca cggccttctc      60
agaacaggtt tctcaacaca tgagacagaa cacaccagac ttccaagggg aacacctgga     120
tggagctggt tacccagatc gttcaacacc gaggggcagc ggcttgaggg tctttccacg     180
aaggcttgga ttaacaagag gagcasrggt ctctccagga tgggccca                  228

<210> SEQ ID NO 302
<211> LENGTH: 20
<212> TYPE: DNA
<213> ORGANISM: Homo sapiens

<400> SEQUENCE: 302
catgagacag aacacaccag                                                  20

<210> SEQ ID NO 303
<211> LENGTH: 20
<212> TYPE: DNA
<213> ORGANISM: Homo sapiens

<400> SEQUENCE: 303
tcttgttaat ccaagccttc                                                  20

<210> SEQ ID NO 304
<211> LENGTH: 223
<212> TYPE: DNA
<213> ORGANISM: Homo sapiens

<400> SEQUENCE: 304
ccacccagtg tcacgtcacg gccccggcac gccatccacg gaccctggat ggagcccagc      60
tgcctccagg agcgcagttt aactacaaag gagccctggc tgcccgcccc gcccagacgc     120
actgacctgt tgttctctgt ggctgctgat ggcccatccc caaccactgg tgactcttcc     180
ctggggcccc aagctcagcc cctaaccccc tgttgctgga agt                       223

<210> SEQ ID NO 305
<211> LENGTH: 18
<212> TYPE: DNA
<213> ORGANISM: Homo sapiens

<400> SEQUENCE: 305
cacggaccct ggatggag                                                    18

<210> SEQ ID NO 306
<211> LENGTH: 18
<212> TYPE: DNA
<213> ORGANISM: Homo sapiens

<400> SEQUENCE: 306
cagggaagag tcaccagt                                                    18

<210> SEQ ID NO 307
<211> LENGTH: 186
<212> TYPE: DNA
<213> ORGANISM: Homo sapiens
```

```
<400> SEQUENCE: 307
cagaggactg ggctgcgggg tcaggaatgg gcacacttcc taactgcagg acactctaag        60
ggctttggtc atgcacacgc agccaagaga aggtgtcgct gacacacagc cttccaggag       120
cggacttgga gacctcgcca aggaccagga ctccccagca ctcacactcc cttaggcgct       180
gaagtc                                                                  186

<210> SEQ ID NO 308
<211> LENGTH: 20
<212> TYPE: DNA
<213> ORGANISM: Homo sapiens

<400> SEQUENCE: 308
actctaaggg ctttggtcat                                                    20

<210> SEQ ID NO 309
<211> LENGTH: 20
<212> TYPE: DNA
<213> ORGANISM: Homo sapiens

<400> SEQUENCE: 309
ctaagggagt gtgagtgctg                                                    20

<210> SEQ ID NO 310
<211> LENGTH: 185
<212> TYPE: DNA
<213> ORGANISM: Homo sapiens

<400> SEQUENCE: 310
gaagaggaca acacggggct gtctgcagag cacctgccac gcgccaggct ctgtgtccac        60
aagcacggcg gctgctccca catgacagag ctcgtgcggc agctccagga ctgtctggtg       120
ccagagcccc agctctccgc cagccccagg ccactgtgcg aggccctcag tgaagagggg       180
gccgt                                                                   185

<210> SEQ ID NO 311
<211> LENGTH: 18
<212> TYPE: DNA
<213> ORGANISM: Homo sapiens

<400> SEQUENCE: 311
cgccaggctc tgtgtcca                                                      18

<210> SEQ ID NO 312
<211> LENGTH: 18
<212> TYPE: DNA
<213> ORGANISM: Homo sapiens

<400> SEQUENCE: 312 ggcccctct tcactgag                                                       18

<210> SEQ ID NO 313
<211> LENGTH: 173
<212> TYPE: DNA
<213> ORGANISM: Homo sapiens

<400> SEQUENCE: 313
tctaaataat gttaatgatc aaatttagtc agatctcaat cttcatatgt tagttgcctt        60
cttaataaat attctgtttt ctttatcgtt ctttatttgt atctccacct tcatttctga       120
ttaaattaag aagttttgtc tcttccattt aataattaat gtatttaata acc              173
```

```
<210> SEQ ID NO 314
<211> LENGTH: 22
<212> TYPE: DNA
<213> ORGANISM: Homo sapiens

<400> SEQUENCE: 314
tttagtcaga tctcaatctt ca                                              22

<210> SEQ ID NO 315
<211> LENGTH: 22
<212> TYPE: DNA
<213> ORGANISM: Homo sapiens

<400> SEQUENCE: 315
aatggaagag acaaaacttc tt                                              22

<210> SEQ ID NO 316
<211> LENGTH: 194
<212> TYPE: DNA
<213> ORGANISM: Homo sapiens

<400> SEQUENCE: 316
cacactccac actggcccca cgcgggtggc gaaggactca gccagagcct ggcaggatcc     60
tggggtgtct atttccaagg aatgttctgg aagaaacata cacacatact tgtttgccag    120
atttacctgt gtggtcttcc agatgagaag cagcctgtgt cactccataa gggagagtgc    180
gtgcagcatt gaga                                                      194

<210> SEQ ID NO 317
<211> LENGTH: 18
<212> TYPE: DNA
<213> ORGANISM: Homo sapiens

<400> SEQUENCE: 317
gaaggactca gccagagc                                                   18

<210> SEQ ID NO 318
<211> LENGTH: 20
<212> TYPE: DNA
<213> ORGANISM: Homo sapiens

<400> SEQUENCE: 318
ctctccctta tggagtgaca                                                 20

<210> SEQ ID NO 319
<211> LENGTH: 225
<212> TYPE: DNA
<213> ORGANISM: Homo sapiens

<400> SEQUENCE: 319
aagaaactcc caaggaacgc attgtcccaa gttgctgcac cagtcagtgt acattcccac     60
aaacagtgca tgagagttcc tgttgcttgt gaaataaatg gtcagcattc agtgttgtca    120
gcttttaaaa ttttctcctt tctagtgggc atgtaatggt ctcacattat agttttaatt    180 tgcatttttcc tggtgacatg tgatacggaa ccttcctccc atgct                   225

<210> SEQ ID NO 320
<211> LENGTH: 19
<212> TYPE: DNA
<213> ORGANISM: Homo sapiens
```

```
<400> SEQUENCE: 320
accagtcagt gtacattcc                                            19

<210> SEQ ID NO 321
<211> LENGTH: 19
<212> TYPE: DNA
<213> ORGANISM: Homo sapiens

<400> SEQUENCE: 321
ggaaaatgca aattaaaac                                            19

<210> SEQ ID NO 322
<211> LENGTH: 170
<212> TYPE: DNA
<213> ORGANISM: Homo sapiens

<400> SEQUENCE: 322
gtgcaattta attacaaacg cttaaatggg gaggtcaggg gcagagggat gatgtcacaa    60
acacacccac gtgtgcttgg tgcaaaacag taaaacaaac agcaagaagg tccatgaagg   120
aaagatcgcc tctgtcagtg ggagtaatga gagtggctga tggacaggtg              170

<210> SEQ ID NO 323
<211> LENGTH: 20
<212> TYPE: DNA
<213> ORGANISM: Homo sapiens

<400> SEQUENCE: 323
cgcttaaatg gggaggtcag                                           20

<210> SEQ ID NO 324
<211> LENGTH: 20
<212> TYPE: DNA
<213> ORGANISM: Homo sapiens

<400> SEQUENCE: 324
cctgtccatc agccactctc                                           20

<210> SEQ ID NO 325
<211> LENGTH: 189
<212> TYPE: DNA
<213> ORGANISM: Homo sapiens

<400> SEQUENCE: 325
acgccaagca ggagatgcca gacacagagt ccatcctgag agagtctgtt cctgtccaag    60
ctcagaaaca caggaagcca cctgtgctgt agcagcacac ggagatgcat cctttctggt   120
ccaccccacg gccctcattg cagtcaggga tcctctccca gaaagtccct gctgccagcc   180
cctgcccctt                                                   189

<210> SEQ ID NO 326
<211> LENGTH: 20
<212> TYPE: DNA
<213> ORGANISM: Homo sapiens

<400> SEQUENCE: 326
agcaggagat gccagacaca                                          20

<210> SEQ ID NO 327
<211> LENGTH: 20
<212> TYPE: DNA
<213> ORGANISM: Homo sapiens
```

```
<400> SEQUENCE: 327
ggtggaccag aaaggatgca                                               20

<210> SEQ ID NO 328
<211> LENGTH: 170
<212> TYPE: DNA
<213> ORGANISM: Homo sapiens

<400> SEQUENCE: 328
catgagaaag actttgttcc catgagaaca caagagaaa ctcaaacaaa attaaaattg    60
tacttttcta aaagaccggg gtggggtcg tggtcaggca gcagcatgaa gaaagccttg   120
agaactgaat tccagaaaga aacaagcata ggcaagaaag agagatgaca              170

<210> SEQ ID NO 329
<211> LENGTH: 22
<212> TYPE: DNA
<213> ORGANISM: Homo sapiens

<400> SEQUENCE: 329
cccatgagaa caacaagaga aa                                            22

<210> SEQ ID NO 330
<211> LENGTH: 20
<212> TYPE: DNA
<213> ORGANISM: Homo sapiens

<400> SEQUENCE: 330
ctctttcttg cctatgcttg                                               20

<210> SEQ ID NO 331
<211> LENGTH: 167
<212> TYPE: DNA
<213> ORGANISM: Homo sapiens

<400> SEQUENCE: 331
aagatttaga acagctgaag cagcgagaaa aaacccagca tgagtcagaa ctggagcaac    60
tgaggattta ttttgaaaag aagttaaggg atgctgagaa aacttaccaa gaagacctaa   120
ccctgttaca gcagaggctg caggggggcga gggaagatgc tcttctg                 167

<210> SEQ ID NO 332
<211> LENGTH: 21
<212> TYPE: DNA
<213> ORGANISM: Homo sapiens

<400> SEQUENCE: 332
cagctgaagc agcgagaaaa a                                             21

<210> SEQ ID NO 333
<211> LENGTH: 19
<212> TYPE: DNA
<213> ORGANISM: Homo sapiens

<400> SEQUENCE: 333
cccctgcagc ctctgctgt                                                19

<210> SEQ ID NO 334
<211> LENGTH: 174
<212> TYPE: DNA
<213> ORGANISM: Homo sapiens
```

```
<400> SEQUENCE: 334
gggaaactga cttggctttt gcaagggtca ttgcttcctg atgcatgttt aactgtcctg      60
tgttcacttt gttgccgcag gttttagag gaacgtaaag agatcaccga gaaattcagt     120
gcggaacaag atgccttcct gcaggaggcc caggagcagc atgcccgtga gctg          174

<210> SEQ ID NO 335
<211> LENGTH: 22
<212> TYPE: DNA
<213> ORGANISM: Homo sapiens

<400> SEQUENCE: 335
gggaaactga cttggctttt gc                                               22

<210> SEQ ID NO 336
<211> LENGTH: 20
<212> TYPE: DNA
<213> ORGANISM: Homo sapiens

<400> SEQUENCE: 336
ggcatcttgt tccgcactga                                                  20

<210> SEQ ID NO 337
<211> LENGTH: 175
<212> TYPE: DNA
<213> ORGANISM: Homo sapiens

<400> SEQUENCE: 337
ccctgcacac tgacctgcat gccctcgtca cctgcactct gcatgctcac catctgacgg      60
actcctgcga cgggcatggg aaggtcgccg ccgccggcag ccttgcgagc actttggatg    120
tgtgcacccg gcatgccagg cccgagtcaa cagactggcc gaccttggcg tcctg         175

<210> SEQ ID NO 338
<211> LENGTH: 20
<212> TYPE: DNA
<213> ORGANISM: Homo sapiens

<400> SEQUENCE: 338
gccctcgtca cctgcactct                                                  20

<210> SEQ ID NO 339
<211> LENGTH: 20
<212> TYPE: DNA
<213> ORGANISM: Homo sapiens

<400> SEQUENCE: 339
ccaaggtcgg ccagtctgtt                                                  20

<210> SEQ ID NO 340
<211> LENGTH: 155
<212> TYPE: DNA
<213> ORGANISM: Homo sapiens

<400> SEQUENCE: 340
tttattgctg agtggtattc cattttatgg gtccattata gtttatttgt ccagacactt      60
catggaaaga catcagtgtt tcctgttttt caatcataaa ttgatgttta atttaaaat     120 tttggaattg tagaagaaat gcaattcttt tttcc                                155
```

```
<210> SEQ ID NO 341
<211> LENGTH: 22
<212> TYPE: DNA
<213> ORGANISM: Homo sapiens

<400> SEQUENCE: 341
tgggtccatt atagtttatt tg                                              22

<210> SEQ ID NO 342
<211> LENGTH: 22
<212> TYPE: DNA
<213> ORGANISM: Homo sapiens

<400> SEQUENCE: 342
tgcatttctt ctacaattcc aa                                              22

<210> SEQ ID NO 343
<211> LENGTH: 208
<212> TYPE: DNA
<213> ORGANISM: Homo sapiens

<400> SEQUENCE: 343
ctttggtgca gaatcatgct gcaggcaagg tgggcccacc tccctggaat ttcatccccc     60
ccgtcagtta aacccatggt ggttttattt tctaggccac ctgatctggg aggaccacct    120
ccaagaaaag cagtcctatc gatgaacggt ctaagttatg gtgttatcag agtggatact    180
gaagaaaagt tgtcagtcct tactgttc                                       208

<210> SEQ ID NO 344
<211> LENGTH: 20
<212> TYPE: DNA
<213> ORGANISM: Homo sapiens

<400> SEQUENCE: 344
ggcccacctc cctggaattt                                                 20

<210> SEQ ID NO 345
<211> LENGTH: 22
<212> TYPE: DNA
<213> ORGANISM: Homo sapiens

<400> SEQUENCE: 345
tccactctga taacaccata ac                                              22

<210> SEQ ID NO 346
<211> LENGTH: 232
<212> TYPE: DNA
<213> ORGANISM: Homo sapiens

<400> SEQUENCE: 346
atcacctggt ttggtgcatc ctcgcagaaa gagagccata cagtgaagtg gaaacacacc     60
caaaagctct gcaatattcc tagaagttct cgaatctcct ccttaacaga gctgcagaag    120
ggaaacacag acaggaagca cctgtttgac tcagacagca gccctaatgc agtgccactc    180
aggagcattc cctcatttga agaccccccca attcatgaa attatcaacc cc            232

<210> SEQ ID NO 347
<211> LENGTH: 20
<212> TYPE: DNA
<213> ORGANISM: Homo sapiens

<400> SEQUENCE: 347
acacccaaaa gctctgcaat                                                 20
```

<210> SEQ ID NO 348
<211> LENGTH: 20
<212> TYPE: DNA
<213> ORGANISM: Homo sapiens

<400> SEQUENCE: 348
caaatgaggg aatgctcctg                                          20

<210> SEQ ID NO 349
<211> LENGTH: 240
<212> TYPE: DNA
<213> ORGANISM: Homo sapiens

<400> SEQUENCE: 349
ggaactgcag gagatccctg ctgccttcca gttcatggga tgatggcctc cacttctgcc    60
cctgtttgct tctcctttca aatcttacat gaaggtatac agtttgaaga agccagtttg   120
actccaatat ctgtgcaatg gaatactgct cattaaaaag gaattaaact attgatacac   180
acaacatggg tgaagatcaa actgtctcct tcccctttgat tcaagggaat ctgagaaatg   240

<210> SEQ ID NO 350
<211> LENGTH: 19
<212> TYPE: DNA
<213> ORGANISM: Homo sapiens

<400> SEQUENCE: 350
acttctgccc ctgtttgct                                           19

<210> SEQ ID NO 351
<211> LENGTH: 21
<212> TYPE: DNA
<213> ORGANISM: Homo sapiens

<400> SEQUENCE: 351
tgatcttcac ccatgttgtg t                                        21

<210> SEQ ID NO 352
<211> LENGTH: 187
<212> TYPE: DNA
<213> ORGANISM: Homo sapiens

<400> SEQUENCE: 352
tggagaaagt tgttgcaaac tgcccagaga ccctgggagt cactccagtt ttctgaaacc    60
cagatatttc agtgcctcag gagagacaag tcctgacctt ctctcctcca gctctcccag   120
gagataggca agcccctaac tccctaacta agcccttcag acctgaaatc cattgagtgg   180
cttctttt                                                      187

<210> SEQ ID NO 353
<211> LENGTH: 18
<212> TYPE: DNA
<213> ORGANISM: Homo sapiens

<400> SEQUENCE: 353
gcaaactgcc cagagacc                                            18

<210> SEQ ID NO 354
<211> LENGTH: 20
<212> TYPE: DNA
<213> ORGANISM: Homo sapiens

<400> SEQUENCE: 354
ttagggagtt aggggcttgc                                          20

```
<210> SEQ ID NO 355
<211> LENGTH: 184
<212> TYPE: DNA
<213> ORGANISM: Homo sapiens

<400> SEQUENCE: 355
agggccatgg gatgatgcag gtggagactg gagtgctaca gctgcaagca aatacatttc      60
tgtgctgtga agccacccat ttggtggtac tacgttaaaa cagctctagg aaattaatac     120
agatgttgcc tgtatttttg tttctcatat tactactcat tgttttaatg atgactgttt     180
tatt                                                                  184

<210> SEQ ID NO 356
<211> LENGTH: 20
<212> TYPE: DNA
<213> ORGANISM: Homo sapiens

<400> SEQUENCE: 356
aggtggagac tggagtgcta                                                  20

<210> SEQ ID NO 357
<211> LENGTH: 22
<212> TYPE: DNA
<213> ORGANISM: Homo sapiens

<400> SEQUENCE: 357
agaaacaaaa atacaggcaa ca                                               22
```

DETECTING GENETIC ABNORMALITIES

CROSS REFERENCE TO RELATED APPLICATIONS

This application is a continuation of U.S. patent application Ser. No. 12/581,083, filed Oct. 16, 2009, now abandoned, which claims the benefit of priority to U.S. Patent Application No. 61/106,435, filed Oct. 17, 2008, and which is a continuation-in-part of U.S. patent application Ser. No. 11/713,069, filed Feb. 28, 2007, now U.S. Pat. No. 7,799,531, which claims priority to U.S. Patent Application No. 60/777,865, filed Feb. 28, 2006, each of which is hereby incorporated by reference in its entirety.

BACKGROUND OF THE INVENTION

A majority of pregnant women receive some kind of test, including maternal serum screening and/or an ultrasound test, to determine risks for common birth defects, such as those resulting from trisomy 13, 18, and 21 (Down Syndrome). Both the sensitivity and specificity of these common non-invasive screening tools are extremely poor. The best current non-invasive tests lead to a false positive rate between 7 and 20%. This high false positive rate often causes individuals to opt for invasive diagnostic tests, such as chorionic villus sampling (CVS) and amniocentesis. Such invasive tests each carry a fetal loss rate of 0.5%-1% and account for the loss of thousands of normal fetuses annually. However, prenatal diagnosis can be critical for management of a pregnancy with chromosomal abnormalities and localized genetic abnormalities, because an accurate and early diagnosis allows for interventional care before or during delivery and can prevent devastating consequences for the neonate. The development of a non-invasive test for genetic abnormalities that is sensitive and specific with low false-positive and false-negative rates would be of benefit to the field of molecular diagnostics.

SUMMARY OF THE INVENTION

Accordingly, the present invention provides methods and compositions for detecting genetic abnormalities.

In one aspect, the present invention provides method for determining whether a fetus has at least one chromosomal abnormality. This method includes the step of comparing at least three alleles, and this comparing identifies the at least one chromosomal abnormality.

In a further aspect, the present invention provides a method for determining whether a fetus has at least one chromosomal abnormality. This method includes the steps of: (i) detecting a paternally-inherited fetal allele in a sample that includes both maternal and fetal nucleic acids, wherein that paternally-inherited fetal allele is not present in the maternal genome; (ii) detecting a first maternal allele and a second maternal allele in the sample; and (iii) comparing the paternally-inherited fetal allele to the first and second maternal alleles, where the comparing identifies the at least one chromosomal abnormality.

In an exemplary embodiment, comparing alleles according to the present invention includes detecting the number of molecules of each allele. In a further embodiment, detecting the number of molecules of each allele provides the allelic dosage of each allele.

In a still further exemplary embodiment, comparing alleles according to the present invention includes calculating a haplotype ratio. In a still further embodiment, the haplotype ratio is calculated according to the formula: HR=[P1−P2]/P3, where P1 is the number of molecules of a first maternal allele, P2 is the number of molecules of a second maternal allele, and P3 is the number of molecules of a paternally-inherited fetal allele.

BRIEF DESCRIPTION OF THE DRAWINGS

FIG. 4 is a schematic illustration of an embodiment of an assay of the invention.

FIG. 5A-B is a table of an exemplary list of tandem SNPs of the invention.

FIG. 6A-AAE is a table of an exemplary list of 118 human DNA sequences (SEQ ID NOS:1, 4, 7, 10, 13, 16, 19, 22, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 212, 131,134, 137, 140, 143, 146, 149, 152, 155, 346, 158, 161, 349, 164, 167, 170, 173, 176, 352, 179, 182, 185, 188, 191, 194, 197, 200, 203, 206, 355, 209, 214, 217, 220, 223, 226, 229, 232, 235, 238, 241, 244, 247, 250, 253, 256, 259, 262, 265, 268, 271, 274, 277, 280, 283, 286, 289, 292, 295, 298, 301, 304, 307, 310, 313, 316, 319, 322, 325, 328, 331, 334, 337, 340 and 343, respectively) which contain tandem SNPs of the invention, where for each of the 118 sequences, the given sequence is provided together with its sequence identification number, and a pair of "left" and "right" primers directed to those the given sequence which contains the tandem SNP, tandem SNPs and a representation of the given sequence underscored with ">" and "<" symbols to indicate locations in the given sequence where the left and right primers are complementary to the given sequence or to the complement of the given sequence.

FIG. 9A-C is a table of an exemplary list of tandem SNPs of the invention.

DETAILED DESCRIPTION OF THE INVENTION

Figure 1:
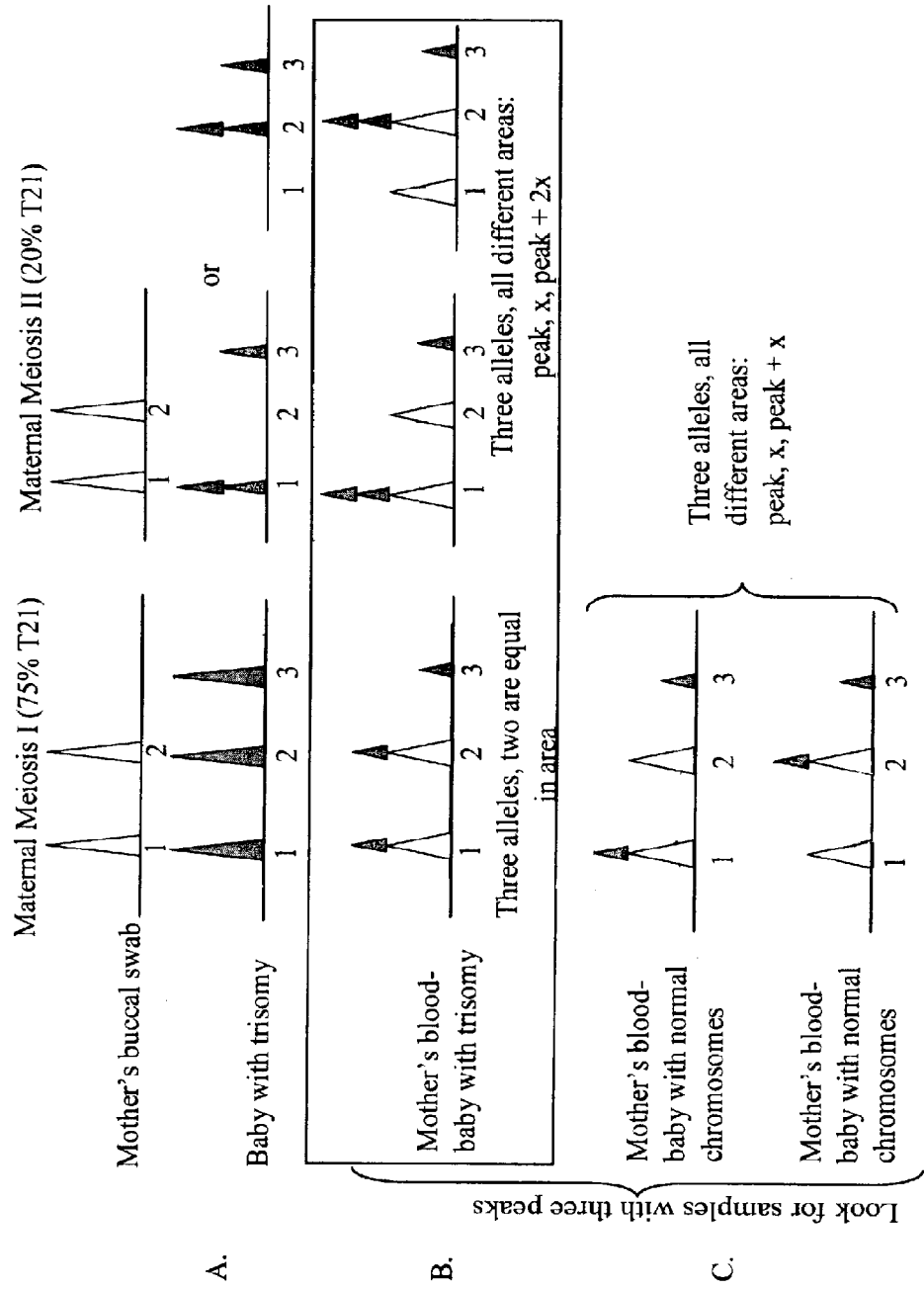
FIG. 1 is a schematic illustration of an embodiment of an assay of the invention.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* 3$^{rd}$ Ed., W. H. Freeman Pub., New York, N.Y. and Berg et al. (2002)

*Biochemistry*, 5$^{th}$ Ed., W. H. Freeman Pub., New York, N.Y., all of which are herein incorporated in their entirety by reference for all purposes.

Note that as used herein and in the appended claims, the singular forms "a," "an," and the include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

I. Overview of the Invention

The present invention is directed to methods and compositions for detecting genetic abnormalities. By "genetic abnormality" is meant any variation in one or more elements of an individual's genome in comparison to a general population. Genetic abnormalities can include without limitation chromosomal abnormalities, single point mutations, and any other variations that can result in changes in the levels of cDNA, RNA, mRNA, microRNA, and coding and non-coding RNA. Thus, the term "genetic abnormality" as used herein is interchangeable with the term "nucleic acid abnormality". "Chromosomal abnormalities" can include without limitation aneuploidy (including without limitation trisomy 13 (Patau Syndrome), trisomy 18 (Edward Syndrome) and sex chromosome aneuploidies such as XXY (Klinefelter's Syndrome), subchromosomal abnormalities, gross deletions, gross insertions, large deletions, large insertions, copy number variants, copy number variation, repeat variations, structural alterations, small deletions (<20 bp), small insertions (<20 bp), indels, small indels (<20 bp), and the like. Genetic abnormalities can be inherited, arise somatically, occur as de novo events, occur clonally, etc.

In general, methods and compositions of the present invention can be used to analyze a sample comprising genetic material from two or more individuals. "Genetic material" includes without limitation DNA (including full or partial chromosomes, cDNA and genetic DNA) and RNA (including mRNA, tRNA, siRNA, micro RNA, coding and non-coding RNA). Methods of the present invention include comparing alleles contained in the sample to detect and quantify differences between the genetic material from the two or more individuals. In some embodiments, such differences can be used to identify genetic abnormalities in one or more of the individuals. Although the description of the present invention is primarily provided herein in terms of DNA, it will be appreciated that these aspects and embodiments of the invention also encompass RNA, and that all methods and compositions of the present invention can be applied to any nucleic acid.

In a specific aspect, methods and compositions of the invention are used to analyze a sample containing fetal and maternal genetic material. In a further aspect, methods and compositions of the invention are used to compare alleles contained in such a sample to determine if the fetal genetic material comprises a genetic abnormality. As used herein, "allele" is a variant form of a sequence at a particular region on a chromosome. The variants in the sequence can come as a result of single nucleotide polymorphisms ("SNPs"), combinations of SNPs, haplotype methylation patterns, insertions, deletions, and the like. An allele may comprise the variant form of a single nucleotide, a variant form of a contiguous sequence of nucleotides from a region of interest on a chromosome, or a variant form of multiple single nucleotides (not necessarily all contiguous) from a region of interest on a chromosome.

The term "comparing alleles" as used herein refers to any analysis that identifies similarities and differences among the alleles of interest. For example, comparing alleles may involve detecting and/or identifying the different alleles of interest in a sample. Comparing alleles may also involve detecting and quantifying the number of molecules of each of the different alleles of interest in a sample. Comparing alleles may further involve determining the relative number of molecules of each of the different alleles with respect to each other or with respect to a reference sample. In addition, comparing alleles may involve a comparison of the concentrations or relative concentrations of each of the alleles in a sample. As will be discussed in further detail herein, comparing alleles in a sample can detect and identify genetic abnormalities.

Although the present invention is primarily discussed in terms of a comparison between fetal and maternal genetic material, the methods and compositions described herein can also be applied to other applications in which a comparison of the genetic material between two or more individuals is desired. Embodiments of such extensions to the described methods and compositions are discussed in further detail herein and are encompassed by the present invention.

II. Comparing and Quantifying Alleles

In one aspect, the present invention provides methods and compositions for comparing alleles in a sample.

A "sample" in accordance with the present invention may comprise any number of substances, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (i.e. in the case of nucleic acids, the sample may be the products of an amplification reaction, including both target and signal amplification as is generally described in PCT/US99/01705, such as PCR amplification reaction); purified samples, such as purified genomic DNA, RNA, proteins, etc.; raw samples (bacteria, virus, genomic DNA, etc.); as will be appreciated by those in the art, virtually any experimental manipulation may have been conducted on the sample.

In one aspect, samples of use in the present invention are obtained from a pregnant female. Such samples can include without limitation maternal blood, maternal urine, maternal sweat, maternal cells, or cell free DNA. In a further aspect, these maternal samples contain both maternal and fetal DNA.

Although the majority of the disclosure herein is directed to embodiments using DNA, it will be appreciated that any genetic material is contemplated for use and analysis in accordance with the present invention and is therefore encompassed by the present invention. In addition, the terms "chromosomal region" and "chromosome" are used interchangeably herein, and both refer to part or all of a chromosome unless otherwise specified.

In general, the present invention provides methods and compositions for comparing alleles in a sample. Comparing alleles in accordance with the invention includes detecting the identity of the different alleles present in the sample. Comparing alleles also includes detecting and/or quantifying the number of molecules of each allele of interest that is present in a sample. For example, a maternal sample containing both fetal and maternal DNA may contain three different alleles for a particular chromosomal region of interest. As discussed above, these three alleles would be variant sequences of the chromosomal region of interest. Methods known in the art and described further herein can be used to determine how many molecules of each of the three different alleles are present in the sample. In such an exemplary embodiment, comparing the three alleles would include comparing the number of molecules of each of the three alleles. Comparing alleles in further embodiments of the invention can include without limitation evaluating the concentration of alleles in a sample and evaluating relative concentrations and/or relative numbers of molecules of alleles in a sample.

In a further embodiment, evaluating relative concentrations or numbers of molecules in a sample includes calculating an "allelic ratio" among the alleles in a sample. This allelic ratio is the ratio of the amount of molecules of each of the alleles of interest present in the sample, and may be calculated in any number of ways known in the art and described further herein. For example, if a sample comprises two alleles A and B, and a standard method in the art (such as sequencing) shows that there are twice as many molecules of B as there are of A, then one embodiment of an allelic ratio may be the characterization of A:B as 1:2. In further embodiments, such as those containing a calculation of multiple alleles, the allelic ratio may be a standard ratio—for example, for three alleles A, B, and C, the allelic ratio may be expressed as the number of molecules of A:B:C. In further embodiments, a more complex relationship may be described as an allelic ratio, such as (A−B)/C. Such embodiments are discussed in further detail herein.

Methods for detecting and quantifying alleles or any other sequence of interest are known in the art. Such methods include without limitation any methods that detect DNA (including without limitation genomic and cDNA) and RNA (including without limitation mRNA, microRNA, and silent RNA). Such methods for detecting nucleic acids can include without limitation sequencing methods, gel electrophoresis, mass spectrometry, detection of methylation patterns, PCR methods, high performance liquid chromatography (HPLC) and the like. Methods for detecting and quantifying alleles in accordance with the present invention provide the sequence of the alleles present in the sample (or identify the presence of an allele of interest) and may also provide the number of molecules of each of the alleles in the sample. Methods for detecting and/or quantifying alleles that are of use in the present invention also include methods that quantify the relative amounts of two or more alleles of interest in a sample. By "relative amounts" is meant relative numbers of molecules and/or relative concentrations.

Sequencing methods of use for detecting and quantifying alleles of interest according to the present invention include without limitation single molecule sequencing, sequencing by synthesis, sequencing using arrays (hybridization and/or ligation), capillary sequencers, Sanger sequencing, constant denaturant capillary electrophoresis (CDCE), cycling temperature capillary electrophoresis (CTCE), polony sequencing, pyrosequencing, shot-gun sequencing, and the like. Commercial high throughput sequencing platforms for detecting and quantifying alleles of interest and such platforms are known in the art and can include without limitation: Illumina's GA, Life Technologies' SOLiD, Roche's 454, Pacific Biosciences single molecule sequencing platform, Oxford Nanopore, Ion Torrent, Complete Genomics, Nimblegen, Helicos Biosciences, Lingvitae, Nabsys, and Visigen Biotechnologies.

PCR methods of use for detecting and quantifying alleles of interest according to the present invention include without limitation digital PCR and competitive PCR.

Methods such as those described above and known in the art can be used to compare alleles in a sample by providing information on the identity (i.e., the sequence) of the alleles as well as the number of molecules of each allele present in the sample.

In general, methods of the invention include detecting alleles of a specific chromosomal region. As has been discussed above, the term "chromosomal region" refers to all or part of a chromosome. Detection of such alleles can be conducted using any method known in the art, including the sequencing and PCR methods described above. In some embodiments, the sample being analyzed is from a pregnant female and contains both maternal and fetal DNA. Detecting and/or quantifying the number of different alleles in the sample and the number of molecules of those alleles that are present in the sample can identify the presence of a chromosomal abnormality in a fetus.

In a further exemplary embodiment, a sample contains three alleles of a chromosomal region that is being analyzed. Two of the alleles are from a known source, while the third allele is expected to come from a separate source. Quantification of the number of molecules present in the sample of each allele allows comparison between the alleles from the known source and the third allele.

In a still further exemplary embodiment, the sample is a maternal sample containing both fetal and maternal nucleic acids. In this example, the sample again contains three alleles of a particular chromosomal region. If the maternal genome is heterozygous for this allele, then two of the three alleles detected in the sample are from the maternal germline DNA, while the third allele is expected from the paternal DNA contribution (if the paternal DNA contains an allele not present in the maternal genome). Quantification of the three alleles therefore allows comparisons between the two maternal alleles from the mother, allowing the determination of which allele and how many molecules were contributed by the mother to the fetus. Quantifying the number of molecules of the alleles also provides information on how many molecules of the third allele were contributed by the father to the fetus. Comparison of the maternally inherited and paternally inherited alleles further allows a quantification of the maternal and paternal contributions to the fetal DNA.

FIG. 1 is a schematic representation of the comparisons that can be made between different alleles detected in a sample. In FIG. 1, a maternal sample in which three alleles are detected is shown. The peaks illustrated in FIG. 1 represent the number of molecules of each allele present in the sample. As discussed herein, these "peaks" (i.e., the number of molecules) can be determined using methods well known in the art and described herein. For example, the area under the peaks from an electropherogram from a CDCE analysis of a sample provides information on the number of molecules of each detected allele. Similarly, the output of a sequencing platform will provide a count of the number of molecules for each allele, which can also be depicted by the peaks in FIG. 1.

In an exemplary embodiment, genetic abnormalities, including chromosomal abnormalities, are detected by comparing the number of molecules of alleles in a sample. As is generally illustrated in FIG. 1, a sample comprising both fetal and maternal nucleic acids will be expected to show specific relationships between the number of molecules for alleles of a particular chromosome. For example, if the maternal genome is heterozygous for a particular chromosomal region, then two alleles detected in the sample will be the maternal contribution. Since the sample contains both fetal and maternal DNA, the number of molecules detected for those two alleles will include the numbers of molecules from the maternal DNA and the numbers of molecules for the maternally-inherited allele in the fetal DNA (also referred to herein as the "maternally-inherited fetal allele"). The fetal genome will contain maternally and paternally-inherited alleles. If the paternally-inherited allele in the fetal DNA (also referred to herein as the "paternally-inherited fetal allele") is not present in the maternal genome, then three different alleles will be detected in the sample containing both maternal and fetal DNA (the two alleles from the mother and the one paternally-inherited allele in the fetus). Comparing the number of molecules for each allele can then be used to detect a chromosomal abnormality.

In further embodiments, the present invention provides methods for detecting genetic abnormalities, including chromosomal abnormalities, in a fetus by detecting alleles for a location of interest on a chromosome (also referred to herein as a "genetic location"), where the maternal genome is heterozygous at that location of interest and the fetus inherits a different allele from the father at that same genetic location. In still further embodiments, methods of the invention detect a paternally-inherited fetal allele in a sample comprising both maternal and fetal nucleic acids, where that paternally-inherited fetal allele is not present in the maternal genome. Detection of such a paternally-inherited fetal allele will in such embodiments indicate that the fetus does have a genetic abnormality.

As will be appreciated, the term "maternal allele" may refer to the allele inherited by the fetus from the mother and/or the alleles in the maternal genome. In a sample comprising both fetal and maternal DNA, the molecules of "maternal allele" detected and quantified will include both molecules of the allele from the maternal DNA as well as molecules from the fetal DNA of the maternally-inherited fetal allele.

For example, in approximately 95% of trisomy cases, the fetus inherits two copies of the chromosome from the mother. In this situation, three alleles of that chromosome or a particular region of that chromosome are detected in the sample (represented by the three peaks in FIG. 1). As discussed above, if the mother is heterozygous, two of the alleles detected are the maternal alleles. The number of molecules detected for those two alleles will reflect the molecules from the maternal DNA in the sample plus the molecules of those same two alleles from the fetal DNA (i.e., the maternal alleles plus the maternally-inherited fetal alleles). The third allele detected will be the fetal allele that is paternally inherited and is not present in the maternal genome. In this example, trisomy is detected if the number of molecules for the two maternal alleles is equal (first trace of FIG. 1B) or if all three alleles are present in different numbers in the relationship of peak, x and peak+2x, where "peak" represents the number of molecules for one of the maternal alleles, "x" represents the number of molecules for the paternally-inherited fetal allele, and "peak+2x" is the number of molecules for the other maternal allele (right two traces of FIG. 1B). In the situation in which the two maternal alleles have equal numbers of molecules, trisomy is detected, because the numbers for the two maternal alleles are actually a sum of the maternal alleles and the maternally-inherited fetal alleles. The only way for the numbers for both maternal alleles to be equal in a sample comprising both fetal and maternal DNA is if the fetus inherited two alleles from the mother. The presence of the paternally inherited allele indicates that the fetus must then have trisomy, because it has both alleles from the mother and one from the father.

Similarly, in the situation in which all three alleles are present in the sample in the relationship of peak, x and peak+2x, this also indicates that the fetus has trisomy. The "peak" represents the number of molecules of maternal allele. "x" represents the number of molecules of the paternally-inherited fetal allele. "x" therefore represents a kind of internal standard of how much fetal DNA is present in the sample. The allele with the number of alleles "peak+2x" thus contains alleles from the mother as well as two copies of the allele from the fetus. These two copies are the maternally-inherited fetal DNA. Therefore, the fetus again has inherited two alleles from the mother and one from the father, which is an indication of trisomy.

The same analysis of the number and identity of the alleles in a sample can also be used to determine that the fetus does not have trisomy. As discussed above, this analysis must be conducted for an allele for which the maternal genome is heterozygous. If three alleles are detected in a sample containing both maternal and fetal DNA, then two of the alleles will be from the heterozygous mother, and the third allele is the paternally-inherited fetal allele. For a fetus without trisomy, the number of molecules of the three alleles will all be different, but unlike the case with trisomy above, the number of molecules of the three alleles will be in the relationship of "peak", "x" and "peak+x". "Peak" represents the number of molecules of one of the maternal alleles. "x" represents the number of molecules of the paternally-inherited fetal allele. "Peak+x" represents the number of molecules of the second maternal allele—this number includes both the number of molecules of the allele from the maternal DNA and the number of molecules of the maternally-inherited fetal allele. Thus, if the fetus has inherited only one chromosome from each parent, there should be a larger number of molecules for the allele the fetus inherited from the mother and a smaller number of molecules for the allele the fetus inherited from the father. Since the sample comprises maternal and fetal DNA but no paternal DNA, the only molecules of paternal alleles present in the sample are molecules of the paternally-inherited fetal allele. As a result, the number of molecules of the paternally-inherited fetal allele can provide an internal standard of how much fetal DNA is present in the sample relative to the maternal DNA.

In further embodiments, analysis of the number of molecules of alleles in a sample provides a measure of "allelic dosage". By "allelic dosage" as used herein is meant the number or concentration (or relative number or concentration) of molecules of each allele that is present in a sample. Thus, calculation of an "allelic ratio" as discussed above provides a mechanism to measure the dosage of each allele. Furthermore, in an analysis of a sample comprising both fetal and maternal nucleic acids, determining the number of molecules of paternally-inherited fetal alleles also provides a measure of the paternally-inherited fetal allelic dosage. This paternally-inherited fetal allelic dosage can serve as an internal standard that can be used to determine the maternally-inherited fetal allelic dosage. Thus, a calculation of allelic dosage provides a measure of the allelic dosage from each parent to the fetus. Calculations of allelic dosage can be used to detect a genetic abnormality using any of the methods described herein, because the relationships expected for maternal and paternal (and maternally-inherited and paternally-inherited) are equivalent to the relationships described herein for comparing alleles.

As will be appreciated, the above methods can also be used to compare alleles based on de novo deletions, insertions, and the like. For example, in the case of 22q11.2 deletion syndrome (the most common human deletion syndrome, which is typically a 3 million basepair deletion), the deletion is a de novo event in 75% of the cases. If the de novo event is a maternally-derived deletion in the fetal genome, three alleles would again be detectable in a sample comprising both maternal and fetal DNA. However, the number of molecules of the three alleles will show a relationship in which two of the alleles are present in equal numbers and the third allele will be present in smaller numbers. In other words, two fetal alleles will not be detected in the sample, because one of those alleles would be deleted. As discussed above, for a normal fetus, all three alleles should have different numbers of molecules present in the sample, with the numbers being in the relationship of "peak", "x" and "peak+x". In the case of a maternally-derived deletion, the numbers would instead be in the relationship of "peak", "peak" and "x".

Similarly, in the case of a de novo but paternally-derived 22q11.2 deletion in the fetal genome, a third allele would not be detected in a sample containing both maternal and fetal DNA, because it would be the paternally-inherited fetal allele that would be deleted. In further embodiments, multiple assays directed to the detection of different alleles can be conducted to confirm that the lack of a third fetal allele is the result of a deletion rather than the result of a non-informative assay (i.e., an assay in which the maternal genome is not heterozygous for an allele or the paternal genome has an allele in common with the maternal genome).

In further embodiments, methods of the present invention can be used to detect alleles that are inherited. In the maternally-derived and paternally-derived deletions discussed above, the maternal and paternal genomes are normal at the deletion/insertion site, but during meiosis, deletions or insertions occur and are passed to the fetus. In contrast, deletions and insertions and point mutations (which would include basepair substitutions), small (less than 20 base pairs) deletions or insertions (also referred to herein as "small-deletions" and "small-insertions" respectively) may occur in the maternal and/or paternal genomes and are passed on to the fetus. When a target sequence is larger than the small deletion or insertion, the same comparisons described above for allelic comparisons can be used to determine allelic dosage inheritance if a neighboring SNP can be encompassed by the target sequence. For example, the delta F508 deletion in the CFTR gene is a small deletion that can be passed on to the fetus by either the mother or the father. In the case where the mother is a carrier of the delta F508 deletion, it will appear as if she has two peaks. If the father contributes a normal allele and the fetus inherits the delta F508 deletion, the maternal plasma would show two peaks of equal area and height. It would not be clear if there was no fetal DNA present in the sample, or was at levels too low to be detected. However, if a neighboring SNP is encompassed, permitting at least three possible alleles in the target sequence, it would be possible to distinguish maternally inherited from paternally inherited alleles. The term "peaks" as used herein refers to the number of molecules of an allele and to a signal associated with the number of molecules of an allele.

In one aspect, the present invention provides methods and compositions for comparing alleles, where those alleles may be comprised of haplotypes. As used herein, the term "haplotypes" refers to groups or sets of markers (including without limitation SNPs, deletions, small deletions, insertions, small insertions, methylation, and short tandem repeats) that are inherited together as a unit. Thus, alleles detected and quantified as described herein encompass multiple markers, and thus different alleles comprise different combinations of these multiple markers. As will be discussed in further detail herein, alleles of use in the present invention may comprise multiple SNPs. These SNPs may be contiguous or non-contiguous. In further embodiments, alleles for comparison may include any combination of sites, including deletion sites, insertion sites, and sites which comprise variant sequences of two or more nucleotides in length. For example, alleles detected and compared in accordance with the present invention may include a deletion site and/or an insertion site and/or one or more SNPs and/or a variant sequence comprising two or more nucleotides. Such combinations increase the number of haplotypes that can be detected for a particular genetic location, thus increasing the informative of the comparative assays of the invention, as is discussed in more detail herein.

In a further aspect, multiple alleles are detected in a single reaction or assay. Thus, by identifying one or more SNPs, methylation patterns, or any other combination of markers that can compose an allele as described above, detecting multiple alleles (e.g., detecting both maternal alleles and a paternally-inherited fetal allele) in a single reaction or assay preserves phase information on the chromosome.

II(A). Amplification of Nucleic Acids Prior to Detection

In order to increase the signal of alleles of interest for a specific chromosome or chromosomal region, the nucleic acids in a sample are in many embodiments amplified using methods known in the art. Such amplification methods include polymerase chain reaction (PCR), strand displacement amplification (SDA), multiple displacement amplification (MDA), rolling circle amplification (RCA), rolling circle amplification (RCR) and other amplification (including whole genome amplification) methodologies. In certain embodiments, the chromosomes are amplified using primers directed to desired regions. This amplification enriches the sample for the allelic sequences for those specific chromosomal regions, and then methods known in the art for detecting those sequences can be used to detect and quantify the different alleles present in the sample. In some embodiments all nucleic acids in the sample are amplified, and then alleles of interest are detected using methods known in the art and described herein. In some embodiments, alleles of interest are amplified using primers with sequences such as those listed in FIGS. 5 and 6 and then detected using methods well known in the art and described herein.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers. The terms "nucleic acid," "nucleic acid molecule," or "polynucleotide" are used interchangeably herein.

In some embodiments, High-Fidelity (Hi-Fi) PCR is used to amplify alleles of interest in a sample. High-Fidelity PCR is an amplification method resulting in an error rate (in per basepair doubling) equal to or better than standard PCR. For example, Taq polymerase, which is not a high fidelity polymerase, has an error rate of ~$10^{-4}$ per basepair doubling. In contrast, *Pyrococcus furiosus* (Pfu) is a high-fidelity polymerase, with a published error rate for Pfu is $1.3 \times 10^{-6}$ per basepair doubling (Cline et al, Nucleic Acids Res. 1996 Sep. 15; 24(18): 3546-3551). Examples of high-fidelity enzymes include Pfu and its derivations, or other enzymes with similar proofreading 3'→5' exonucleases. Mixed blends and fusions with enzymes with proof-reading capabilities can increase the fidelity of a polymerase. Use of such a high fidelity polymerase ensures that the alleles of interest are amplified efficiently and with minimal to no introduction of errors.

Methods for improving PCR fidelity and efficiency include, among others: A) using a high-fidelity polymerase enzyme; and B) the addition of chemical reagents (e.g., betaine) that can lower temperatures required during the PCR process. Lowering temperatures required during the PCR products can increase efficiency and prevent damage to the amplification products, because prolonged heating of DNA and nucleotides during PCR can lead to damaged products, such as deaminated cytosines (uracils) and thus lead to misincorporation errors and miscopying errors during PCR (Andre, Kim, Khrapko, Thilly. Genome Res. 1997 7: 843-852. Zheng, Khrapko, Cotler, Thilly, Copeland. Mutat Res. 2006 Jul. 25; 599(1-2):11-20).

In certain embodiments of the invention, amplification using HiFi-PCR, is performed with primers present in molar excess (e.g., $10^{12}$ copies/µl of primer vs $10^6$ or less of the template) so that it is more likely that primers will anneal with template DNA than with each other (see, e.g., Li-Sucholeiki X C, Thilly W G. Nucleic Acids Res. 2000 May 1; 28(9):E44; Thompson J R, Marcelino L, Polz M. Nucleic Acids Res. 2002 May 1; 30(9): 2083-2088.). This can significantly reduce the creation of heteroduplexes.

III. Tandem SNPs

In certain embodiments, comparisons of alleles as described above utilize alleles of tandem single nucleotide polymorphisms (referred to herein as "tandem SNPs"). A "single nucleotide polymorphism (SNP)" is a single basepair variation in a nucleic acid sequence. A "tandem SNP" is a variation in more than one nucleotide in a nucleic acid sequence, e.g. on a chromosome. In some embodiments, a tandem SNP is a pair of SNPs that are located in the nucleic acid sequence. In further embodiments, a tandem SNP comprises more than two SNPs. As will be appreciated, any number of SNPs can be contained in a tandem SNP, limited only by the total number of nucleotides present in the nucleic acid. In still further embodiments, a tandem SNP comprises from 2 to about 20 SNPs. In still further embodiments, a tandem SNP comprises from about 3 to about 19, about 4 to about 18, about 5 to about 17, about 6 to about 16, about 7 to about 15, about 8 to about 14, about 9 to about 13, and about 10 to about 12 SNPs. In yet further embodiments, a tandem SNP comprises between two SNPs and the maximum number of SNPS that can be assayed in a single reaction, which may depend on the detection platform (e.g., the read length of the sequencing technology). In still further embodiments, a tandem SNP comprises between two SNPs and the maximum number of SNPs contained within the segment of genetic material to be analyzed. For example, fetal DNA circulating in maternal serum is often fragmented and has a length of 200-400 bases—in such an exemplary embodiment, the number of SNPs contained in a tandem SNP would be limited by the maximum number of SNPs contained in that fragmented DNA.

As will be appreciated, the two or more single SNPs in a tandem SNP may be of any distance apart. For tandem SNPs with more than two single SNPs, the multiple SNPs may be of equal distance apart, or there may be varying distances between them. In some embodiments, the distance between SNPs of a tandem SNP is generally about 350 basepairs or fewer. In still further embodiments, the SNPs of tandem SNPs are about 5 to about 300, about 10 to about 250, about 15 to about 200, about 20 to about 150, about 25 to about 140, about 30 to about 130, about 35 to about 120, about 40 to about 110, about 45 to about 100, about 50 to about 90, about 55 to about 80, and about 60 to about 70 base pairs apart.

Increasing the number of SNPs that make up tandem SNPs of the invention increases the potential number of haplotypes, and thereby increases the likelihood that an assay detecting alleles will be informative. For example, if a tandem SNP contains 3 SNP sites, the potential number of haplotypes is 8 and if it contains 4 SNP sites, the potential number of haplotypes is 16. This increases the likelihood that an assay will be informative, because the mother is more likely to be heterozygous at such a tandem SNP, and the paternal contribution to the fetus (also referred to herein as the "paternally-inherited fetal allele") is likely to be different from that present in the mother's genome. Thus, an assay that detects the alleles for this tandem SNP is likely to provide the at least three alleles that allows a comparison to be conducted for detection of a genetic abnormality, as is discussed in further detail herein.

Tandem SNPs provide a particularly powerful tool for comparing alleles in a sample, because tandem SNPs allow the detection and quantification of haplotypes. As will be discussed in further detail herein, the use of haplotypes in methods of the present invention provide an internal standard that eliminates the need for using reference markers across different chromosomes, thereby increasing specificity and/or minimizing or eliminating false positives.

As discussed herein, "haplotypes" are groups or sets of markers (including without limitation SNPs, deletions, small deletions, insertions, small insertions, methylation, and short tandem repeats) that are inherited together as a unit. Different alleles of a tandem SNP are thus haplotypes, and haplotypes can be assigned to a chromosome (i.e., the maternally inherited or paternally inherited chromosome). Comparing alleles of a tandem SNP comprises far more information than is possible from comparing individual SNPs, because comparing alleles of a tandem SNP provides a comparison of haplotypes.

Figure 2:
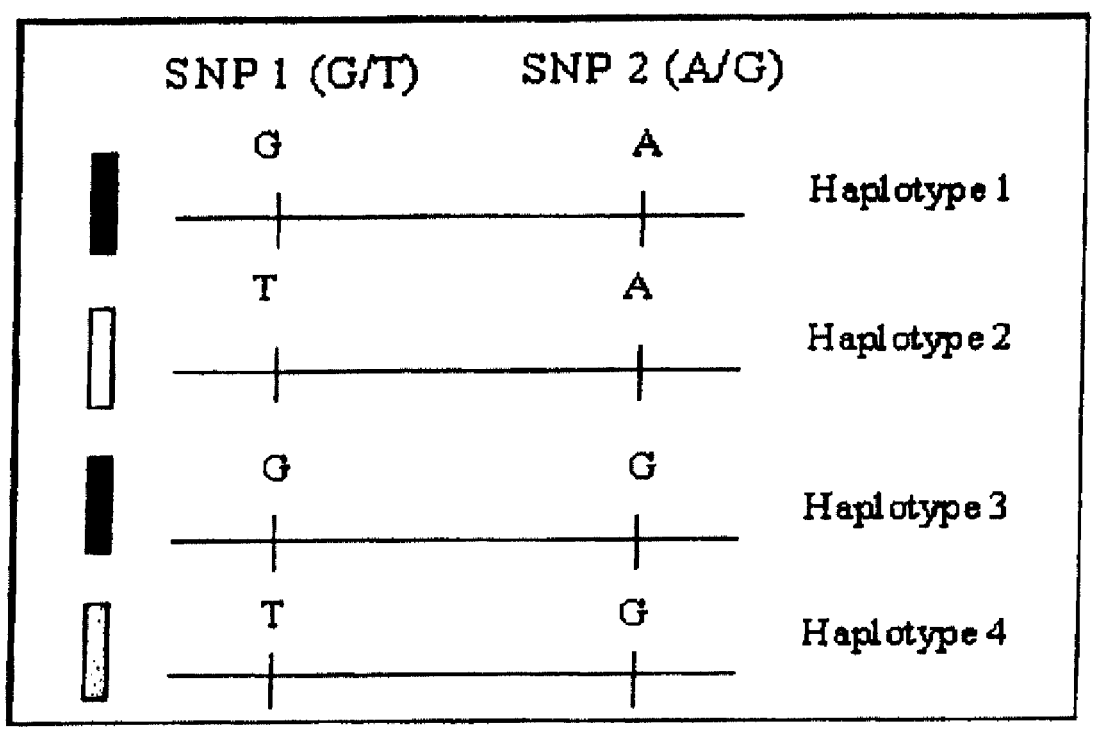
FIG. 2 is a schematic illustration of possible haplotypes in an exemplary embodiment of a tandem SNP.

An exemplary embodiment of a tandem SNP is schematically illustrated in FIG. 2. In this embodiment, the tandem SNP comprises a pair of SNPs. At SNP 1, two alleles are possible: G or T. At SNP 2, two alleles are possible: A or G. There are therefore four alleles possible for this tandem SNP, and these alleles are defined by the four possible haplotypes: G-A, T-A, G-G, or T-G. As will be appreciated, an individual may be heterozygous or homozygous for a tandem SNP, as is the case for a single SNP, but being heterozygous for a tandem SNP means that multiple different haplotypes are possible alleles for that tandem SNP. As will also be appreciated, for tandem SNPs containing three or more SNPs, the resultant number of possible haplotypes will also increase.

As discussed above, genetic abnormalities can be detected in a fetus by comparing the number of molecules of alleles between the fetal and maternal nucleic acids in a sample. By using tandem SNPs, the comparison can be used to both compare and quantify the differences between maternal and fetal DNA.

In an exemplary embodiment, detecting the alleles of tandem SNPs in a sample containing both maternal and fetal DNA can be used to calculate a haplotype ratio. As discussed above, these allele comparison assays are conducted for chromosomal regions of interest at which the maternal genome is heterozygous. In the case of tandem SNPs, the maternal genome being heterozygous means that it has two different haplotypes for that particular tandem SNP. Detecting the number of molecules of alleles of the tandem SNP present in a sample is thus a detection of the number of molecules of the different haplotypes are present in the sample.

If three alleles of a tandem SNP are detected in a sample containing both maternal and fetal DNA, the haplotype ratio (HR) can be calculated using the following formula:

$$HR = [P1-P2]/P3 \quad \text{(Formula I)}$$

P1 and P2 represent the number of molecules of each of the maternal haplotypes, and P3 represents the number of molecules of a third haplotype that is not present in the maternal genome. P3 thus represents the number of molecules of the haplotype inherited by the fetus from the father. As discussed herein for comparing alleles, the calculation of the haplotype ratio provides a way to determine if the fetus has a chromosomal abnormality, including without limitation trisomy, monosomy, partial duplication, partial deletion, microduplication, microdeletion, and the like. As will be appreciated, the description of the number of molecules of alleles as relating to the terms "peak", and "x" are related to P1, P2 and P3 of Formula 1. For example, P1 and P2 represent the maternal alleles—i.e., "peak+x" (or "peak+2x" in cases of trisomy) and "peak", whereas P3 of Formula 1 is equivalent to the paternally-inherited fetal allele, i.e., "x".

In exemplary embodiments, the haplotype ratio calculation will produce the discrete results of 1, 2, 0 or 0.5. These numbers are interpreted as follows:

TABLE 1 interpretation of haplotype ratio calculations for the detection of trisomy and/or partial duplications

| Haplotype ratio | Interpretation |
| --- | --- |
| |P1 − P2|/P3 = 1 | Fetus has the normal number of chromosomes |
| |P1 − P2|/P3 = 2 | Fetus has trisomy, likely as result of a duplication during maternal meiosis II or paternal meiosis I |
| |P1 − P2|/P3 = 0 | Fetus has trisomy, likely as a result of a duplication during maternal meiosis I |
| |P1 − P2|/P3 = 0.5 | Fetus has trisomy, likely as a result of a duplication during paternal meiosis II |

In a further embodiment, paternal non-disjunction, in which the fetus inherits two alleles from the father, may result in the haplotype ratios described in Table 1. In addition, if the two alleles from the father are both not found in the maternal genome, it would be possible to detect four alleles in a sample containing both maternal and fetal DNA—two alleles would again be from the maternal genome, and two would be paternally-inherited fetal alleles (see FIG. 3, lower panel for exemplary combinations of alleles).

In further embodiments, the haplotype ratio can be calculated according to the following formula:

$$HR = [P1-P2]/[P3+P4] \quad \text{(Formula II)}$$

In this embodiment, P1 and P2 represent the number of molecules of each of the maternal haplotypes and P3 and P4 represent the number of molecules of a third and fourth haplotype that is not present in the maternal genome. As will be appreciated, Formula II is applicable to embodiments of paternal non-disjunction trisomy, in which two paternally-inherited fetal alleles are present in the sample. Formula II is also applicable to situations in which only one paternally-inherited fetal allele is present in the sample—in such situations, either P3 or P4=0. Thus, Formula II can be applied to calculate the haplotype ratio for any sample from a pregnant female carrying a single fetus.

For de novo deletions in the fetus (including partial deletions, microsomal deletions, large deletions, etc.), paternally inherited deletions in the fetus would result in an entire panel of tandem SNPs without an informative third allele being present in the maternal sample. In such a situation, haplotype ratios cannot be calculated. Thus, the absence of an informative third allele or third haplotype can indicate a de novo deletion in the paternally inherited chromosome and would be informative in and of itself.

Thus, calculation of the haplotype ratio provides discrete detection and quantification of fetal chromosomal/genetic abnormality/allelic dosage within a single measurement from a sample comprising both maternal and fetal DNA. Unlike traditional methods of using single SNPs to determine whether a fetus has a chromosomal abnormality, the present invention does not require measurements of alleles across different chromosomes in order to determine the amount of fetal DNA present in the sample in relation to the maternal DNA. As discussed above, the present invention has an internal standard for each measurement. Since the maternal genome is heterozygous for the particular tandem SNP being analyzed, detection of three alleles in a sample containing both maternal and fetal DNA means that one of the detected alleles is the paternally-inherited fetal allele. Since the molecules of the paternally-inherited fetal allele can only be from the fetal DNA, detection of the number of molecules of that paternally-inherited fetal allele provides a measurement of how much fetal DNA is present in the sample. This third allele serves as an internal standard of the amount of fetal DNA, and there is no need to compare the measurement of the number of molecules of fetal alleles against the number of molecules of fetal alleles present for another chromosome that is not expected to have an abnormality. Thus, in the present invention, a single measurement of the number of molecules of an allele of a particular chromosome (i.e., a chromosome expected to be subject to an abnormality) provides all the information needed to determine whether the fetus has a chromosomal abnormality.

A further advantage of the methods of the present invention, particularly the internal standard provided by detection of the third allele, is that the ratios of the alleles and the calculation of the haplotype ratio will not vary based on the concentration in the sample of fetal genetic material. Traditional methods for detecting chromosomal abnormalities must normalize calculations of ratios with respect to the amount of fetal genetic material present in the sample being analyzed. In contrast, the methods of the present invention do not require such normalization, because comparing the number of molecules of the paternally-inherited fetal allele to the number of molecules of the maternal alleles in accordance with the present invention allows a calculation of allelic ratios that is independent of the amount of the total amount of fetal genetic material present in the sample.

As will be appreciated, the above methods for calculating haplotype ratios can be conducted using a single tandem SNP or using multiple tandem SNPs (also referred to herein as "panels" of tandem SNPs). When multiple tandem SNPs are used in any methods in accordance with the present invention, they can be utilized one at a time, in specific groupings, or all possible tandem SNPs can be analyzed at the same time in a multiplex assay. In some embodiments of the invention, panels of tandem SNPs comprise between 2 and 200 tandem SNPs. As will be appreciated, each of these tandem SNPs define a haplotype and therefore may in turn comprise two or more SNPs. In further embodiments, panels of tandem SNPs comprising between about 2-150, 10-140, 15-130, 20-120, 25-110, 30-100, 35-90, 40-80, 45-70, and 50-60 tandem SNPs are used in accordance with the present invention.

Multiple tandem SNPs may be assayed individually for a sample or multiplexed into a single assay. In some embodiments, the number of SNPs applied in a single assay may depend on the amount of nucleic acids that are present in and/or can be obtained from a sample. In further embodiments, all or a selected portion of the nucleic acids in a sample are amplified, which will allow multiple tandem SNPs directed to one or more chromosomes to be applied in a single multiplexed assay. As will be appreciated, using multiple tandem SNPs, either sequentially or simultaneously, can be used in some embodiments to assay for abnormalities in multiple chromosomes. The number of chromosomes that can be assayed using methods of the invention is limited only by the number of chromosomes present in the organism from which the sample is obtained.

In many embodiments, a panel of tandem SNPs is assayed in a sample, but only a subset of the panel (anywhere from between 1 and up to the total number of tandem SNPs in the panel) is informative, meaning that not every tandem SNP in a panel will produce a "positive" result. A positive result in assays utilizing tandem SNPs is generally the detection of at least three alleles for a particular tandem SNP. For any particular sample, even a single positive result from a tandem SNP can allow detection of a genetic abnormality. Results from more than one tandem SNP can be used as further internal confirmation of an assay.

The analysis of the paternally inherited fetal allele, particularly analysis with respect to tandem SNPs, is of use in detecting non-chromosomal mutations. In the case of a point mutation that is present in the mother or father's genome (A* in FIG. 4), this can be combined with a nearby SNP site to create at least three potential haplotypes. The inheritance pattern of the point mutation(s) to the fetus can therefore be traced in accordance with the methods described herein.

As is schematically illustrated in FIG. 4, the use of tandem SNPs allows detection of a recessive mutation that would not be detectable in methods utilizing single SNPs. As shown in the left panel, detecting alleles for a single SNP in a sample comprising both maternal and fetal DNA does not allow one to determine whether the fetus has inherited the point mutation. However, using the haplotype analysis possible by detecting alleles of tandem SNPs (FIG. 4, right panel), it is possible to detect the third allele in the sample, which is the paternally-inherited fetal allele. If the paternally-inherited fetal haplotype comprises the recessive point mutation, detection of that third allele is informative. Although in this exemplary embodiment the tandem SNP comprises two single SNPs, as is discussed herein, tandem SNPs may comprise multiple single SNPs.

In the extremely rare situation that the point mutation occurs at a base pair which is known to have a SNP, the single site would be tri-allelic and therefore it may not be necessary to combine the point mutation site with a nearby SNP. Then a simple comparison of detected alleles as described in further detail above would allow detection of the mutant allele.

The ability to trace the inheritance pattern of point mutations has clinical importance in the case of recessive disorders. If both the mother and father are heterozygous at a point mutation site carrying a normal and mutated base, the use of haplotypes (point mutation+nearby SNP) allows one to determine whether the fetus is at risk for being homozygous for the recessive mutation. This is thus one embodiment of the tandem SNP analysis described herein. The combination of any mutation (e.g. point mutation, insertion, deletion, methylation) along with a nearby SNP is useful to determining the fetal risk of homozygosity for a recessive disorder.

In some embodiments, short tandem repeats (STRs) can be used as a tandem SNP or as part of a tandem SNP for comparing alleles. STRs are highly polymorphic regions in the genome, and many alleles can be present at a single STR site—for example, in many situations it is possible to have ten or more alleles at a given site. STRs generally arise in highly repetitive sequences which are error prone during amplification, resulting in their highly polymorphic state.

In some embodiments, tandem SNPs do not comprise STRs.

In some embodiments, the information gathered about the alleles of interest in a sample comprising both maternal and fetal DNA is compared to similar information gathered about the alleles of interest in a sample comprising maternal DNA but no fetal DNA. The sample containing only the maternal DNA can be used as a reference for the sample containing both maternal and fetal DNA. Although such a reference sample is not generally necessary, it can provide additional substantiation of the results from the assays discussed herein. In some embodiments, the sample comprising maternal DNA but no fetal DNA is obtained using methods known in the art. Such samples can be obtained from a number of sources, including without limitation: maternal buccal swabs, maternal cells, including maternal white blood cells, and the like.

III(A). Identifying Tandem SNPs

As will be appreciated, different samples will require the use of different tandem SNPs for detection of genetic abnormalities. This is because one requirement of the methods described herein, particularly methods involving tandem SNPs, is that the maternal genome must be heterozygous for the allele of interest in order to allow the detection of a third, paternally-inherited allele. In addition, tandem SNPs for which the paternal genome comprises the same haplotypes as the maternal genome will not be informative, because it is the detection of three alleles for a particular tandem SNP that provides the internal standard of the paternally-inherited fetal allele.

The present invention provides methods and compositions for identifying tandem SNPs. In some embodiments, a chromosomal region of interest is studied to identify potential markers (i.e., alleles) for use as tandem SNPs. Studying a chromosomal region of interest for identifying tandem SNPs in some embodiments involves analyzing a database comprising information on the occurrence of SNPs in one or more populations (such as the database from the International HapMap Project). In further embodiments, studying a chromosomal region of interest to identify tandem SNPs comprises collecting samples of nucleic acids for a number of individuals and amplifying the region of interest. The amplification product can then be sequenced or otherwise analyzed to identify potential markers for use as tandem SNPs.

In some embodiments, a tandem SNP is chosen by identifying two or more neighboring SNPs. Such SNPs may be separated by any range of distances, and as will be appreciated, the distances between neighboring SNPs is limited only by the size of the chromosomal region of interest. In some embodiments, the two or more SNPs in a tandem SNP may be separated by a distance of about 5 to about 400 base pairs. In further embodiments, the two or more SNPs in a tandem SNP may be separated by a distance of about 10 to about 350, about 20 to about 300, about 30 to about 250, about 40 to about 200, about 50 to about 150, about 50 to about 140, about 60 to about 130, about 70 to about 120, about 80 to about 110, and about 80 to about 100 base pairs. In embodiments in which more than two SNPs are in a tandem SNP, each individual SNP may be of equal distance from the other SNPs, or the SNPs may be at varying distances from each other. Although the description herein of tandem SNPs is primarily in terms of two or more SNPs, a tandem SNP may also include any combination of SNPs, deletions, insertions, and sequence variants of two nucleotides or greater, and descriptions of tandem SNPs herein applies to all such combinations. As will be appreciated, "neighboring" SNPs as described herein may have one or more SNPs (or deletions, insertions, sequence variants) that occur in the region between the SNPs that are part of a particular tandem SNP. Thus, in an exemplary embodiment, if SNPs A, B and C occur in that order along a chromosomal region in a population, a tandem SNP may be chosen such that A and C are the "neighboring" SNPs, and B is a SNP located in the intervening region between A and C.

In further embodiments, tandem SNPs of the invention are selected such that the combination of SNPs (and/or deletions, insertions and sequence variants) results in more than two haplotypes being present in a population. In still further embodiments, tandem SNPs are chosen that result in more than two haplotypes present in populations across different ethnic groups—as will be appreciated, such information can be generated from publicly available databases (such as the HapMap database) or from direct investigation of samples collected from multiple individuals.

In still further embodiments, tandem SNPs of the invention are chosen such that their component SNPs, deletions, insertions and sequence variants do not lie within a common, non-disease related CNV (copy number variation) region, such as those present in the Database of Genomic Variants from The Centre for Applied Genomics at http://projects.tcag.ca/variation/.)

In further embodiments, methods for identifying tandem SNPs utilize maternal buccal samples (or any other samples that contain maternal DNA but no fetal DNA) in order to identify regions at which the maternal genome is heterozygous.

In an exemplary embodiment, tandem SNPs are identified from population data files (such as the HapMap database). In this exemplary embodiment, highly heterozygous (i.e., greater than 10% or more or "common") SNPs are identified. In some embodiments, only those SNPs that are highly heterozygous in all populations contained in the database are chosen as likely candidates. In other embodiments, likely candidates are chosen from SNPs that are highly heterozygous in a subset of the populations contained in the database. Tandem SNPs can then be provisionally selected by choosing highly heterozygous SNPs that are at a desired distance from each other, as is discussed above. As is also discussed herein, likely tandem SNPs may comprise a wide range of individual SNPs.

In still further embodiment, any likely tandem SNPs that occur in the list of SNPs from common CNV regions are removed from further consideration. In still further embodiments, tandem SNPs that lie in regions with long stretches of homopolymeric sequences (i.e. 6 or greater) are also removed from further consideration.

In yet further embodiments, primers are designed to amplify regions containing likely tandem SNPs. In some embodiments, these primers are optimized for efficiency and specificity using methods known in the art. In further embodiments, primers are tested to determine if they preferentially amplify one or more alleles of the likely tandem SNPs over others.

As will be appreciated, tandem SNPs of use in accordance with the present invention can be chosen using any combination of the above methods and characteristics. In some exemplary embodiments, tandem SNPs are chosen based solely on distance between each component. A "component" of a tandem SNP as used herein refers to individual SNPs, deletions, insertions, or sequence variations that make up a tandem SNP.

In some embodiments, a chromosomal region of interest can be directly sequenced from one or more samples to identify potential tandem SNPs. In further embodiments, genetic material from a number of individuals, (e.g., 8 individuals, 10 individuals, 96 individuals, even 20,000 individuals) can be collected and amplified for a given target sequence of interest. The alleles present in this amplified sample can then be detected and quantified to identify sequences that can serve as tandem SNPs. In some embodiments, the genomic DNA from these individuals are pooled together and a target sequence of interest is amplified in a single PCR reaction. If three or more alleles occur in this pooled sample, and at least three of these alleles occur at high percentages (>10%) in the pooled sample, then the target sequence is a likely candidate for use as a tandem SNP in accordance with the present invention.

As will be appreciated, tandem SNPs can be identified for any chromosome. Exemplary tandem SNPs identified in accordance with the present invention for chromosome 21 are provided in FIG. 5. FIG. 6 shows tandem SNPs for chromosome 21 as well as primers that can be used for amplification and detection of these tandem SNPs. Exemplary tandem SNPs identified in accordance with the present invention for chromosomes 13, 18 and 22 are provided in FIG. 9. Tandem SNPs identified in accordance with the present invention for any other chromosome are also encompassed by the present invention, as are tandem SNPs other than those in FIGS. 5, 6 and 9. As will be appreciated, sequences that have at least 65%, 70%, 75%, 80%, 85%, 90%, 91%, 92%, 93%, 94%, 95%, 96%, 97%, 98%, and 99% sequence identity to the sequences provided in FIGS. 5-6 and 9 are also encompassed by the present invention.

IV. Uses Beyond Detecting Genetic Abnormalities

Although the above description has been provided in terms primarily of genetic abnormalities, the same detection and quantification of alleles, including alleles of tandem SNPs, can be used in other applications.

In some embodiments, the present methods and compositions of the present invention can be used to evaluate tissue rejection in a patient who has received a tissue transplant. In such embodiments, if the host is heterozygous, detection of a third (and possibly fourth) allele frequency may come from the graft at the time of transplant. The levels of allelic dosage at the time of transplant can then be compared to levels at later time points to determine if the graft is being rejected. Such comparisons can be conducted by calculating allelic and/or haplotype ratios as discussed herein. An advantage of using tandem SNPs in this embodiment, particularly with tandem SNPs comprising more than two SNPs or other components, is that the likelihood of having an informative assay (i.e., one in which at least three alleles can be detected) is increased, and it would be possible to quantitatively measure both the maternally inherited and the paternally inherited alleles from both the recipient and the graft by calculating a Haplotype Ratio. Such information can not be obtained from studies in which only individual SNPs are used to compare between the genetic material of the recipient and the graft.

In still further embodiments, the methods and compositions can be used in transfusions, to determine if a donor is a match for the recipient. As with the analysis for detecting tissue rejection, the allelic dosage can be calculated to determine if the transfusion is acceptable to the recipient.

In further embodiments, the methods and compositions of the present invention can be used in forensic analysis by identifying samples through a comparison of alleles for a particular chromosomal region. Methods of the present invention for detecting and comparing alleles, including alleles of tandem SNPs, will provide information as to whether a particular forensic sample comprises samples from one or more individuals. Such forensic analysis may be used in cases of sexual assault, for determining paternity, as well as other forensic applications that would benefit from the ability to compare allelic dosage in a sample.

EXAMPLES

Example 1

Tandem SNPs for Chromosome 21

Allelic markers on chromosome 21 were selected by examining tandem SNPs. These tandem SNPs covered both q and p arms of the chromosome. Using heterozygosity data available through dbSNP, DCC Genotype Database and through the HapMap Project, SNPs that appeared to be promising for high heterozygosity ($\geq 25\%$) were selected. Because all four possibilities may not exist in nature due to haplotype blocks in regions of low recombination, those that suggested less than three haplotypes were screened out.

Target sequences covering tandem SNPs were designed using Vector NTI and WinMelt software. As an example, the melting map of a CDCE or CTCE target covering two tandem SNPs (dbSNP rs2839416 and rs2839417) on chromosome 21 was calculated using WinMelt according to the algorithm of Lerman and Silverstein (Lerman et al., Methods Enzymol, 1987. 155: p. 482-501) and is depicted in FIG. 7.

Figure 7:
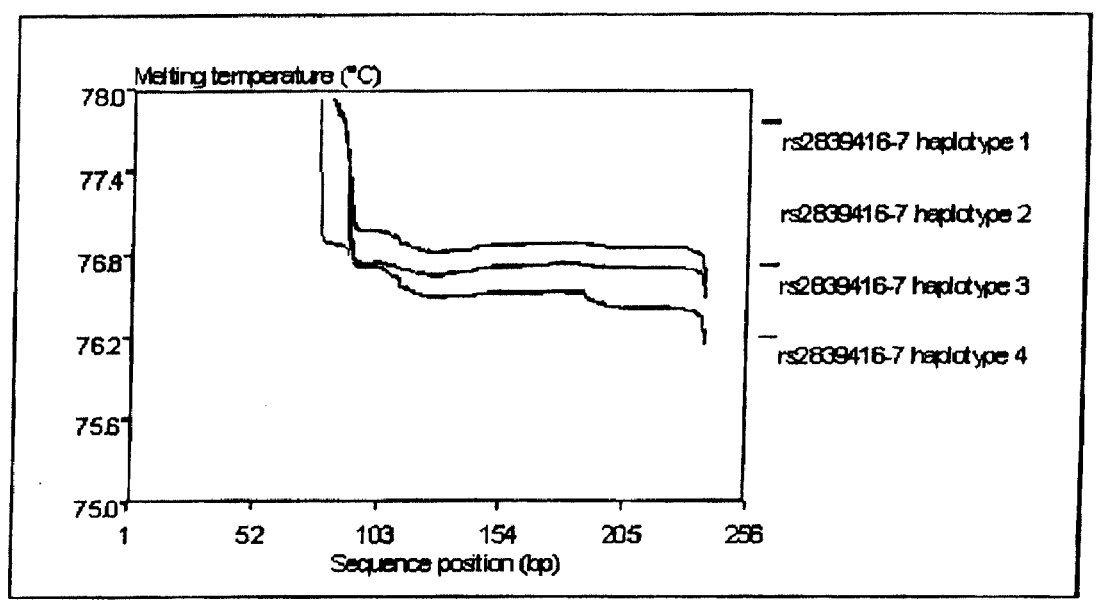
FIG. 7 provides a DNA melting map of a constant denaturant capillary electrophoresis target sequence covering a tandem SNP.

FIG. 7 depicts a DNA melting map of a CDCE or CTCE target sequence covering tandem SNPs. All four haplotypes can be theoretically separated according to DNA melting temperature. The curves for the four different haplotypes (haplotype 1 (G,A); haplotype 2 (T,A); haplotype 3 (G,G); and haplotype 4 (T,G)) are identified on the figure.

HiFi PCR optimization for each target sequence was performed using Pfu polymerase. One of primers flanking the target sequence was ~20 bases in length and labeled 5' with a fluorescein molecule. The other primer was about 74 bases including a ~20-base target specific sequence and the 54-base clamp sequence. A standard HiFi PCR condition was applied to all target sequences, varying only annealing temperatures. These PCR amplicons were subjected to CDCE or CTCE electrophoretic separation. The resulting electropherograms were analyzed for yield and purity of the PCR products. The purity was evaluated by comparing the peak area of the desired products to that of the byproducts and nonspecific amplification. Target sequences that could be amplified with a high PCR efficiency 45% per cycle) and low levels of byproducts and nonspecific amplification 0.1% of the desired products) were subjected to CDCE or CTCE optimization. For those target sequences that did not have acceptable PCR products in the first stage, increasing amounts of $Mg^{+2}$ concentrations (up to about 7 mM) in combination with different annealing temperatures were tested. For the remaining target sequences that still did not work, primer positions were changed and the entire optimization process is repeated.

For CDCE or CTCE optimization, the relevant haplotypes were created for the targets using pools of 96 individuals. The optimal separation condition for each haplotype should provide the greatest resolution among the observed peaks. Initial optimization is done around the theoretical melting temperature ($T_m$) in a 2° C. temperature range in increments of 0.2° C. which covers ($T_m$−1° C.±a predetermined offset) to ($T_m$+1° C.±a predetermined offset).

Electropherogram and peak measurements were transferred to a spreadsheet for analysis. To ensure the quality of the data, minimum and maximum peak heights were used. Individual markers were failed if electrophoretic spikes occur. Peak areas were used to calculate allele ratios. A check for allelic preferential amplification was performed on all 96 tandem SNPs.

In the fall of 2005, the International HapMap Project publicly released genotypes and frequencies from 270 people of four ethnic populations. Chromosome 21 haplotype data from approximately 40,000 SNPs genotyped across four populations, including U.S. residents with northern and western European ancestry, residents of Ibadan, Nigeria, of Tokyo, Japan, and of Beijing, China, were downloaded (2005-10-24: HapMap Public Release #19) and converted to the + orientation. Tandem SNP candidates fell within 100 basepairs from each other and at least three haplotypes existed in all four ethnic populations. CDCE or CTCE target sequences and primers were designed for the tandem SNPs identified through the HapMap Project. The neighboring sequences for each of the tandem SNPs were imported into a software program, e.g., Sequencher (Gene Codes, Ann Arbor, Mich.) and/or Vector NTI (Invitrogen, Carlsbad, Calif.) for sequence alignment and primer design, and into Winmelt (Medprobe, Oslo, Norway) or Poland software (available at biophys.uniduesseldorf.de/local/POLAND/poland.html) where the algorithm for computing DNA melting temperatures given the Gotoh-Tagashira values for the enthalpy of melting DNA sequences were used to calculate melting temperatures of target sequences. CDCE or CTCE candidates generally have a high melting region adjacent to a low melting region, lie in a low melting region, melting temperatures of the low melting region fall below 80° C., and no "valleys" occur between the high melting region and the low melting region.

All of the 40,000 genotypes on chromosome 21 were analyzed for tandem SNP/CDCE/CTCE marker suitability. 118 tandem SNPs/CDCE/CTCE targets meeting requirements have been identified (see FIG. 5 for the first 42 identified and FIG. 6 for all 118).

Primer sequences for these 118 tandem SNP/CDCE/CTCE targets were designed. These were optimized as described herein using HiFi PCR and CDCE or CTCE. These optimizations included the creation of relevant haplotypes for all targets, a check for allelic preferential amplification during HiFi PCR, and obtaining the greatest resolution among peaks during CDCE or CTCE. Haplotypes may be separated as homoduplex peaks. However, if certain targets cannot be separated out as homoduplexes, maternal DNA can be separated from fetal DNA as heteroduplexes.

Example 2

Determining Heterozygosity of Tandem SNPs

Genomic DNA samples from 300 anonymous subjects were obtained from healthy young adults who were less than 35 years old. The samples were anonymous as the only data obtained were the geographic location of the Red Cross blood donor center, donor gender, and whether or not the donor was 35 and under. These samples were reviewed to ensure that at least three haplotypes were present for a given target sequence of interest. These results were compared to haplotypes identified through analysis of the database from the HapMap project as described in Example 1, and it was found that the same or similar haplotypes were identified using both methods.

Example 3

Detecting Fetal DNA in Maternal Serum

A cohort of subjects confirmed to have trisomy 21 by traditional karyotype analysis was examined. Tandem SNPs were used to demonstrate detection of trisomy in subjects. DNA from 20 subjects who were characterized by traditional karyotype analysis to have trisomy 21 were analyzed with the tandem SNP panel.

Biological samples, including a buccal (cheek) swab and a blood sample were collected from a cohort of pregnant women. Maternal buccal swab samples were compared to maternal serum to demonstrate that a third (paternal) peak was observed in several of the tandem SNP assays. Approximately 20 maternal buccal swab to maternal serum comparisons were made. To control for experimental artifacts, genomic DNA samples from maternal buccal swabs were utilized for each target sequence. The buccal samples were subjected to the process in parallel with the maternal blood sample. Any artifacts generated by the CDCE/CTCE/HiFi-PCR procedure (including nonspecific PCR amplification and polymerase-induced mutations) were revealed as background peaks in the buccal swab samples.

Example 4

Detecting Fetal Chromosomal Abnormalities

Figure 3:
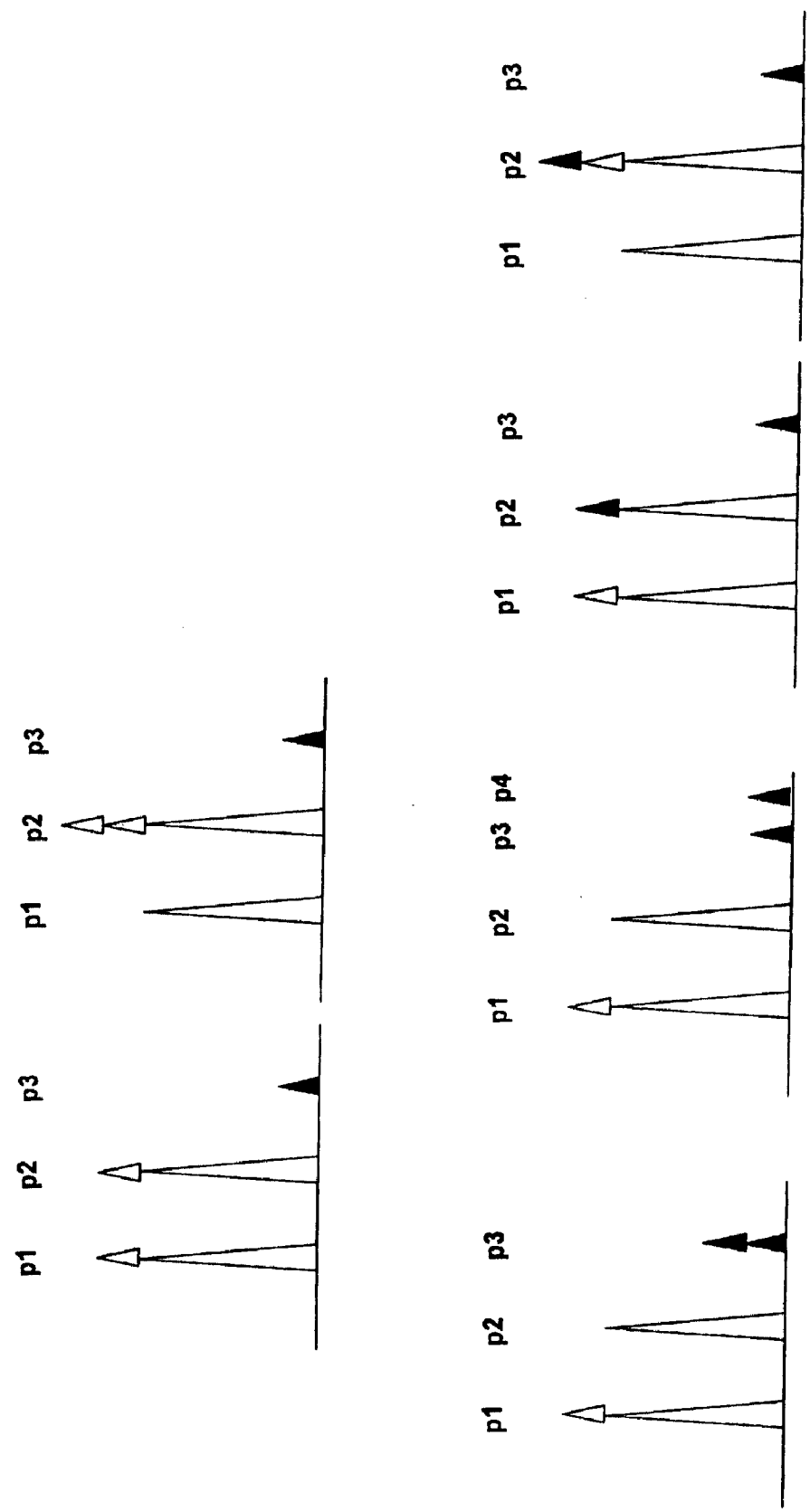
FIG. 3 is a schematic illustration of an embodiment of an assay of the invention.

A blinded study is performed where the goal is to detect 20 known trisomy 21 fetuses by assaying maternal serum from 40 patients (previously determined by amniocentesis or CVS) (see FIG. 3).

FIG. 1A depicts a schematic illustration of the output of detecting alleles in a sample from maternal buccal swab. Markers exhibiting two alleles were pursued. A baby with trisomy is expected to show either three alleles, evident by three peaks in a 1:1:1 ratio or two alleles in a 2:1 ratio. FIG. 1B depicts a sample from maternal serum. Markers exhibiting three alleles are informative. Maternal serum from a woman carrying a baby with trisomy is expected to exhibit three alleles, evident by two equal peaks with a third smaller peak if the trisomy occurred during meiosis I (75% of T21 cases) or three alleles with different areas if the trisomy occurred during meiosis II (20% of T21 cases) where areas are: peak, x, and peak+2x. FIG. 1C is a schematic illustration of the analysis of a sample from maternal serum. Markers exhibiting three alleles are informative. Maternal serum from a woman with a normal baby with three alleles has three different areas where areas are: peak, x, and peak+x.

Figure 8A:
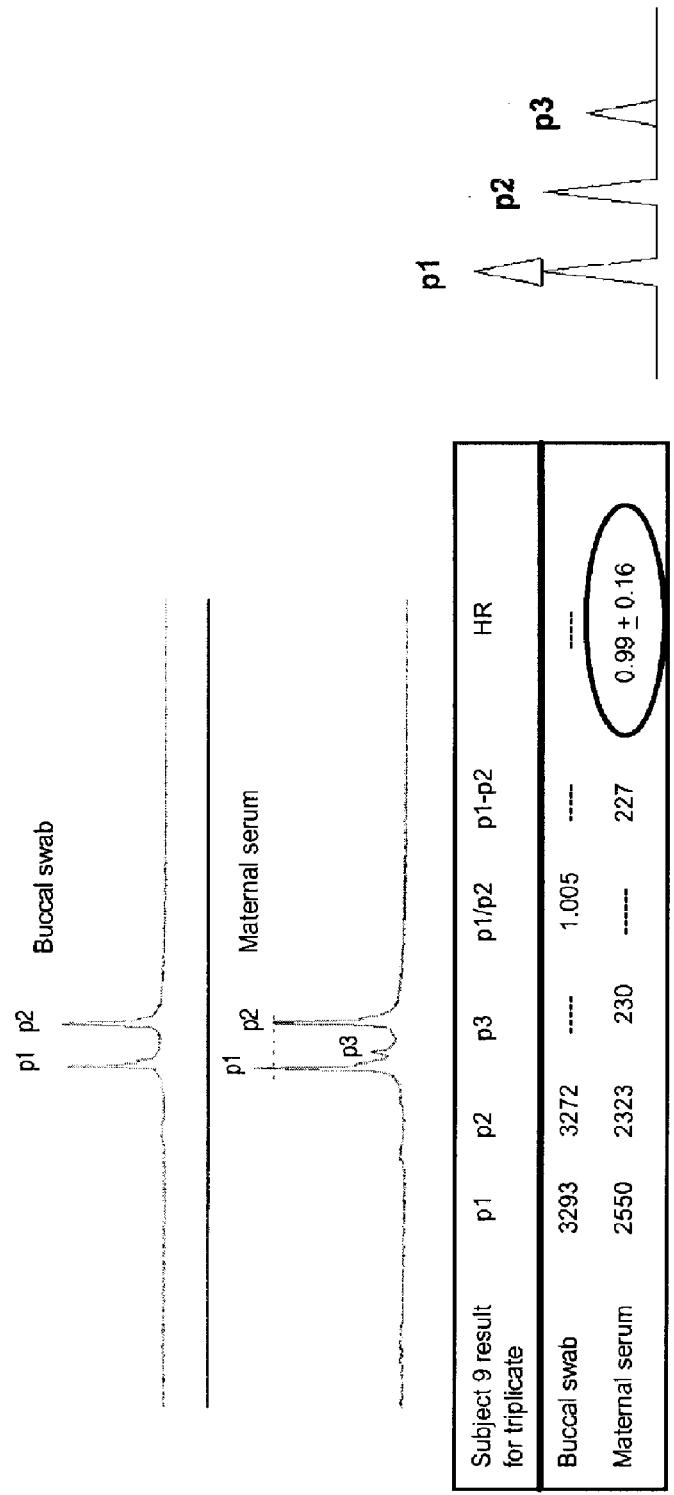
FIGS. 8A and B provides data of a haplotype ratio analysis.
Figure 8B:
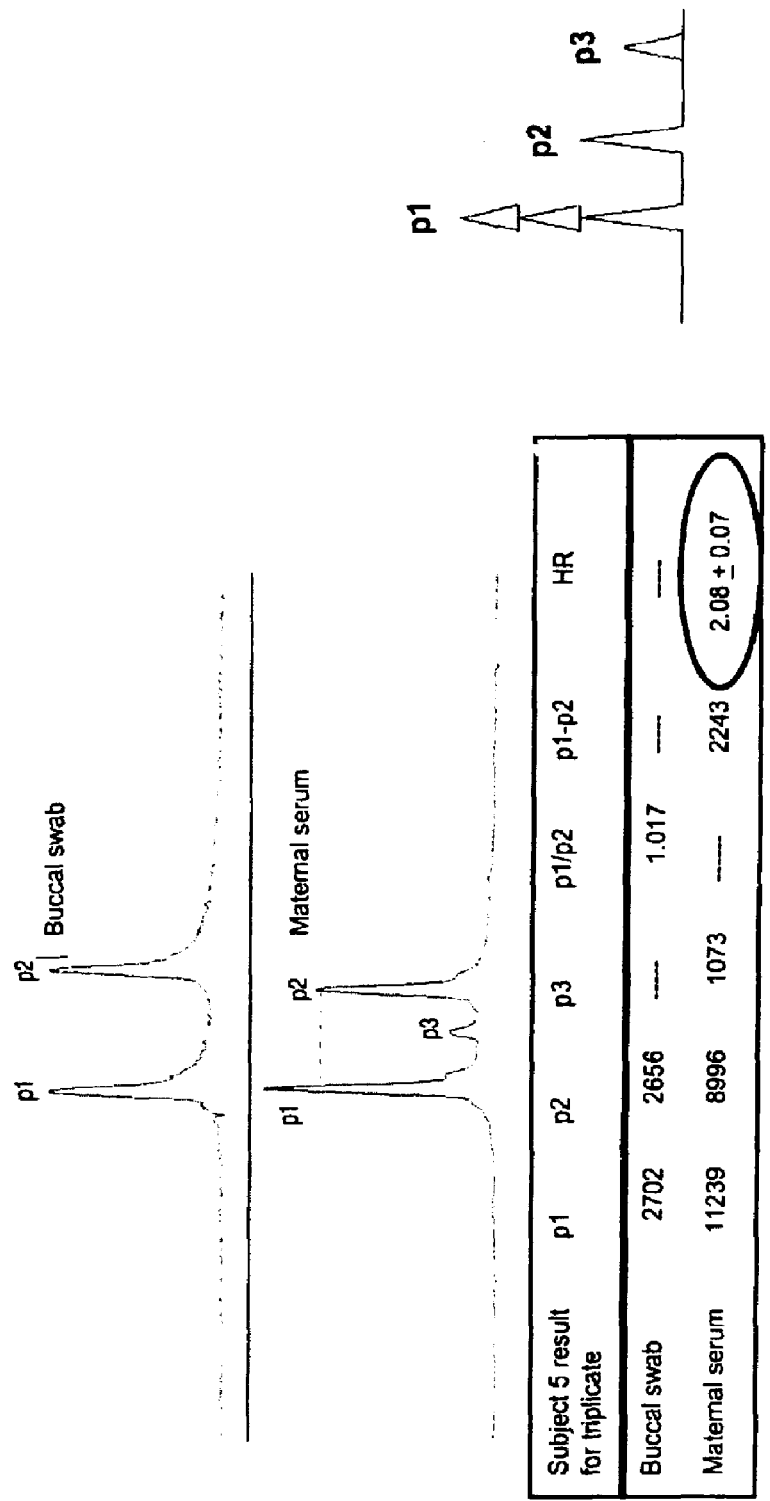

FIG. 8 shows data from a CDCE experiment for two different samples. In the top sample, the mother is carrying a non-trisomy 21 fetus. As expected, the haplotype ratio calculated from comparing the peaks in the output (which each represent a different allele, and the area under each of which provides the number of molecules for each allele) is within a margin of error to 1, the haplotype ratio expected for a normal fetus (see FIG. 8A). FIG. 8B shows the results for a mother carrying a fetus with trisomy 21. The haplotype ratio calculated from these data was within a margin of error to 2, which is one of the haplotype ratios expected for a fetus with a chromosomal abnormality.

For the case of the minimum heterozygosity, where both SNP1 and SNP2 are heterozygous at their respective loci at a rate of 25%, if 96 tandem SNPs are assayed, an average of 43 markers (44.5%) are expected to be heterozygous (two haplotypes) in the mother. The mother's expected heterozygosity is calculated using the following formula:

$$H = 1 - \Sigma p_i^2 \quad \text{(Formula III)}$$

wherein I=1 to k alleles and pi=estimated allele frequency.

The allele frequencies at each SNP loci are expected to be 85% and 15% for the majority and minority alleles, respectively, assuming Hardy-Weinberg equilibrium. The desired third haplotype is expected to be present at an average of 6.4 markers (15%) of per maternal-fetal sample tested. Because most loci have a heterozygosity value greater than 25%, for every maternal-fetal sample tested using the panel of 96 tandem SNP assays, greater than about 6.4 markers are most informative. Thus, while a panel of 96 tandem SNPs may be used, 6 or 7 of those tandem SNPs may be informative for any one specific maternal-fetal sample tested, and a 'positive' result from any one of those tandem SNPs is informative.

Finally, in order to diagnose a trisomy, a "positive" tandem SNPs should be identified on both the p and the q arm of chromosome 21. Because of the comparative nature of the basic approach, the tandem SNP assay is predicted to have a detection rate of 95% (those that occur during maternal meiosis) for trisomy 21. If paternal samples are available, non-disjunctions that occur during paternal meiosis can also be detected. Thus, detection rates would be higher (about ~99%) with a 0% false positive rate.

Example 5

Identification of Patients with Trisomy 21

A study was approved by the Institutional Review Board for Human Research at the Medical College of Wisconsin. 27 high risk pregnant patients who were scheduled to undergo amniocentesis or CVS or had already had either of these procedures were recruited as subjects at Froedtert Hospital. Informed consent was obtained from each participant before blood draws and buccal swabs were obtained.

Karyotype analysis confirmed 7 pregnancies carried a trisomy 21 fetus while 20 pregnancies carried a disomy 21 fetus. The gestational week and maternal age varied from 9-36.1 weeks and 22-43 years respectively. The gestational age ranged from first to third trimesters and the race and ethnicity of the subjects were (White (non-Hispanic), White (other), Asian, Other, and unknown).

The results from the study are shown in the table below:

TABLE 2

RESULTS OF STUDY CONFIRMED BY KARYOTYPE ANALYSIS

| Subject | Fetal Chromosome 21 status | Haplotype ratio (HR) | CV | % of fetal DNA (paternal contribution) |
|---|---|---|---|---|
| Subject 1 | Disomy | 1.21 | 0.39 | 7.4% |
| Subject 2 | Disomy | 1.19 | 0.06 | 10.8% |
| Subject 3 | Trisomy | 2.29 | 0.17 | 4.4% |
| Subject 4 | Trisomy | 2.55 | 0.22 | 1.3% |
| Subject 5 | Trisomy | 2.09 | 0.08 | 5.0% |
| Subject 6 | Trisomy | 2.33 | 0.26 | 3.3% |
| Subject 7 | Trisomy | 2.29 | 0.56 | 1.7% |
| Subject 8 | Trisomy | 0.05 | 0.05 | 7.1% |
| Subject 9 | Disomy | 0.95 | 0.16 | 5.5% |
| Subject 10 | Disomy | 1.04 | 0.05 | 19.7% |
| Subject 11 | Disomy | 1.00 | 0.05 | 8.0% |
| Subject 12 | Disomy | 0.99 | 0.31 | 6.8% |
| Subject 13 | Disomy | 0.90 | 0.26 | 7.3% |
| Subject 14 | Disomy | 1.04 | 0.05 | 24.0% |
| Subject 15 | Disomy | 1.15 | 0.12 | 4.0% |
| Subject 16 | Disomy | 1.06 | 0.11 | 2.9% |
| Subject 17 | Disomy | 0.92 | 0.26 | 4.0% |
| Subject 18 | Disomy | 1.35 | 0.02 | 11.7% |
| Subject 19 | Disomy | 0.95 | 0.13 | 9.2% |
| Subject 20 | Disomy | 1.29 | 0.23 | 3.7% |
| Subject 21 | Disomy | 1.46 | 0.07 | 7.0% |
| Subject 22 | Disomy | 1.21 | 0.14 | 6.4% |
| Subject 23 | Trisomy | 2.07 | 0.13 | 6.8% |
| Subject 24 | Disomy | 1.29 | 0.25 | 7.3% |
| Subject 25 | Disomy | 1.01 | 0.10 | 4.2% |
| Subject 26 | Disomy | 0.85 | 0.04 | 13.7% |
| Subject 27 | Disomy | 1.20 | 0.21 | 9.7% |

As is apparent from the above table, calculation of the haplotype ratio correctly identified each subject carrying a baby with trisomy and the haplotype ratio calculation was also able to correctly identify all normal pregnancies.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed is:

1. A method of quantifying relative amounts of maternal and fetal alleles of interest in
a sample comprising:
amplifying nucleotide sequences comprising a tandem single nucleotide polymorphism (SNP) from a sample comprising fetal and maternal nucleic acids, wherein a single pair of primers is used to amplify each of the nucleotide sequences;
detecting the amplified nucleotide sequences;
identifying amplified nucleotide sequences that comprise three alleles of the tandem SNP, wherein two of the three amplified nucleotide sequences comprise maternal alleles of the tandem SNP in the maternal nucleic acid and one of the amplified nucleotide sequences comprises a fetal allele of the tandem SNP in the fetal nucleic acid that is absent in the maternal nucleic acid;
quantifying amounts of maternal alleles of the tandem SNP and quantifying an amount of fetal allele of the tandem SNP; and
comparing the amount of maternal alleles of the tandem SNP to the amount of a fetal allele of the tandem SNP to determine the amount of fetal nucleic acid relative to maternal nucleic acid in the sample.

2. The method of claim 1, wherein the tandem SNPs are at a distance from one another of 250 bp or less.

3. The method of claim 1, wherein the amplified nucleotide sequences are detected using PCR methods.

4. The method of claim 1, wherein the amplified nucleotide sequences are detected using high performance liquid chromatography (HPLC).

5. The method of claim 1, wherein the amplified nucleotide sequences are detected using sequencing techniques.

6. The method of claim 5, wherein the amplified nucleotide sequences are detected using a high throughput sequencing platform.

7. The method of claim 5, wherein the sequencing technique used is single molecule sequencing.

8. The method of claim 1, wherein the amounts compared are numbers of molecules for each of the amplified nucleotide sequences.

9. A method of calculating an allelic ratio for multiple alleles in a sample, comprising:
amplifying nucleotide sequences comprising multiple alleles from a sample comprising fetal and maternal nucleic acids, wherein a single pair of primers is used to amplify the nucleotide sequences;
detecting the amplified nucleotide sequences using sequencing methods;
identifying amplified nucleotide sequences with multiple alleles comprising three different alleles, wherein two of the three amplified nucleotide sequences are maternal alleles and one of the three amplified nucleotide sequences is a fetal allele absent in the maternal nucleic acids;
quantifying the three different alleles; and
calculating an allelic ratio for the multiple alleles present in the sample, wherein the multiple allelic ratios are detected in a single reaction or assay.

10. The method of claim 9, wherein the amplified nucleotide sequences are detected using a high throughput sequencing platform.

11. The method of claim 9, wherein the amplified nucleotide sequences are detected using high performance liquid chromatography (HPLC).

12. The method of claim 9, wherein the allelic ratio is a ratio of numbers of molecules for each of the amplified nucleotide sequences.

* * * * *